United States Patent
Fodor et al.

(10) Patent No.: US 9,727,810 B2
(45) Date of Patent: Aug. 8, 2017

(54) SPATIALLY ADDRESSABLE MOLECULAR BARCODING

(71) Applicant: Cellular Research, Inc., Menlo Park, CA (US)

(72) Inventors: Stephen P. A. Fodor, Menlo Park, CA (US); Christina Fan, Menlo Park, CA (US); Glenn Fu, Menlo Park, CA (US); Geoffrey Facer, Menlo Park, CA (US)

(73) Assignee: Cellular Research, Inc., Menlo Park, CA (US)

( * ) Notice: Subject to any disclaimer, the term of this patent is extended or adjusted under 35 U.S.C. 154(b) by 0 days.

(21) Appl. No.: 15/055,445

(22) Filed: Feb. 26, 2016

(65) Prior Publication Data

US 2016/0253584 A1 Sep. 1, 2016

Related U.S. Application Data

(60) Provisional application No. 62/126,230, filed on Feb. 27, 2015, provisional application No. 62/162,471, filed on May 15, 2015.

(51) Int. Cl.
G06K 19/06 (2006.01)
C12Q 1/68 (2006.01)

(52) U.S. Cl.
CPC ..... G06K 19/06103 (2013.01); C12Q 1/6813 (2013.01); C12Q 1/6816 (2013.01)

(58) Field of Classification Search
None
See application file for complete search history.

(56) References Cited

U.S. PATENT DOCUMENTS

| | | | |
|---|---|---|---|
| 4,510,244 A | 4/1985 | Parks et al. |
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |

(Continued)

FOREIGN PATENT DOCUMENTS

| | | |
|---|---|---|
| DE | 102008025656 | 12/2009 |
| EP | 0 799 897 | 10/1997 |

(Continued)

OTHER PUBLICATIONS

Cai, Mar. 2013, Turning single cells in microarrays by super-resolution bar-coding, Brief Funct Genomics, 12(2):75-80.

(Continued)

Primary Examiner — Kristy A Haupt
(74) Attorney, Agent, or Firm — Knobbe, Martens, Olson & Bear, LLP

(57) ABSTRACT

The disclosure provides for methods, compositions, systems, devices, and kits for determining the number of distinct targets in distinct spatial locations within a sample. In some examples, the methods include: stochastically barcoding the plurality of targets in the sample using a plurality of stochastic barcodes, wherein each of the plurality of stochastic barcodes comprises a spatial label and a molecular label; estimating the number of each of the plurality of targets using the molecular label; and identifying the spatial location of each of the plurality of targets using the spatial label. The method can be multiplexed.

30 Claims, 29 Drawing Sheets

(56) References Cited

U.S. PATENT DOCUMENTS

| | | |
|---|---|---|
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,235,475 B1 | 5/2001 | Brenner et al. |
| 6,268,152 B1 | 7/2001 | Fodor et al. |
| 6,284,460 B1 | 9/2001 | Fodor et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,155,050 B1 | 12/2006 | Sloge |
| 7,393,665 B2 | 7/2008 | Brenner |
| 7,424,368 B2 | 9/2008 | Huang et al. |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,228,229 B2 | 1/2016 | Olson et al. |
| 9,290,808 B2 | 3/2016 | Fodor et al. |
| 9,290,809 B2 | 3/2016 | Fodor et al. |
| 9,315,857 B2 | 4/2016 | Fu et al. |
| 2002/0072058 A1 | 6/2002 | Voelker et al. |
| 2002/0168665 A1 | 11/2002 | Okawa |
| 2003/0003490 A1 | 1/2003 | Fan et al. |
| 2003/0049616 A1 | 3/2003 | Brenner et al. |
| 2003/0082818 A1 | 5/2003 | Bahnson et al. |
| 2003/0104436 A1 | 6/2003 | Morris et al. |
| 2003/0175908 A1 | 9/2003 | Linnarson |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0019776 A1 | 1/2005 | Callow et al. |
| 2005/0170373 A1 | 8/2005 | Monforte |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0041385 A1 | 2/2006 | Bauer |
| 2006/0073506 A1 | 4/2006 | Christians et al. |
| 2006/0211030 A1 | 9/2006 | Brenner |
| 2006/0263709 A1 | 11/2006 | Matsumura et al. |
| 2006/0263789 A1 | 11/2006 | Kincaid |
| 2007/0020640 A1 | 1/2007 | Mccloskey et al. |
| 2007/0065823 A1 | 3/2007 | Dressman et al. |
| 2007/0117134 A1 | 5/2007 | Kou |
| 2007/0172873 A1 | 7/2007 | Brenner et al. |
| 2007/0178478 A1 | 8/2007 | Dhallan et al. |
| 2008/0070303 A1 | 3/2008 | West et al. |
| 2008/0194414 A1 | 8/2008 | Albert et al. |
| 2008/0261204 A1 | 10/2008 | Lexow |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0061513 A1 | 3/2009 | Andersson et al. |
| 2009/0105959 A1 | 4/2009 | Braverman et al. |
| 2009/0137407 A1 | 5/2009 | Church et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0298709 A1 | 12/2009 | Ma |
| 2010/0069250 A1 | 3/2010 | White, III |
| 2010/0105049 A1 | 4/2010 | Ehrich et al. |
| 2010/0105886 A1 | 4/2010 | Woudenberg et al. |
| 2010/0120630 A1 | 5/2010 | Huang et al. |
| 2010/0255471 A1 | 10/2010 | Clarke |
| 2010/0291666 A1 | 11/2010 | Collier et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0070584 A1 | 3/2011 | Wohlgemuth et al. |

(56) References Cited

U.S. PATENT DOCUMENTS

| | | |
|---|---|---|
| 2011/0072889 A1 | 3/2011 | Albitar et al. |
| 2011/0160078 A1* | 6/2011 | Fodor .................. C12Q 1/6809 506/9 |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0010091 A1 | 1/2012 | Linnarson |
| 2012/0040843 A1 | 2/2012 | Ducree et al. |
| 2012/0045844 A1 | 2/2012 | Rothberg et al. |
| 2012/0065081 A1 | 3/2012 | Chee |
| 2012/0071331 A1 | 3/2012 | Casbon |
| 2012/0156675 A1 | 6/2012 | Lueerssen et al. |
| 2012/0163681 A1 | 6/2012 | Lohse |
| 2012/0173159 A1 | 7/2012 | Davey et al. |
| 2012/0190020 A1 | 7/2012 | Oliphant et al. |
| 2012/0220022 A1 | 8/2012 | Ehrlich et al. |
| 2012/0220494 A1 | 8/2012 | Samuels |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu et al. |
| 2013/0190206 A1 | 7/2013 | Leonard |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0206547 A1 | 7/2014 | Wang |
| 2014/0216128 A1 | 8/2014 | Trotter et al. |
| 2014/0227684 A1 | 8/2014 | Hindson et al. |
| 2014/0227705 A1 | 8/2014 | Vogelstein et al. |
| 2014/0228255 A1 | 8/2014 | Hindson et al. |
| 2014/0235506 A1 | 8/2014 | Hindson et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005185 A1 | 1/2015 | Fodor et al. |
| 2015/0005199 A1 | 1/2015 | Hindson et al. |
| 2015/0005200 A1 | 1/2015 | Hindson et al. |
| 2015/0066385 A1 | 3/2015 | Schnall-Levin et al. |
| 2015/0099673 A1 | 4/2015 | Fodor et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0225778 A1 | 8/2015 | Hindson et al. |
| 2015/0298091 A1 | 10/2015 | Weitz |
| 2015/0299784 A1 | 10/2015 | Fan et al. |
| 2015/0307874 A1 | 10/2015 | Jaitin |
| 2015/0376609 A1 | 12/2015 | Hindson et al. |
| 2016/0010151 A1 | 1/2016 | Fan et al. |
| 2016/0026758 A1 | 1/2016 | Jabara et al. |
| 2016/0055632 A1 | 2/2016 | Fu et al. |
| 2016/0145683 A1 | 5/2016 | Fan et al. |
| 2016/0222378 A1 | 8/2016 | Fodor et al. |
| 2016/0244828 A1 | 8/2016 | Mason |
| 2016/0257993 A1 | 9/2016 | Fu et al. |
| 2016/0265069 A1 | 9/2016 | Fan et al. |
| 2016/0289669 A1 | 10/2016 | Fan et al. |
| 2016/0289740 A1 | 10/2016 | Fu et al. |
| 2016/0312276 A1 | 10/2016 | Fu et al. |
| 2016/0326584 A1 | 11/2016 | Fodor et al. |
| 2016/0340720 A1 | 11/2016 | Fan et al. |
| 2016/0376583 A1 | 12/2016 | Fodor et al. |
| 2016/0376648 A1 | 12/2016 | Fodor et al. |
| 2017/0073730 A1 | 3/2017 | Betts et al. |

FOREIGN PATENT DOCUMENTS

| | | |
|---|---|---|
| EP | 1 473 080 | 11/2004 |
| EP | 1 647 600 | 4/2006 |
| EP | 1 845 160 | 10/2007 |
| EP | 2 623 613 | 8/2013 |
| EP | 2 805 769 | 11/2014 |
| WO | WO 89/01050 | 2/1989 |
| WO | WO 97/10365 | 3/1997 |
| WO | WO 99/15702 | 4/1999 |
| WO | WO 99/28505 | 6/1999 |
| WO | WO 00/58516 | 10/2000 |
| WO | WO 02/056014 | 7/2002 |
| WO | WO 02/070684 | 9/2002 |
| WO | WO 2004/017374 | 2/2004 |
| WO | WO 2005/042759 | 5/2005 |
| WO | WO 2005/071110 | 8/2005 |
| WO | WO 2005/080604 | 9/2005 |
| WO | WO 2005/111242 | 11/2005 |
| WO | WO 2006/071776 | 7/2006 |
| WO | WO 2006/102264 | 9/2006 |
| WO | WO 2007/087310 | 8/2007 |
| WO | WO 2007/087312 | 8/2007 |
| WO | WO 2008/096318 | 8/2008 |
| WO | WO 2009/148560 | 12/2009 |
| WO | WO 2009/152928 | 12/2009 |
| WO | WO 2010/117620 | 10/2010 |
| WO | WO 2011/123246 | 10/2011 |
| WO | WO 2011/143659 | 11/2011 |
| WO | WO 2011/155833 | 12/2011 |
| WO | WO 2012/038839 | 3/2012 |
| WO | WO 2012/042374 | 4/2012 |
| WO | WO 2012/047297 | 4/2012 |
| WO | WO 2012/048341 | 4/2012 |
| WO | WO 2012/083225 | 6/2012 |
| WO | WO 2012/108864 | 8/2012 |
| WO | WO 2012/129363 | 9/2012 |
| WO | WO 2012/140224 | 10/2012 |
| WO | WO 2012/142213 | 10/2012 |
| WO | WO 2012/148477 | 11/2012 |
| WO | WO 2012/149042 | 11/2012 |
| WO | WO 2012/162267 | 11/2012 |
| WO | WO 2013/019075 | 2/2013 |
| WO | WO 2013/117595 | 8/2013 |
| WO | WO 2013/130674 | 9/2013 |
| WO | WO 2013/173394 | 11/2013 |
| WO | WO 2013/176767 | 11/2013 |
| WO | WO 2013/177206 | 11/2013 |
| WO | WO 2013/188831 | 12/2013 |
| WO | WO 2013/188872 | 12/2013 |
| WO | WO 2013/191775 | 12/2013 |
| WO | WO 2014/015084 | 1/2014 |
| WO | WO 2014/015098 | 1/2014 |
| WO | WO 2014/018460 | 1/2014 |
| WO | WO 2014/028537 | 2/2014 |
| WO | WO 2014/071361 | 5/2014 |
| WO | WO 2014/093676 | 6/2014 |
| WO | WO 2014/108850 | 7/2014 |
| WO | WO 2014/124336 | 8/2014 |
| WO | WO 2014/124338 | 8/2014 |
| WO | WO 2014/126937 | 8/2014 |
| WO | WO 2014/144495 | 9/2014 |
| WO | WO 2014/201273 | 12/2014 |
| WO | WO 2014/210353 | 12/2014 |
| WO | WO 2015/031691 | 3/2015 |
| WO | WO 2015/035087 | 3/2015 |
| WO | WO 2015/044428 | 4/2015 |

(56) References Cited

FOREIGN PATENT DOCUMENTS

| WO | WO 2015/047186 | 4/2015 |
|---|---|---|
| WO | WO 2015/103339 | 7/2015 |
| WO | WO 2015/200869 | 12/2015 |

OTHER PUBLICATIONS

Castellarnau et al., Jan. 2015, Stochastic particle barcoding for single-cell tracking and multiparametric analysis, Small, 11(4):489-498.
Dalerba et al., 2011, Single-cell dissection of transcriptional heterogeneity in human colon tumors, Nat Biotechnol., 29(12):1120-1127 and Supplementary Material.
Fan, Nov. 2010, Molecular counting: from noninvasive prenatal diagnostics to whole-genome haplotyping, doctoral dissertation, Stanford University, 185 pp.
Gong et al., 2010, Massively parallel detection of gene expression in single cells using subnanolitre wells, Lab Chip, 10:2334-2337.
Haff, 1994, Improved quantitative PCR using nested primers, PCR Methods and Applications, 3:332-337.
Kebschull et al., Jul. 17, 2015, Sources of PCR-induced distortions in high-throughput sequencing data sets, Nucleic Acids Research, 15 pp.
Kim et al., Jun. 8, 2007, Polony multiplex analysis of gene expression (PMAGE) in mouse hypertrophic cardiomyopathy, Science, 316(5830):1481-1484.
Kotake et al., 1996, A simple nested RT-PCR method for quantitation of the relative amounts of multiple cytokine mRNAs in small tissue samples, Journal of Immunological Methods, 199:193-203.
Kurimoto et al., Mar. 17 2006, An improved single-cell cDNA amplification method for efficient high-density oligonucleotide microarray analysis, Nucleic Acids Res., 34(5):e42.
Lee et al., 2010, Large-scale arrays of picolitre chambers for single-cell analysis of large cell populations, Lab Chip, 10:2952-2958.
Marcus et a., 2006, Microfluidic single-cell mRNA isolation and analysis, Ana. Chem. 78:3084-3089.
Nagai et al., 2001, Development of a microchamber array for picoleter PCR, Anal. Chem., 73:1043-1047.
Picelli et al., Jul. 30, 2014, Tn5 transposase and tagmentation procedures for massively scaled sequencing projects, Genome Research 24(12):2033-2040.
Soumillon et al., Mar. 5, 2014, Characterization of directed differentiation by high-throughput single-cell RNA-Seq, bioRxiv preprint, http://biorxiv.org/content/early/2014/03/05/003236.full.pdf, 13 pp.
Speicher et al., Oct. 2005, The new cytogenetics: blurring the boundaries with molecular biology, Nature Reviews Genetics, 6(10):782-792.
Takahashi et al., Mar. 2006, Novel technique of quantitative nested real-time PCR assay for mycobacterium tuberculosis DNA, Journal of Clinical Microbiology, 44(3):1029-1039.
Wang et al., May 21, 2015, Advances and applications of single-cell sequencing technologies, Molecular Cell, 58(4):598-609.
Warren et al., Nov. 21, 2006, Transcription factor profiling in individual hematopoietic progenitors by digital RT-PCR, PNAS, 103(47):17807-17812.
White et al., Aug. 23, 2011, High-throughput microfluidic single-cell RT-qPCR, PNAS, 108(34):13999-14004.
Zheng et al., Feb. 2016, Haplotyping germline and cancer genomes with high-throughput linked-read sequencing, Nature Biotechnology, 34(3):303-311.
International Search Report and Written Opinion dated May 3, 2016 in PCT/US16/018354.
Office action dated Jul. 20, 2016 for U.S. Appl. No. 14/281,706.
Office Action dated May 10, 2016 in U.S. Appl. No. 14/381,488.
Office Action dated Aug. 12, 2016 in U.S. Appl. No. 14/381,488.
Second Office Action dated Jun. 6, 2016 in Chinese patent application No. 201380022187.9.
Examination report dated Jul. 12, 2016 in European patent application No. 13755319.4.
Examination Report dated Jun. 8, 2016 in GB patent application No. 1408829.8.
Office action dated Aug. 17, 2016 for U.S. Appl. No. 14/800,526.
Examination Report dated Jun. 15, 2016 in Great Britain patent application No. GB1511591.8.
Office Action dated May 13, 2016 in U.S. Appl. No. 14/508,911.
International Search Report and Written Opinion dated Jun. 20, 2016 in PCT/US16/14612.
International Search Report and Written Opinion dated Jun. 17, 2016 in PCT/US16/019962.
Written Opinion dated Jul. 5, 2016 in PCT/US16/019962.
Invitation to Pay Additional Search Fees dated Jun. 2, 2016 in PCT/US16/019971.
ISR and WO dated Aug. 9, 2016 in PCT/US16/019971.
International Search Report and Written Opinion dated Jun. 9, 2016 in PCT/US16/022712.
Anderson, Feb. 11, 2014, Study describes RNA sequencing applications for molecular indexing methods, genomeweb.com, 5 pp.
Bioscribe, Feb. 5, 2015, Massively parallel sequencing technology for single-cell gene expression published (press release), 3 pp.
Brisco et al., Jun. 25, 2012, Quantification of RNA integrity and its use for measurement of transcript number, Nucleic Acids Research, 40(18):e144.
Butkus, Feb. 6, 2014, Cellular research set to launch first gene expression platform using 'molecular indexing' technology, genomeweb.com, 5 pp.
Junker et al., May 21, 2015, Single-cell transcriptomics enters the age of mass production, Molecular Cell, 58:563-564.
Klein et al., May 21, 2015, Droplet barcoding for single-cell transcriptomics applied to embryonic stem cells, Cell, 161:1187-1201.
Kolodziejczyk et al., May 21, 2015, The technology and biology of single-cell RNA sequencing, Molecular Cell, 58:610-620.
Lamble et al., Nov. 20, 2013, Improved workflows for high throughput library preparation using the transposome-based nextera system, BMC Biotechnology, 13(1):104.
Liu et al., Single-cell transcriptome sequencing: recent advances and remaining challenges, F1000Research 2016, 5(F1000 Faculty Rev):182, 9 pp.
Martinez et al., Jul. 2012, A microfluidic approach to encapsulate living cells in uniform alginate hydrogel microparticles, Macromol. Biosci, 12(7):946-951.
Nadai et al., 2008, Protocol for nearly full-length sequencing of HIV-1 RNA from plasma, PLoS One, 3(1):e1420.
Navin et al., 2015, The first five years of single-cell cancer genomics and beyond, Genome Research, 25(10):1499-1507.
Pfaffl et al., Mar. 2004, Determination of stable housekeeping genes, differentially regulated target genes and sample integrity: BestKeeper—Excel-based tool using pair-wise correlations, Biotechnology Letters, 26(6):505-515.
Rajeevan et al., Oct. 2003, Global amplification of sense RNA: a novel method to replicate and archive mRNA for gene expression analysis, Genomics, 82(4):491-497.
Stratagene 1998 Catalog, Gene Characterization Kits, p. 39.
Vandesompele et al., Jun. 18, 2002, Accurate normalization of real-time quantitative RT-PCR data by geometric averaging of multiple internal control genes, Genome Biology, 3(7).
Weiner et al., Apr. 2008, Kits and their unique role in molecular biology: a brief retrospective, BioTechniques, 44:701-704.
Office Action dated Oct. 11, 2016 in U.S. Appl. No. 15/224,460.
Office Action dated Oct. 25, 2015 in U.S. Appl. No. 14/872,337.
Office action dated Sep. 26, 2016 in U.S. Appl. No. 15/167,807.
Written Opinion dated Sep. 27, 2016 in PCT/US16/019962.
International Search Report and Written Opinion dated Sep. 28, 2016 in PCT/US16/028694.
International Search Report and Written Opinion dated Sep. 27, 2016 in PCT/US16/034473.
Achim et al., May 2015, High-throughput spatial mapping of single-cell RNA-seq data to tissue of origin. Nature Biotechnology, 33(5):503-511.

(56) References Cited

OTHER PUBLICATIONS

Alkan et al., Oct. 2009, Personalized copy number and segmental duplication maps using next-generation sequencing. Nat Genet., 41(10):1061-1067.
Ansorge, 2009, Next-generation DNA sequencing techniques. New Biotechnology, 25(4):195-203.
Atanur et al., Jun. 2010, The genome sequence of the spontaneously hypertensive rat: Analysis and functional significance. Genome Res., 20(6):791-803.
Audic et al., 1997, The Significance of Digital Gene Expression Profiles. Genome Research, 7:986-995.
Bendall et al., May 6, 2011, Single-cell mass cytometry of differential immune and drug responses across a human hematopoietic continuum. Science, 332(6030):687-696.
Bionumbers, Aug. 21, 2010, Useful fundamental numbers in molecular biology, http://bionumbers.hms.harvard.edu/KeyNumbers/aspx, 4 pp.
Blainey, May 2013, The future is now: single-cell genomics of bacteria and archaea, FEMS Microbiol Rev., 37(3):407-427.
Bonaldo et al., Sep. 1996, Normalization and subtraction: two approaches to facilitate gene discovery. Genome Res., 6(9):791-806.
Braha et al., 2000, Simultaneous stochastic sensing of divalent metal ions. Nature Biotechnology, 18:1005-1007.
Bratke et al., Sep. 2005, Differential expression of human granzymes A, B, and K in natural killer cells and during CD8+ T cell differentiation in peripheral blood. Eur J Immunol., 35(9):2608-2616.
Brenner et al., 2000, Gene expression analysis by massively parallel signature sequencing (MPSS) on microbead arrays. Nature Biotechnology, 18:630-634.
Brenner et al., Feb. 15, 2000, In vitro cloning of complex mixtures of DNA on microbeads: physical separation of differentially expressed cDNAs. Proc Natl Acad Sci, 97(4):1665-1670.
Brodin et al., 2015, Challenges with using primer IDs to improve accuracy of next generation sequencing, 19(3):1-12.
Carr et al., Dec. 15, 2009, Inferring relative proportions of DNA variants from sequencing electropherograms. Bioinformatics, 25(24):3244-3250.
Casbon et al., Jul. 2011, A method for counting PCR template molecules with application to next-generation sequencing. Nucleic Acids Res., 39(12):e81.
Castle et al., Apr. 16, 2010, DNA copy number, including telomeres and mitochondria, assayed using next-generation sequencing. BMC Genomics, 11:244. doi: 10.1186/1471-2164-11-244.
Chamberlain et al., Dec. 9, 1988, Deletion screening of the Duchenne muscular dystrophy locus via multiplex DNA amplification. Nucleic Acids Res., 16(23):11141-11156.
Chang et al., Aug. 2002, Detection of allelic imbalance in ascitic supernatant by digital single nucleotide polymorphism analysis. Clin Cancer Res., 8(8):2580-2585.
Chee et al., 1996, Accessing genetic information with high-density DNA arrays, Science, 274:610-614.
Chee, 1991, Enzymatic multiplex DNA sequencing. Nucleic Acids Research, 19(12): 3301-3305.
Chen et al., Apr. 9, 2015, Spatially resolved, highly multiplexed RNA profiling in single cells. Science Express, pp. 1-21.
Church et al., 1988, Multiplex DNA sequencing. Science, 240:185-188.
Costello et al., Apr. 1, 2013, Discovery and characterization of artifactual mutations in deep coverage targeted capture sequencing data due to oxidative DNA damage during sample preparation. Nucleic Acids Res, 41(6):e67.
Cox. May 2001, Bar coding objects with DNA. Analyst, 126(5):545-547.
Craig et al., Oct. 2008, Identification of genetic variants using bar-coded multiplexed sequencing. Nat Methods, 5(10):887-893.
Cusanovich et al., May 7, 2014, Multiplex single-cell profiling of chromatin accessibility by combinatorial cellular indexing. Science Express, pp. 1-9.
Daines et al., Aug. 2009, High-throughput multiplex sequencing to discover copy number variants in Drosophila. Genetics, 182(4):935-941.
D'Antoni et al., May 1, 2006, Rapid quantitative analysis using a single molecule counting approach. Anal Biochem. 352(1):97-109.
Daser et al., 2006, Interrogation of genomes by molecular copy-number counting (MCC). Nature Methods, 3(6):447-453.
De Saizieu et al., 1998, Bacterial transcript imaging by hybridization of total RNA to oligonucleotide arrays. Nature Biotechnology, 16:45-48.
Dirks et al., Oct. 26, 2004, Triggered amplification by hybridization chain reaction., Proc Natl Acad Sci U S A, 101(43),15275-15278.
Fan et al., Feb. 6, 2015, Combinatorial labeling of single cells for gene expression cytometry. Science, 347(6222):1258367-8.
Fan et al., 2000, Parallel Genotyping of Human SNPs Using Generic High-density Oligonucleotide Tag Arrays. Genome Research, 10:853-860.
Fan et al., 2009, Microfluidic digital PCR enables rapid prenatal diagnosis of fetal aneuploidy. Am Obstet Gynecol. 200:543.e1-543.e7.
Fan et al., Jul. 19, 2012, Non-invasive prenatal measurement of the fetal genome. Nature, 487(7407):320-324.
Feldhaus et al., Jan. 15, 2000, Oligonucleotide-conjugated beads for transdominant genetic experiments, Nucleic Acids Res., 28(2):534-543.
Fox-Walsh et al., Oct. 2011, A multiplex RNA-seq strategy to profile poly(A+) RNA: application to analysis of transcription response and 3' end formation., Genomics, 98(4),266-721.
Fu et al., Marcy 18, 2014, Digital encoding of cellular mRNAs enabling precise and absolute gene expression measurement by single-molecule counting. Anal Chem., 86(6):2867-2870.
Fu et al., May 31, 2011, Counting individual DNA molecules by the stochastic attachment of diverse labels. Proc Natl Acad Sci, 108(22):9026-9031.
Gerry et al., 1999, Universal DNA microarray method for multiplex detection of low abundance point mutations. Journal of Molecular Biology, 292(2): 251-262.
Gillespie, 1977, Exact stochastic simulation of coupled chemical reactions. The Journal of Physical Chemistry, 81(25):2340-2361.
Grant et al., Nov. 15, 2002, SNP genotyping on a genome-wide amplified DOP-PCR template. Nucleic Acids Res, 30(22):e125.
Gunderson et al., May 2004, Decoding randomly ordered DNA arrays. Genome Res. 14(5):870-877.
Gundry et al., Jan. 3, 2012, Direct mutation analysis by high-throughput sequencing: from germline to low-abundant, somatic variants. Mutat Res. 729(1-2):1-15.
Gundry et al., Mar. 2012, Direct, genome-wide assessment of DNA mutations in single cells. Nucleic Acids Res., 40(5):2032-40.
Hacia et al., 1999, Determination of ancestral alleles for human single-nucleotide polymorphisms using high-density oligonucleotide arrays. Nature Genetics, 22:164-167.
Hamady et al., Mar. 2008, Error-correcting barcoded primers for pyrosequencing hundreds of samples in multiplex. Nat Methods, 5(3):235-237.
Harrington et al.,2009, Cross-sectional characterization of HIV-1 env compartmentalization in cerebrospinal fluid over the full disease course, AIDS, 23(8) 907-915.
Hashimshony et al., Sep. 27, 2012, CEL-Seq: single-cell RNA-Seq by multiplexed linear amplification Cell Rep. 2(3):666-673.
Hensel et al., Jul. 21, 1995, Simultaneous identification of bacterial virulence genes by negative selection. Science. 269(5222):400-403.
Hiatt et al., Feb. 2010, Parallel, tag-directed assembly of locally derived short sequence reads. Nat Methods, 7(2):119-122.
Hiatt et al., May 2013, Single molecule molecular inversion probes for targeted, high-accuracy detection of low-frequency variation. Genome Res., 23(5):843-854.
Hollas et al., 2003, A stochastic approach to count RNA molecules using DNA sequencing methods. Lecture Notes in Computer Science, 2812:55-62.
Hug et al., 2003, Measure of the number of molecular of a single mRNA species in a complex mRNA preparation, Journal of Theoretical Biology, 221:615-624.

(56) References Cited

OTHER PUBLICATIONS

Ingolia et al., Apr. 10, 2009, Genome-wide analysis in vivo of translation with nucleotide resolution using ribosome profiling. Science, 324(5924):218-223.
Islam et al., 2011, Characterization of the single-cell transcriptional landscape by highly multiplex RNA-seq. Genome Research, 21:1160-1167.
Islam et al., 2014, Quantitative single-cell RNA-seq with unique molecular identifiers, Nature Methods, 11(2):163-168.
Jabara et al., Dec. 3, 2011, Accurate sampling and deep sequencing of the HIV-1 protease gene using a Primer ID, PNAS, 108(50):20166-20171.
Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.
Kanagawa, 2003, Bias and artifacts in multitemplate polymerase chain reactions (PCR), Journal of Bioscience and Bioengineering, 96(4):317-323.
Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.
Kinde et al., Jun. 7, 2011, Detection and quantification of rare mutations with massively parallel sequencing, Proc. Natl Acad Sci, 108(23):9530-0535.
Kivioja et al., Jan. 2012, Counting absolute numbers of molecules using unique molecular identifiers. Nature Methods, 9(1):72-76.
Koboldt et al., Sep. 1, 2009, VarScan: variant detection in massively parallel sequencing of individual and pooled samples. Bioinformatics. 25(17):2283-2285.
Konig et al., Jul. 2010, iCLIP reveals the function of hnRNAP particles in splicing at individual nucleotide resolution, Nature Structural & Molecular Biology, 17(7):909-916.
Larson et al., Nov. 2009, A single molecule view of of gene expression. Trends Cell Biol. 19(11):630-637.
Leamon et al., Nov. 2003, A massively parallel PicoTiterPlate based platform for discrete picoliter-scale polymerase chain reactions, Electrophoresis, 24(21):3769-3777.
Lee et al., Mar. 21, 2014, Highly multiplexed subcellular RNA sequencing in situ. Science. 343(6177):1360-1363.
Lizardi et al., Jul. 1998, Mutation detection and single-molecule counting using isothermal rolling-circle amplification. Nat Genet. 19(3):225-32.
Lockhart et al., 1996, Expression monitoring by hybridization to high-density oligonucleotide arrays. Nature Biotechnology, 14:1675-1680.
Lovatt et al., Feb. 2014, Transcriptome in vivo analysis (TIVA) of spatially defined single cells in live tissue. Nat Methods. 11(2):190-196.
Lucito et al., 1996, Representational Oligonucleotide Microarray Analysis: A High-Resolution Method to Detect Genome Copy Number Variation. Genome Research, 13: 2291-2305.
Maamar et al., 2007, Noise in Gene Expression Determines Cell Fate in Bacillus subtilis. Science, 317:526-529.
Macaulay et al., 2015, G&T-seq: parallel sequencing of single-cell genomes and transcriptomes. Nature Methods, pp. 1-7.
Macosko et al., 2015, Highly parallel genome-wide expression profiling of individual cells using nanoliter droplets, Cell 161:1202-1214 (and supplemental information).
Makrigiorgos et al., Sep. 2002, A PCR-Based amplification method retaining quantative difference between two complex genomes. Nature Biotech, 20(9):936-939.
Margulies et al., Sep. 15, 2005 Genome sequencing in microfabricated high-density picolitre reactors, Nature, 437:376-380.
McCloskey et al., Dec. 2007, Encoding PCR products with batch-stamps and barcodes. Biochem Genet. 45(11-12):761-767.

Medvedev et al., Nov. 2010, Detecting copy number variation with mated short reads. Genome Res. 20(11):1613-1622.
Mei et al., Mar. 22, 2010, Identification of recurrent regions of Copy-Number Variants across multiple individuals. BMC Bioinformatics. 11:147.
Merriam-Webster, definition of associate,: http://www.merriam-webster.com/dictionary/associate, accessed Apr. 5, 2016.
Miller et al., 2006, Directed evolution by in vitro compartmentalization, Nature Methods, 3:561-570.
Miner et al., 2004, Molecular barcodes detect redundancy and contamination in hairpin-bisulfite PCR, Nucleic Acids Research, 32(17):e135.
Mortazavi et al., 2008, Mapping and quantifying mammalian transcriptomes by RNA-Seq. Nat. Methods. 5:621-628.
Newell et al., Jan. 27, 2012, Cytometry by time-of-flight shows combinatorial cytokine expression and virus-specific cell niches within a continuum of CD8+ T cell phenotypes. Immunity. 36(1):142-152.
Novak et al., Jan. 20, 2011, Single-cell multiplex gene detection and sequencing with microfluidically generated agarose emulsions, Angew Chem Int Ed Engl., 50(2):390-395.
Ogino et al., Nov. 2002, Quantification of PCR bias caused by a single nucleotide polymorphism in SMN gene dosage analysis. J Mol Diagn. 4(4):185-190.
Parameswaran et al., 2007, A pyrosequencing-tailored nucleotide barcode design unveils opportunities for large-scale sample multiplexing. Nucleic Acids Res. 35(19):e130.
Park et al., May 2010, Discovery of common Asian copy number variants using integrated high-resolution array CGH and massively parallel DNA sequencing. Nat Genet. 42(5):400-405.
Pihlak et al., 2008, Rapid genome sequencing with short universal tiling probes. Nature Biotechnology, 26:676-684.
Pinkel et al., 2005, Comparative Genomic Hybridization. Annual Review of Genomics and Human Genetics, 6:331-354.
Pleasance et al., Jan. 14, 2010, A small-cell lung cancer genome with complex signatures of tobacco exposure. Nature. 463(7278):184-190.
Plessy et al., Feb. 2013, Population transcriptomics with single-cell resolution: a new field made possible by micorfluidics: a technology for high throughput transcript counting and data-driven definition of cell types, Bioessays, 35(2):131-140.
Qiu et al., Oct. 2003, DNA sequence-based "bar codes" for tracking the origins of expressed sequence tags from a maize cDNA library constructed using multiple mRNA sources. Plant Physiol. 133(2):475-481.
Roche Diagnostics GmbH, 2006, Genome Sequencer 20 System: First to the Finish (product brochure), 40 pp.
Sasagawa et al., 2013, Quartz-Seq: a highly reproducible and sensitive single-cell RNA sequencing method, reveals non-genetic gene-expression heterogeneity. Genome Biology, 14:R31.
Sasuga et al., Dec. 2008, Single-cell chemical lysis method for analyses of intracellular molecules using an array of picoliter-scale microwells, Anal Chem, 80(23):9141-9149.
Satija et al., May 2015, Spatial reconstruction of single-cell gene expression data. Nature Biotechnology, 33(5):495-508.
Schmitt et al., Sep. 4, 2012, Detection of ultra-rare mutations by next-generation sequencing. Proc Natl Acad Sci U S A. 109(36):14508-14513.
Sebat et al., 2004, Large-Scale Copy Number Polymorphism in the Human Genome. Science, 305:525-528.
Shalek et al., Jun. 13, 2013, Single-cell transcriptomics reveals bimodality in expression and splicing in immune cells. Nature. 498(7453):236-240.
Shiroguchi et al., Jan. 24, 2012, Digital RNA sequencing minimizes sequence-dependent bias and amplification noise with optimized single-molecule barcodes. Proc Natl Acad Sci U S A. 109(4):1347-1352.
Shoemaker et al., 1996, Quantitative phenotypic analysis of yeast deletion mutants using a highly parallel molecular bar-coding strategy. Nature Genetics, 14:450-456.
Simpson et al., Feb. 15, 2010, Copy Number variant detection in inbred strains from short read sequence data. Bioinformatics. 26(4):565-567.

(56) References Cited

OTHER PUBLICATIONS

Smith et al., 2010, Highly-multiplexed barcode sequencing: an efficient method for parallel analysis of pooled samples. Nucleic Acids Research, 38(13):e142.
Tan et al., Apr. 2013, Genome-wide comparison of DNA hydroxymethylation in mouse embryonic stem cells and neural progenitor cells by a new comparative hMeDIP-seq method. Nucleic Acids Res. 41(7):e84.
Taudien et al., Apr. 19, 2010, Haplotyping and copy number estimation of the highly polymorphic human beta-defensin locus on 8p23 by 454 amplicon sequencing. BMC Genomics. 11:252.
The Tibbs Times, UNC bioscience newsletter, Apr. 2010, 17 pp.
Tomaz et al., Aug. 2010, Differential methylation as a cause of allele dropout at the imprinted GNAS locus. Genet Test Mol Biomarkers. 14(4):455-460.
Treutlein et al., May 15, 2014, Reconstructing lineage hierarchies of the distal lung epithelium using single-cell RNA-seq. Nature. 509(7500):371-375.
Velculescu et al., 1995, Serial Analysis of Gene Expression. Science, 270:484-487.
Velculescu et al., 1997, Characterization of the Yeast Transcriptome. Cell, 88:243-251.
Vogelstein et al., 1999, Digital PCR. Proc. Natl. Acad. Sci., 96(16):9236-9241.
Walker et al., Jan. 1, 1992, Isothermal in vitro amplification of DNA by a restriction enzyme/DNA polymerase system. Proc Natl Acad Sci U S A., 89(1):392-396.
Walsh et al., Jul. 13, 2010, Detection of inherited mutations for breast and ovarian cancer using genomic capture and massively parallel sequencing. Proc Natl Acad Sci U S A. 107(28):12629-12633.
Wang et al., 2009, RNA-Seq: a revolutionary tool for transcriptomics. Nature Reviews Genetics, 10:57-63.
Wang et al., Oct. 2010, iCLIP predicts the dual splicing effects of TIA-RNA interactions, PLoS Biol, 8(10):e1000530.
Weber et al., Sep. 15, 2003, A real-time polymerase chain reaction assay for quantification of allele ratios and correction of amplification bias. Anal Biochem. 320(2):252-258.
Wittes et al., 1999, Searching for Evidence of Altered Gene Expression: a Comment on Statistical Analysis of Microarray Data. Journal of the National Cancer Institute, 91(5):400-401.
Wodicka et al., 1997, Genome-wide expression monitoring in *Saccharomyces cerevisiae*. Nature Biotechnology, 15:1359-1367.
Wojdacz et al., May 16, 2009, Primer design versus PCR bias in methylation independent PCR amplifications. Epigenetics. 4(4):231-234.
Wood et al., Aug. 2010, Using next-generation sequencing for high resolution multiplex analysis of copy number variation from nanogram quantities of DNA from formalin-fixed paraffin-embedded specimens. Nucleic Acids Res. 38(14):e151.
Wu et al., Jan. 2014, Quantitative assessment of single-cell RNA-sequencing methods. Nat Methods. 11(1):41-46.
Yandell et al., Sep. 2011, A probabilistic disease-gene finder for personal genomes. Genome Res. 21(9):1529-1542.
Ye et al., 2001, Fluorescent microsphere-based readout technology for multiplexed human single nucleotide polymorphism analysis and bacterial identification. Human Mutation, 17(4):305-316.
Yoon et al., Sep. 2009, Sensitive and accurate detection of copy number variants using read depth of coverage. Genome Res. 19(9):1586-1592.
Zhang et al., Jun. 19, 2012, DNA-based hybridization chain reaction for amplified bioelectronic signal and ultrasensitive detection of proteins., Anal Chem., 84(12),5392-5399.
Zhang et al., Mar. 20, 2011, The impact of next-generation sequencing on genomics. J Genet Genomics. 38(3):95-109.
Zhao et al., 2005, Homozygous Deletions and Chromosome Amplifications in Human Lung Carcinomas Revealed by Single Nucleotide Polymorphism Array Analysis. Cancer Research, 65:5561-5570.
Zhou et al., 2001, Counting alleles reveals a connection between chromosome 18q loss and vascular invasion. Nature Biotechnology, 19:78-81.
Chapin et al., 2011, Rapid microRNA profiling on encoded gel microparticles, Angew. Chem. Int. Ed., 50:2289-2293.
Lee et al., May 2014, Universal process-inert encoding architecture for polymer microparticles, Nature Materials, 13:524-529.
Office action dated Oct. 3, 2013 for U.S. Appl. No. 12/969,581.
Response with allowed claims dated Mar. 4, 2014 for U.S. Appl. No. 12/969,581.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Dec. 3, 2015 for U.S. Appl. No. 14/281,706.
Office Action dated May 7, 2015 for U.S. Appl. No. 13/327,526.
Notice of allowance dated Jan. 21, 2016 for U.S. Appl. No. 13/327,526.
Office action dated Feb. 18, 2015 for U.S. Appl. No. 14/540,007.
Office action dated Sep. 24, 2015 for U.S. Appl. No. 14/540,007.
Notice of allowance dated Dec. 15, 2015 for U.S. Appl. No. 14/540,007.
Office action dated Mar. 19, 2015 for U.S. Appl. No. 14/540,018.
Office action dated Oct. 6, 2015 for U.S. Appl. No. 14/540,018.
Notice of allowance dated Dec. 21, 2015 for U.S. Appl. No. 14/540,018.
Office Action dated Feb. 26, 2015 for U.S. Appl. No. 14/540,029.
Office action dated Sep. 1, 2015 for U.S. Appl. No. 14/540,029.
International Search Report and Written Opinion dated Jun. 6, 2012 in PCT/US11/065291.
Restriction Requirement dated Mar. 15, 2016 in U.S. Appl. No. 14/381,488.
International Search Report and Written Opinion dated Sep. 6, 2013 in PCT/US13/028103.
European search report and search opinion dated Jul. 17, 2015 for EP Application No. 13755319.4.
Search and Examination Report dated Aug. 6, 2014 for GB patent application No. 1408829.8.
Search and Examination Report dated Jan. 27, 2016 in GB patent application No. 1408829.8.
Search Report and Written Opinion mailed Mar. 1, 2016 in Singapore patent application No. 1120140527W.
International search report and written opinion dated Aug. 16, 2013 for PCT/US2013/027891.
Extended European Search Report dated Dec. 15, 2015 in European patent application No. 13754428.4.
Restriction Requirement dated Mar. 17, 2016 in U.S. Appl. No. 14/472,363.
Office Action dated Apr. 11, 2016 in U.S. Appl. No. 14/472,363.
Office action dated Dec. 31, 2015 for U.S. Appl. No. 14/800,526.
Office action dated Apr. 11, 2016 for U.S. Appl. No. 14/800,526.
International Search Report and Written Opinion dated Feb. 3, 2015 in PCT/US/14/053301.
Search and Examination Report dated Aug. 26, 2015 in GB patent application No. 1511591.8.
Examination Report dated Feb. 19, 2016 in Great Britain patent application No. GB1511591.8.
International search report and written opinion dated Dec. 19, 2014 for PCT Application No. US2014/059542.
International search report and written opinion dated May 7, 2012 for PCT/IB2011/003160.
Notice of opposition dated Jul. 22, 2015 for EP Application No. 11810645.9.
Notice of opposition dated Jul. 9, 2015 for EP Application No. 11810645.9.
Bogdanova et al., Jan. 2008, Normalization of full-length enriched cDNA, Molecular Biosystems, 4(3):205.
Patanjali et al., Mar. 1991, Construction of a uniform-abundance (normalized) CNDA library, Proceedings of the National Academy of Sciences, 88(5):1943-1947.
Office Action dated Feb. 13, 2017 in U.S. Appl. No. 14/381,488.

(56) References Cited

OTHER PUBLICATIONS

Office Action dated Feb. 17, 2017 in Canadian patent application No. 2,865,575.
Third Office Action dated Dec. 27, 2016 in Chinese patent application No. 201380022187.9.
Official Action dated Dec. 28, 2016 in Japanese patent application No. 2014-558975.
Combined Search and Examination Report dated Feb. 21, 2017 in GB patent application No. 1609740.4.
Office Action dated Mar. 24, 2017 in U.S. Appl. No. 15/409,355.
International Search Report and Written Opinion dated Dec. 5, 2016 in PCT/US16/024783.
International Search Report and Written Opinion dated Jan. 31, 2017 in PCT/US16/050694.

* cited by examiner

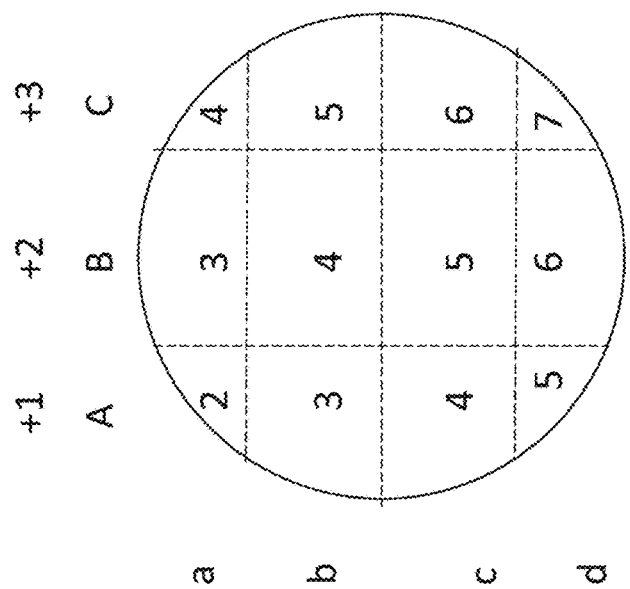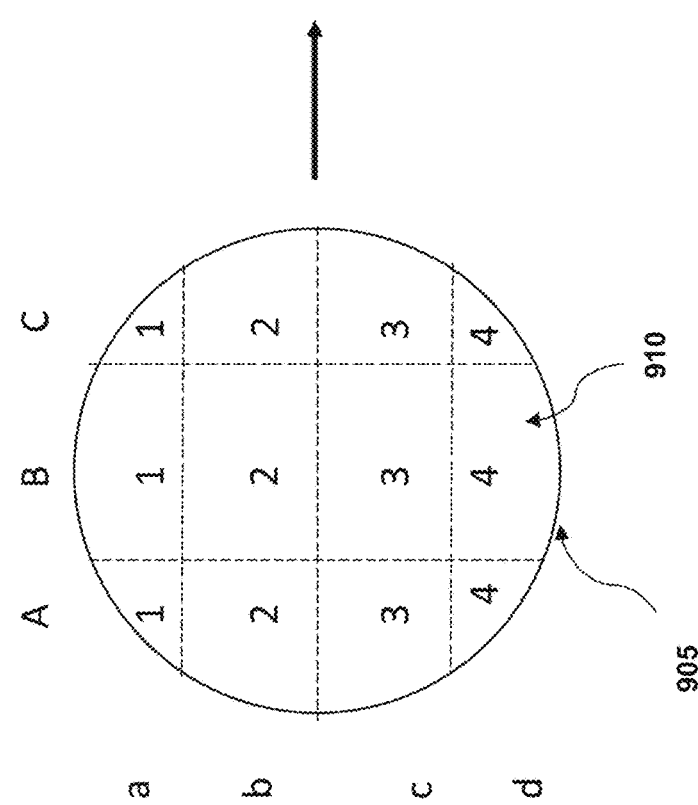
FIG. 9

| well on plate 1 | cell label part 1 oligo index | color of probe for OS1 | color of probe for OS2 | color of probe for OS3 |
|---|---|---|---|---|
| A1 | 1 | 0 | 0 | 0 |
| A2 | 2 | 0 | 0 | 1 |
| A3 | 3 | 0 | 0 | 2 |
| A4 | 4 | 0 | 0 | 3 |
| A5 | 5 | 0 | 0 | 4 |
| A6 | 6 | 0 | 1 | 0 |
| A7 | 7 | 0 | 1 | 1 |
| A8 | 8 | 0 | 1 | 2 |
| A9 | 9 | 0 | 1 | 3 |
| A10 | 10 | 0 | 1 | 4 |
| A11 | 11 | 0 | 2 | 0 |
| A12 | 12 | 0 | 2 | 1 |
| B1 | 13 | 0 | 2 | 2 |
| B2 | 14 | 0 | 2 | 3 |
| B3 | 15 | 0 | 2 | 4 |
| B4 | 16 | 0 | 3 | 0 |
| B5 | 17 | 0 | 3 | 1 |
| B6 | 18 | 0 | 3 | 2 |
| B7 | 19 | 0 | 3 | 3 |
| B8 | 20 | 0 | 3 | 4 |
| B9 | 21 | 0 | 4 | 0 |
| B10 | 22 | 0 | 4 | 1 |
| B11 | 23 | 0 | 4 | 2 |
| B12 | 24 | 0 | 4 | 3 |
| C1 | 25 | 0 | 4 | 4 |
| C2 | 26 | 1 | 0 | 0 |
| C3 | 27 | 1 | 0 | 1 |
| C4 | 28 | 1 | 0 | 2 |
| C5 | 29 | 1 | 0 | 3 |
| C6 | 30 | 1 | 0 | 4 |
| C7 | 31 | 1 | 1 | 0 |
| C8 | 32 | 1 | 1 | 1 |
| C9 | 33 | 1 | 1 | 2 |
| C10 | 34 | 1 | 1 | 3 |
| C11 | 35 | 1 | 1 | 4 |
| C12 | 36 | 1 | 2 | 0 |
| D1 | 37 | 1 | 2 | 1 |
| D2 | 38 | 1 | 2 | 2 |
| D3 | 39 | 1 | 2 | 3 |
| D4 | 40 | 1 | 2 | 4 |
| D5 | 41 | 1 | 3 | 0 |
| D6 | 42 | 1 | 3 | 1 |
| D7 | 43 | 1 | 3 | 2 |
| D8 | 44 | 1 | 3 | 3 |
| D9 | 45 | 1 | 3 | 4 |
| D10 | 46 | 1 | 4 | 0 |
| D11 | 47 | 1 | 4 | 1 |
| D12 | 48 | 1 | 4 | 2 |
| E1 | 49 | 1 | 4 | 3 |
| E2 | 50 | 1 | 4 | 4 |
| E3 | 51 | 2 | 0 | 0 |
| E4 | 52 | 2 | 0 | 1 |
| E5 | 53 | 2 | 0 | 2 |
| E6 | 54 | 2 | 0 | 3 |
| E7 | 55 | 2 | 0 | 4 |
| E8 | 56 | 2 | 1 | 0 |
| E9 | 57 | 2 | 1 | 1 |
| E10 | 58 | 2 | 1 | 2 |
| E11 | 59 | 2 | 1 | 3 |
| E12 | 60 | 2 | 1 | 4 |
| F1 | 61 | 2 | 2 | 0 |
| F2 | 62 | 2 | 2 | 1 |
| F3 | 63 | 2 | 2 | 2 |
| F4 | 64 | 2 | 2 | 3 |
| F5 | 65 | 2 | 2 | 4 |
| F6 | 66 | 2 | 3 | 0 |
| F7 | 67 | 2 | 3 | 1 |
| F8 | 68 | 2 | 3 | 2 |
| F9 | 69 | 2 | 3 | 3 |
| F10 | 70 | 2 | 3 | 4 |
| F11 | 71 | 2 | 4 | 0 |
| F12 | 72 | 2 | 4 | 1 |
| G1 | 73 | 2 | 4 | 2 |
| G2 | 74 | 2 | 4 | 3 |
| G3 | 75 | 2 | 4 | 4 |
| G4 | 76 | 3 | 0 | 0 |
| G5 | 77 | 3 | 0 | 1 |
| G6 | 78 | 3 | 0 | 2 |
| G7 | 79 | 3 | 0 | 3 |
| G8 | 80 | 3 | 0 | 4 |
| G9 | 81 | 3 | 1 | 0 |
| G10 | 82 | 3 | 1 | 1 |
| G11 | 83 | 3 | 1 | 2 |
| G12 | 84 | 3 | 1 | 3 |
| H1 | 85 | 3 | 1 | 4 |
| H2 | 86 | 3 | 2 | 0 |
| H3 | 87 | 3 | 2 | 1 |
| H4 | 88 | 3 | 2 | 2 |
| H5 | 89 | 3 | 2 | 3 |
| H6 | 90 | 3 | 2 | 4 |
| H7 | 91 | 3 | 3 | 0 |
| H8 | 92 | 3 | 3 | 1 |
| H9 | 93 | 3 | 3 | 2 |
| H10 | 94 | 3 | 3 | 3 |
| H11 | 95 | 3 | 3 | 4 |
| H12 | 96 | 3 | 4 | 0 |

0: no fluorophore
1: fluorophore 1
2: fluorophore 2
3: fluorophore 3
4: fluorophore 4

| well on plate 2 | cell label part 2 oligo index | color of probe for OS4 | color of probe for OS5 | color of probe for OS6 |
|---|---|---|---|---|
| A1 | 1 | 0 | 0 | 0 |
| A2 | 2 | 0 | 0 | 1 |
| A3 | 3 | 0 | 0 | 2 |
| A4 | 4 | 0 | 0 | 3 |
| A5 | 5 | 0 | 0 | 4 |
| A6 | 6 | 0 | 1 | 0 |
| A7 | 7 | 0 | 1 | 1 |
| A8 | 8 | 0 | 1 | 2 |
| A9 | 9 | 0 | 1 | 3 |
| A10 | 10 | 0 | 1 | 4 |
| A11 | 11 | 0 | 2 | 0 |
| A12 | 12 | 0 | 2 | 1 |
| B1 | 13 | 0 | 2 | 2 |
| B2 | 14 | 0 | 2 | 3 |
| B3 | 15 | 0 | 2 | 4 |
| B4 | 16 | 0 | 3 | 0 |
| B5 | 17 | 0 | 3 | 1 |
| B6 | 18 | 0 | 3 | 2 |
| B7 | 19 | 0 | 3 | 3 |
| B8 | 20 | 0 | 3 | 4 |
| B9 | 21 | 0 | 4 | 0 |
| B10 | 22 | 0 | 4 | 1 |
| B11 | 23 | 0 | 4 | 2 |
| B12 | 24 | 0 | 4 | 3 |
| C1 | 25 | 0 | 4 | 4 |
| C2 | 26 | 1 | 0 | 0 |
| C3 | 27 | 1 | 0 | 1 |
| C4 | 28 | 1 | 0 | 2 |
| C5 | 29 | 1 | 0 | 3 |
| C6 | 30 | 1 | 0 | 4 |
| C7 | 31 | 1 | 1 | 0 |
| C8 | 32 | 1 | 1 | 1 |
| C9 | 33 | 1 | 1 | 2 |
| C10 | 34 | 1 | 1 | 3 |
| C11 | 35 | 1 | 1 | 4 |
| C12 | 36 | 1 | 2 | 0 |

| well on plate 2 | cell label part 2 oligo index | color of probe for OS4 | color of probe for OS5 | color of probe for OS6 |
|---|---|---|---|---|
| D1 | 37 | 1 | 2 | 1 |
| D2 | 38 | 1 | 2 | 2 |
| D3 | 39 | 1 | 2 | 3 |
| D4 | 40 | 1 | 2 | 4 |
| D5 | 41 | 1 | 3 | 0 |
| D6 | 42 | 1 | 3 | 1 |
| D7 | 43 | 1 | 3 | 2 |
| D8 | 44 | 1 | 3 | 3 |
| D9 | 45 | 1 | 3 | 4 |
| D10 | 46 | 1 | 4 | 0 |
| D11 | 47 | 1 | 4 | 1 |
| D12 | 48 | 1 | 4 | 2 |
| E1 | 49 | 1 | 4 | 3 |
| E2 | 50 | 1 | 4 | 4 |
| E3 | 51 | 2 | 0 | 0 |
| E4 | 52 | 2 | 0 | 1 |
| E5 | 53 | 2 | 0 | 2 |
| E6 | 54 | 2 | 0 | 3 |
| E7 | 55 | 2 | 0 | 4 |
| E8 | 56 | 2 | 1 | 0 |
| E9 | 57 | 2 | 1 | 1 |
| E10 | 58 | 2 | 1 | 2 |
| E11 | 59 | 2 | 1 | 3 |
| E12 | 60 | 2 | 1 | 4 |
| F1 | 61 | 2 | 2 | 0 |
| F2 | 62 | 2 | 2 | 1 |
| F3 | 63 | 2 | 2 | 2 |
| F4 | 64 | 2 | 2 | 3 |
| F5 | 65 | 2 | 2 | 4 |
| F6 | 66 | 2 | 3 | 0 |
| F7 | 67 | 2 | 3 | 1 |
| F8 | 68 | 2 | 3 | 2 |
| F9 | 69 | 2 | 3 | 3 |
| F10 | 70 | 2 | 3 | 4 |
| F11 | 71 | 2 | 4 | 0 |
| F12 | 72 | 2 | 4 | 1 |

| well on plate 2 | cell label part 2 oligo index | color of probe for OS4 | color of probe for OS5 | color of probe for OS6 |
|---|---|---|---|---|
| G1 | 73 | 2 | 4 | 2 |
| G2 | 74 | 2 | 4 | 3 |
| G3 | 75 | 2 | 4 | 4 |
| G4 | 76 | 3 | 0 | 0 |
| G5 | 77 | 3 | 0 | 1 |
| G6 | 78 | 3 | 0 | 2 |
| G7 | 79 | 3 | 0 | 3 |
| G8 | 80 | 3 | 0 | 4 |
| G9 | 81 | 3 | 1 | 0 |
| G10 | 82 | 3 | 1 | 1 |
| G11 | 83 | 3 | 1 | 2 |
| G12 | 84 | 3 | 1 | 3 |
| H1 | 85 | 3 | 1 | 4 |
| H2 | 86 | 3 | 2 | 0 |
| H3 | 87 | 3 | 2 | 1 |
| H4 | 88 | 3 | 2 | 2 |
| H5 | 89 | 3 | 2 | 3 |
| H6 | 90 | 3 | 2 | 4 |
| H7 | 91 | 3 | 3 | 0 |
| H8 | 92 | 3 | 3 | 1 |
| H9 | 93 | 3 | 3 | 2 |
| H10 | 94 | 3 | 3 | 3 |
| H11 | 95 | 3 | 3 | 4 |
| H12 | 96 | 3 | 4 | 0 |

FIG. 26

0: no fluorophore
1: fluorophore 1
2: fluorophore 2
3: fluorophore 3
4: fluorophore 4

| well on plate 3 | cell label part 3 oligo index | color of probe for OS7 | color of probe for OS8 | color of probe for OS9 |
|---|---|---|---|---|
| A1 | 1 | 0 | 0 | 0 |
| A2 | 2 | 0 | 0 | 1 |
| A3 | 3 | 0 | 0 | 2 |
| A4 | 4 | 0 | 0 | 3 |
| A5 | 5 | 0 | 0 | 4 |
| A6 | 6 | 0 | 1 | 0 |
| A7 | 7 | 0 | 1 | 1 |
| A8 | 8 | 0 | 1 | 2 |
| A9 | 9 | 0 | 1 | 3 |
| A10 | 10 | 0 | 1 | 4 |
| A11 | 11 | 0 | 2 | 0 |
| A12 | 12 | 0 | 2 | 1 |
| B1 | 13 | 0 | 2 | 2 |
| B2 | 14 | 0 | 2 | 3 |
| B3 | 15 | 0 | 2 | 4 |
| B4 | 16 | 0 | 3 | 0 |
| B5 | 17 | 0 | 3 | 1 |
| B6 | 18 | 0 | 3 | 2 |
| B7 | 19 | 0 | 3 | 3 |
| B8 | 20 | 0 | 3 | 4 |
| B9 | 21 | 0 | 4 | 0 |
| B10 | 22 | 0 | 4 | 1 |
| B11 | 23 | 0 | 4 | 2 |
| B12 | 24 | 0 | 4 | 3 |
| C1 | 25 | 0 | 4 | 4 |
| C2 | 26 | 1 | 0 | 0 |
| C3 | 27 | 1 | 0 | 1 |
| C4 | 28 | 1 | 0 | 2 |
| C5 | 29 | 1 | 0 | 3 |
| C6 | 30 | 1 | 0 | 4 |
| C7 | 31 | 1 | 1 | 0 |
| C8 | 32 | 1 | 1 | 1 |
| C9 | 33 | 1 | 1 | 2 |
| C10 | 34 | 1 | 1 | 3 |
| C11 | 35 | 1 | 1 | 4 |
| C12 | 36 | 1 | 2 | 0 |

| well on plate 3 | cell label part 3 oligo index | color of probe for OS7 | color of probe for OS8 | color of probe for OS9 |
|---|---|---|---|---|
| D1 | 37 | 1 | 2 | 1 |
| D2 | 38 | 1 | 2 | 2 |
| D3 | 39 | 1 | 2 | 3 |
| D4 | 40 | 1 | 2 | 4 |
| D5 | 41 | 1 | 3 | 0 |
| D6 | 42 | 1 | 3 | 1 |
| D7 | 43 | 1 | 3 | 2 |
| D8 | 44 | 1 | 3 | 3 |
| D9 | 45 | 1 | 3 | 4 |
| D10 | 46 | 1 | 4 | 0 |
| D11 | 47 | 1 | 4 | 1 |
| D12 | 48 | 1 | 4 | 2 |
| E1 | 49 | 1 | 4 | 3 |
| E2 | 50 | 1 | 4 | 4 |
| E3 | 51 | 2 | 0 | 0 |
| E4 | 52 | 2 | 0 | 1 |
| E5 | 53 | 2 | 0 | 2 |
| E6 | 54 | 2 | 0 | 3 |
| E7 | 55 | 2 | 0 | 4 |
| E8 | 56 | 2 | 1 | 0 |
| E9 | 57 | 2 | 1 | 1 |
| E10 | 58 | 2 | 1 | 2 |
| E11 | 59 | 2 | 1 | 3 |
| E12 | 60 | 2 | 1 | 4 |
| F1 | 61 | 2 | 2 | 0 |
| F2 | 62 | 2 | 2 | 1 |
| F3 | 63 | 2 | 2 | 2 |
| F4 | 64 | 2 | 2 | 3 |
| F5 | 65 | 2 | 2 | 4 |
| F6 | 66 | 2 | 3 | 0 |
| F7 | 67 | 2 | 3 | 1 |
| F8 | 68 | 2 | 3 | 2 |
| F9 | 69 | 2 | 3 | 3 |
| F10 | 70 | 2 | 3 | 4 |
| F11 | 71 | 2 | 4 | 0 |
| F12 | 72 | 2 | 4 | 1 |

| well on plate 3 | cell label part 3 oligo index | color of probe for OS7 | color of probe for OS8 | color of probe for OS9 |
|---|---|---|---|---|
| G1 | 73 | 2 | 4 | 2 |
| G2 | 74 | 2 | 4 | 3 |
| G3 | 75 | 2 | 4 | 4 |
| G4 | 76 | 3 | 0 | 0 |
| G5 | 77 | 3 | 0 | 1 |
| G6 | 78 | 3 | 0 | 2 |
| G7 | 79 | 3 | 0 | 3 |
| G8 | 80 | 3 | 0 | 4 |
| G9 | 81 | 3 | 1 | 0 |
| G10 | 82 | 3 | 1 | 1 |
| G11 | 83 | 3 | 1 | 2 |
| G12 | 84 | 3 | 1 | 3 |
| H1 | 85 | 3 | 1 | 4 |
| H2 | 86 | 3 | 2 | 0 |
| H3 | 87 | 3 | 2 | 1 |
| H4 | 88 | 3 | 2 | 2 |
| H5 | 89 | 3 | 2 | 3 |
| H6 | 90 | 3 | 2 | 4 |
| H7 | 91 | 3 | 3 | 0 |
| H8 | 92 | 3 | 3 | 1 |
| H9 | 93 | 3 | 3 | 2 |
| H10 | 94 | 3 | 3 | 3 |
| H11 | 95 | 3 | 3 | 4 |
| H12 | 96 | 3 | 4 | 0 |

SPATIALLY ADDRESSABLE MOLECULAR BARCODING

RELATED APPLICATIONS

The present application claims priority under 35 U.S.C. §119(e) to U.S. Provisional Application No. 62/126,230, filed on Feb. 27, 2015, and U.S. Provisional Application No. 62/162,471, filed on May 15, 2015. The content of these related applications is herein expressly incorporated by reference in its entirety.

BACKGROUND

Field

The present disclosure relates generally to the field of molecular biology and more particularly to molecular barcoding.

Description of the Related Art

Methods and techniques such as in situ hybridization and immunohistochemistry allow the visualization of the locations of target molecules within the sample. Methods and techniques for labeling target molecules for amplification and sequencing, for example stochastic barcoding, are useful for determining the identities of the target molecules. Determining the identities and locations of the targets molecules in the sample is important for clinical applications, diagnostics, and biomedical research. Thus, there is a need for methods and techniques capable of correlating the identities of the target molecules with the locations of target molecules within the sample.

SUMMARY

Disclosed herein are methods for determining the number and spatial locations of a plurality of targets in a sample. In some embodiment, the methods include: stochastically barcoding the plurality of targets in the sample using a plurality of stochastic barcodes, wherein each of the plurality of stochastic barcodes comprises a spatial label and a molecular label; estimating the number of each of the plurality of targets using the molecular label; and identifying the spatial location of each of the plurality of targets using the spatial label. The method can be multiplexed.

In some embodiments, stochastically barcoding the plurality of targets in the sample can include hybridizing the plurality of stochastic barcodes with the plurality of targets to generate stochastically barcoded targets, and at least one of the plurality of targets is hybridized to one of the plurality of stochastic barcodes. Stochastically barcoding the plurality of targets in the sample can include comprises generating an indexed library of the stochastically barcoded targets. The molecular labels of different stochastic barcodes can be different from one another. The sample can be physically divided or is intact during stochastically barcoding the plurality of targets in the sample. The spatial locations of the plurality of targets in the sample can be on a surface of the sample, inside the sample, subcellularly in the sample, or any combination thereof. Stochastic barcoding the plurality of targets in the sample can be performed on the surface of the sample, subcellularly in the sample, inside the sample, or any combination thereof.

In some embodiments, the spatial label can include 5-20 nucleotides. The molecular label can include 5-20 nucleotides. Estimating the number of the plurality of targets using the molecular label can include determining sequences of the spatial labels and molecular labels of the plurality of the stochastic labels and counting the number of the molecular labels with distinct sequences. Determining the sequences of the spatial labels and the molecular labels of the plurality of the stochastic barcodes can include sequencing some or all of the plurality of stochastic barcodes. Sequencing some or all of the plurality of stochastic barcodes can include generating sequences each with a read length of 100 or more bases. Identifying the spatial locations of the plurality of targets can include correlating the spatial labels of the plurality of the stochastic barcodes with the spatial locations of the plurality of targets in the sample.

In some embodiments, the methods can include comprising visualizing the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after stochastically barcoding the plurality of targets in the sample. In some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, the sample can include a plurality of cells and the plurality of targets can be associated with the plurality of cells. The plurality of cells can include one or more cell types. At least one of the one or more cell types can be brain cell, heart cell, cancer cell, circulating tumor cell, organ cell, epithelial cell, metastatic cell, benign cell, primary cell, circulatory cell, or any combination thereof. The plurality of targets can include ribonucleic acids (RNAs), messenger RNAs (mRNAs), microRNAs, small interfering RNAs (siRNAs), RNA degradation products, RNAs each comprising a poly(A) tail, and any combination thereof. Stochastically barcoding the plurality of targets in the sample can be performed with a solid support including the plurality of stochastic barcodes. In some embodiments, the methods can include decoding the solid support. The solid support can include a plurality of synthetic particles associated with the plurality of stochastic barcodes. The spatial labels of the plurality of stochastic barcodes on different solid supports can differ by at least one nucleotide.

In some embodiments, each of the plurality of stochastic barcodes can include one or more of a universal label and a cellular label, wherein universal labels can be the same for the plurality of stochastic barcodes on the solid support and cellular labels can be the same for the plurality of stochastic barcodes on the solid support. The universal label can include 5-20 nucleotides. The cellular label can include 5-20 nucleotides. The solid support can include the plurality of stochastic barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. Solid support can include a polymer, a matrix, a hydrogel, a needle array device, an antibody, or any combination thereof.

Disclosed herein are methods for determining spatial locations of a plurality of targets in a sample. In some embodiments, the methods include: stochastically barcoding the plurality of targets in the sample at one or more time points using a plurality of stochastic barcodes, wherein each of the plurality of stochastic barcodes comprises a spatial label; and identifying the spatial location of each of the plurality of targets using the spatial label.

In some embodiments, stochastically barcoding the plurality of targets in the sample using the plurality of stochastic barcodes can include stochastically barcoding the plurality of targets in the sample at different time points using the plurality of stochastic barcodes. Each of the plurality of stochastic barcodes can include a dimension label, and the dimension labels of the plurality of stochastic barcodes used for stochastic barcoding the plurality of targets at the different time points can be different. The dimension labels can correlate with the different time points.

In some embodiments, stochastically barcoding the plurality of targets in the sample can include contacting the sample with a device. The device can be a needle, a needle array, a tube, a suction device, an injection device, an electroporation device, a fluorescent activated cell sorter device, a microfluidic device, or any combination thereof. The device can contact sections of the sample at a specified rate. The specified rate can correlate the spatial locations of the plurality of targets with the one or more time points. Stochastically barcoding the plurality of targets in the sample can be performed with a solid support including a plurality of synthetic particles associated with the plurality of stochastic barcodes.

Disclosed herein are synthetic particles. In some embodiments, each synthetic particle, include: a plurality of stochastic barcodes, wherein each of the plurality of stochastic barcodes comprises a cellular label and a molecular label; a first group of optical labels; a second group of optical labels, wherein each optical label in the first group of optical labels comprises a first optical moiety and each optical label in the second group of optical labels comprises a second optical moiety, and wherein each of the plurality of synthetic particles is associated with an optical barcode comprising the first optical moiety and the second optical moiety.

In some embodiments, the molecular labels of the plurality of stochastic barcodes are different from one another, and the molecular labels are selected from a group comprising at least 100 molecular labels with unique sequences. The cellular labels of the plurality of stochastic barcodes can be same. The first optical moiety and the second optical moiety are selected from a group comprising two or more spectrally-distinct optical moieties. Each of the plurality of stochastic barcodes can include a spatial label, wherein the spatial labels of the plurality of stochastic barcodes differ from one another by at least one nucleotide.

In some embodiments, each of the plurality of stochastic barcodes further comprises a universal label, wherein universal labels of all stochastic barcodes on the particle are the same. The synthetic particle can be a bead or a magnetic bead. The bead can be a silica gel bead, a controlled pore glass beads, a magnetic beads, a Dynabead, a Sephadex/Sepharose bead, a cellulose beads, a polystyrene bead, or any combination thereof.

Disclosed herein are methods for determining spatial locations of a plurality of targets in a sample. In some embodiments, the methods include: stochastically barcoding the plurality of targets in the sample using a plurality of stochastic barcodes, wherein each of the plurality of stochastic barcodes comprises a pre-spatial label; concatenating one or more spatial label blocks onto the pre-spatial label to generate a spatial label; and identifying the spatial location of each of the plurality of targets using the spatial label.

In some embodiments, stochastically barcoding the plurality of targets in the sample can include hybridizing the plurality of stochastic barcodes with the plurality of targets to generate stochastically barcoded targets, and at least one of the plurality of targets is hybridized to one of the plurality of stochastic barcodes. Stochastically barcoding the plurality of targets in the sample can include generating an indexed library of the stochastically barcoded targets. The spatial label can include 5-20 nucleotides. The sample can include a plurality of cells and the plurality of targets that can be associated with the plurality of cells. The plurality of targets can include ribonucleic acids (RNAs), messenger RNAs (mRNAs), microRNAs, small interfering RNAs (siRNAs), RNA degradation products, RNAs each comprising a poly (A) tail, and any combination thereof. Stochastically barcoding the plurality of targets in the sample can be performed with a solid support comprising the plurality of stochastic barcodes. In some embodiments, the methods can include decoding the solid support. The solid support can include a plurality of synthetic particles associated with the plurality of stochastic barcodes. The synthetic particles can be beads.

Disclosed herein can be methods for determining spatial locations of a plurality of targets in a sample. In some embodiments, the methods include: imaging the sample to generate a sample image; stochastically barcoding the plurality of targets in the sample using a plurality of stochastic barcodes to generate stochastically barcoded targets, wherein each of the plurality of stochastic barcodes can include a spatial label; and identifying the spatial location of each of the plurality of targets using the spatial label.

In some embodiments, identifying the spatial location of each of the plurality of targets using the spatial label can include correlating the sample image with the spatial labels of the plurality of targets in the sample. Imaging the sample can include staining the sample with a stain, wherein the stain can be a fluorescent stain, a negative stain, an antibody stain, or any combination thereof. Imaging the sample can include imaging the sample using optical microscopy, electron microscopy, confocal microscopy, fluorescence microscopy, or any combination thereof.

In some embodiments, the sample can include a tissue, a cell monolayer, fixed cells, a tissue section, or any combination thereof. Correlating the sample image with the spatial labels of the plurality of targets in the sample can include overlaying the sample image with the spatial labels of the plurality of targets in the sample. The sample can include a biological sample, a clinical sample, an environmental sample, a biological fluid, a tissue, or a cell from a subject. The subject can be a human, a mouse, a dog, a rat, or a vertebrate.

In some embodiments, the methods can include determining genotype, phenotype, or one or more genetic mutations of the subject based on the spatial labels of the plurality of targets in the sample. In some embodiments, the methods can include predicting susceptibility of the subject to one or more diseases. At least one of the one or more diseases can be cancer or a hereditary disease. The sample can include a plurality of cells and the plurality of targets can be associated with the plurality of cells. The plurality of cells can include one or more cell types. In some embodiments, the methods can include determining cell types of the plurality of cells in the sample. The drug can be chosen based on predicted responsiveness of the cell types of the plurality of cells in the sample.

Disclosed herein are methods for determining spatial locations of a plurality of singles cells. In some embodiments, the methods can include: stochastically barcoding the plurality of singe cells using a plurality of synthetic particles, wherein each of the plurality of synthetic particles can include a plurality of stochastic barcodes, a first group of optical labels, and a second group of optical labels, wherein each of the plurality of stochastic barcodes can include a cellular label and a molecular label, wherein each optical label in the first group of optical labels can include a first optical moiety and each optical label in the second group of optical labels can include a second optical moiety, and wherein each of the plurality of synthetic particles can be associated with an optical barcode including the first optical moiety and the second optical moiety; detecting the optical barcode of each of the plurality of synthetic particles to determine the location of each of the plurality of synthetic particles; and determining the spatial locations of the plurality of single cells based on the locations of the plurality of synthetic particles.

In some embodiments, stochastically barcoding the plurality of single cells using the plurality of synthetic particles can include contacting the plurality of single cells with the plurality of synthetic particles, and each of the plurality of synthetic particles can be in close proximity to a single cell or a small number of cells. Each of the plurality of single cells can include a plurality of targets, and stochastically barcoding the plurality of single cells can include hybridizing the plurality of stochastic barcodes with the plurality of targets to generate stochastically barcoded targets, and at least one of the plurality of targets can be hybridized to one of the plurality of stochastic barcodes.

In some embodiments, the cellular labels of the plurality of stochastic barcodes on one synthetic particle can have the same sequence and the cellular labels of the plurality of stochastic barcodes on different synthetic particles can have different sequences. The molecular labels of the plurality of stochastic barcodes on one synthetic barcode can be different from one another, and the molecular labels can be selected from a group including at least 100 molecular labels with unique sequences. The first optical moiety and the second optical moiety can be selected from a group including two or more spectrally-distinct optical moieties. Determining the optical barcodes of the plurality of synthetic particles and determining the optical barcodes of the plurality of synthetic particles can include generating an optical image showing the optical barcodes and the locations of the plurality of synthetic particles.

In some embodiments, the plurality of single cells can include cells distributed across a well array including wells, and each of a majority of the wells in the well array contains at most one single cell. In some embodiments, the methods can include lysing the plurality of single cells; and generating an indexed library of stochastically barcoded targets, wherein each of the stochastically barcoded targets can include a cellular label sequence, a molecular label sequence, and at least a portion of the complementary sequence of one of the plurality of targets. The methods can include amplifying the stochastically barcoded targets of the indexed library to generate amplified stochastically barcoded targets; and sequencing the amplified stochastically barcoded targets to determine the number of amplified stochastically barcoded targets with unique molecular label sequences and identical complementary sequence, wherein the number of amplified stochastically barcoded targets with unique molecular label sequences and identical complementary sequence can be substantially the same as the occurrences of targets with sequences complementary of the identical complementary sequence in the single cell or the small number of cells. The plurality of cells can include a tissue, a cell monolayer, fixed cells, a tissue section, or any combination thereof. Amplifying the labeled target molecules can include bridge amplification, amplification with a gene specific primer, a universal primer, an oligo(dT) primer, or any combination thereof.

Disclosed herein are methods for identifying distinct cells in two or more samples. In some embodiments, the methods can include: stochastically barcoding a plurality of targets in the two or more samples using a plurality of stochastic barcodes, wherein each of the plurality of stochastic barcodes can include a spatial label and a molecular label; estimating the number of the plurality of targets in the two or more samples using the molecular label; and distinguishing the two or more samples from each other using the spatial label, wherein the plurality of targets associated with stochastic barcodes with different spatial labels can be from different samples.

In some embodiments, stochastically barcoding the plurality of targets in the two or more samples can include hybridizing the plurality of stochastic barcodes with the plurality of targets to generate stochastically barcoded targets, and at least one of the plurality of targets can be hybridized to one of the plurality of stochastic barcodes. Stochastically barcoding the plurality of targets in the two or more samples can include generating an indexed library of the stochastically barcoded targets. The spatial label can include 5-20 nucleotides. The molecular label can include 5-20 nucleotides. Each of the two or more samples can include a plurality of cells and the plurality of targets can be associated with the plurality of cells. The plurality of targets can include ribonucleic acids (RNAs), messenger RNAs (mRNAs), microRNAs, small interfering RNAs (siRNAs), RNA degradation products, RNAs each including a poly(A) tail, and any combination thereof. Stochastically barcoding the plurality of targets in the two or more samples can be performed with a solid support including a plurality of synthetic particles associated with the plurality of stochastic barcodes. The synthetic particles can be beads. The beads can be silica gel beads, controlled pore glass beads, magnetic beads, Dynabeads, Sephadex/Sepharose beads, cellulose beads, polystyrene beads, or any combination thereof.

Disclosed herein are kits for determining the number and spatial locations of a plurality of targets in a sample. In some embodiments, the kits can include: a plurality of stochastic barcodes, wherein each of the plurality of stochastic barcodes can include a spatial label, wherein the spatial labels of the plurality of stochastic barcodes differ from one another by at least one nucleotide; and instructions for using the plurality of stochastic barcodes. The plurality of stochastic barcodes can be associated with a solid support. The solid support can include a plurality of synthetic particles associated with the plurality of synthetic particles.

In some embodiments, each of the plurality of synthetic particles can include a first group of optical labels and a second group of optical labels, and each optical label in the first group of optical labels can include a first optical moiety, each optical label in the second group of optical labels can include a second optical moiety, and the first optical moiety and the second optical moiety can be selected from a group including two or more spectrally-distinct optical moieties. Each of the plurality of stochastic barcodes can include one or more of a molecular label, a universal label, and a cellular label, wherein universal labels and cellular labels of all stochastic barcodes on the solid support can be the same.

In some embodiments, the solid support can include the plurality of stochastic barcodes in two dimensions or three dimensions. The plurality of synthetic particles can be beads. The beads can be silica gel beads, controlled pore glass beads, magnetic beads, Dynabeads, Sephadex/Sepharose beads, cellulose beads, polystyrene beads, or any combination thereof. The synthetic particles can be magnetic beads. The solid support can include a polymer, a matrix, a hydrogel, a needle array device, an antibody, or any combination thereof. In some embodiments, the kits can include a buffer. The kits can include a cartridge. The solid support can be pre-loaded on a substrate. The kits can include one or more reagents for a reverse transcription reaction. The kits can include one or more reagents for an amplification reaction.

BRIEF DESCRIPTION OF THE DRAWINGS

FIG. 9 shows a non-limiting exemplary embodiment for determining spatial locations of targets in a sample using label lithography.

FIG. 20 is a lookup table showing the oligonucleotide content in each of the 96 wells in the first plate.

FIG. 23 is a lookup table showing the oligonucleotide content in each of the 96 wells in the second plate.

FIG. 26 is a lookup table showing the oligonucleotide content in each of the 96 wells in the third plate.

DETAILED DESCRIPTION

Figure 1:
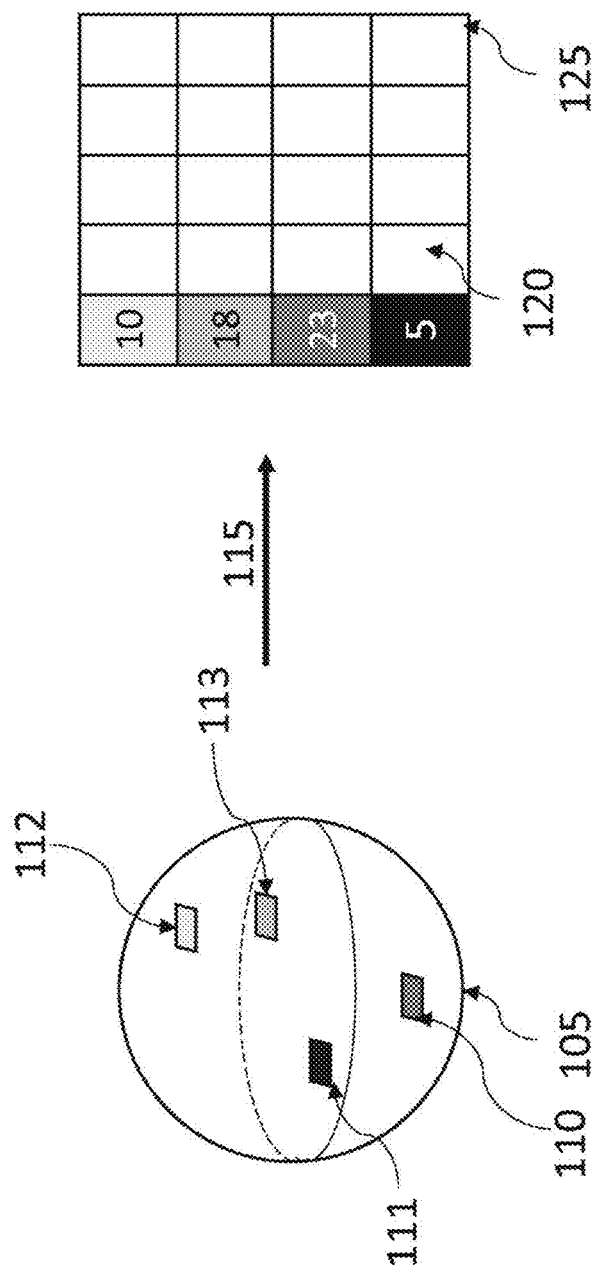
FIG. 1 shows a non-limiting exemplary embodiment for determining spatial locations of distinct targets in a sample.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

In one aspect the disclosure provides for a method for determining the number and spatial location of one or more targets in a sample comprising: contacting the spatial location in the sample with one or more stochastic barcodes, wherein each stochastic barcode comprises a spatial label and a molecular label; estimating the number of the one or more targets in the spatial location using the molecular label; and identifying the spatial location of the one or more targets using the spatial label. In some embodiments, the contacting comprises hybridizing the stochastic barcode with the one or more targets. In some embodiments, the hybridizing comprises hybridizing the one or more targets such that each of the one or more targets is hybridized to a unique stochastic barcode. In some embodiments, molecular labels of the stochastic barcodes are different. In some embodiments, the sample is physically divided during the contacting. In some embodiments, the sample is intact during the contacting. In some embodiments, the contacting is performed on the surface of the sample. In some embodiments, the contacting is performed inside the sample. In some embodiments, the contacting is performed subcellularly in the sample. In some embodiments, the spatial location is subcellular. In some embodiments, the contacting is performed on a substrate. In some embodiments, the substrate comprises the one or more stochastic barcodes in a known order. In some embodiments, the substrate comprises the one or more stochastic barcodes in an unknown order. In some embodiments, the method further comprises decoding the substrate. In some embodiments, the spatial label comprises from 5-20 nucleotides. In some embodiments, the estimating comprises generating a target-barcode molecule. In some embodiments, the target-barcode molecule comprises the sequence of a stochastic barcode to which it is associated. In some embodiments, the estimating further comprises determining the sequence of the spatial label and the molecular label. In some embodiments, the method further comprises counting occurrences of distinct sequences of the molecular label. In some embodiments, the counting is used to estimate the number of one or more targets. In some embodiments, the determining comprises sequencing the stochastic barcodes. In some embodiments, the sequencing comprises sequencing with read lengths of at least 100 bases. In some embodiments, the sequencing comprises sequencing with read lengths of at least 500 bases. In some embodiments, the identifying comprises correlating the spatial label with the spatial location in the sample. In some embodiments, the method further comprises visualizing the number of the one or more targets at the spatial location. In some embodiments, the visualizing comprises mapping the number of the one or more targets onto a map of the sample. In some embodiments, the visualizing comprises imaging the sample at a time point selected from the group consisting of: imaging the sample prior to the contacting, imaging the sample after the contacting, imaging the sample before lysing the sample, imaging the sample after lysing the sample. In some embodiments, the imaging produces an image that is used to construct a map of a physical representation of the sample. In some embodiments, the map is two dimensional. In some embodiments, the map is three dimensional. In some embodiments, the sample comprises a single cell. In some embodiments, the sample comprises a plurality of cells. In some embodiments, the plurality of cells comprises a one or more different cell types. In some embodiments, the one or more cell types are selected from the group consisting of: brain cells, heart cells, cancer cells, circulating tumor cells, organ cells, epithelial cells, metastatic cells, benign cells, primary cells, and circulatory cells, or any combination thereof. In some embodiments, the sample comprises a solid tissue. In some embodiments, the sample is obtained from a subject. In some embodiments, the subject is a subject selected from the group consisting of: a human, a mammal, a dog, a rat, a mouse, a fish, a fly, a worm, a plant, a fungus, a bacterium, a virus, a vertebrate, and an invertebrate. In some embodiments, the one or more targets are ribonucleic acid molecules. In some embodiments, the ribonucleic acid molecules are selected from the group consisting of: mRNA, microRNA, mRNA degradation products, and ribonucleic acids comprising a poly(A) tail, or any combination thereof. In some embodiments, the targets are deoxyribonucleic acid molecules. In some embodiments, the contacting is performed with a solid support. In some embodiments, the solid support can comprise a plurality of stochastic barcodes. In some embodiments, each stochastic barcode of the plurality of stochastic barcodes comprises a spatial label. In some embodiments, spatial labels on different solid supports differ by at least one nucleotide. In some embodiments, the stochastic barcode further comprises a universal label, and a cellular label. In some embodiments, the universal label and the cellular label are the same for all stochastic barcodes on the solid support. In some embodiments, the solid support comprises stochastic barcodes in two dimensions. In some embodiments, the solid support comprises stochastic barcodes in three dimensions. In some embodiments, the solid supports comprise a bead. In some embodiments, the bead is selected from the group consisting of: silica gel bead, controlled pore glass bead, magnetic bead, Dynabeads, Sephadex/Sepharose beads, cellulose beads, and polystyrene beads, or any combination thereof. In some embodiments, the bead comprises a magnetic bead. In some embodiments, the solid support is semi-solid. In some embodiments, the solid support comprises a polymer, a matrix, or a hydrogel. In some embodiments, the solid support comprises a needle array device. In some embodiments, the solid support comprises an antibody. In some embodiments the solid support comprises polystyrene.

In one aspect the disclosure provides for a method for determining spatial locations of one or more targets in a sample by timing comprising: contacting the spatial location in the sample with one or more stochastic barcodes, at one or more time points, wherein each stochastic barcode comprises a spatial label; and identifying the spatial location of the one or more targets in the sample, wherein the one or more time point correlates to the spatial location. In some embodiments, stochastic barcodes at different time points comprise different dimension labels. In some embodiments, the dimension labels correlate to the one or more times points. In some embodiments, the contacting is performed by a device. In some embodiments, the device is a device selected from the group consisting of: a needle, a needle array, a tube, a suction device, an injection device, an electroporation device, a fluorescent activated cell sorter device, and a microfluidic device, or any combination thereof. In some embodiments, the device contacts the sections at a specified rate. In some embodiments, the specified rate is used to correlate the time point with the spatial location. In some embodiments, the contacting comprises hybridizing the one or more stochastic barcodes with the one or more targets. In some embodiments, the hybridizing comprises hybridizing the one or more targets such that each of the one or more targets is hybridized to a unique stochastic barcode. In some embodiments, the one or more stochastic barcodes comprises a molecular label. In some embodiments, the molecular label is different for each of the one or more stochastic barcodes. In some embodiments, the sample is physically divided during the contacting. In some embodiments, the sample is intact during the contacting. In some embodiments, the contacting is performed on the surface of the sample. In some embodiments, the contacting is performed inside the sample. In some embodiments, the contacting is performed subcellularly in the sample. In some embodiments, the spatial location is subcellular. In some embodiments, the contacting is performed on a substrate. In some embodiments, the substrate comprises the one or more stochastic barcodes in a known order. In some embodiments, the substrate comprises the one or more stochastic barcodes in an unknown order. In some embodiments, the method further comprises decoding the substrate. In some embodiments, the spatial label comprises from 5-20 nucleotides. In some embodiments, the method further comprises estimating the number of the one or more targets using the stochastic barcode. In some embodiments, the estimating comprises generating a target-barcode molecule. In some embodiments, the target-barcode molecule comprises the sequence of a stochastic barcode to which it is associated. In some embodiments, the estimating further comprises determining the sequence of the spatial label and a molecular label. In some embodiments, the method further comprises counting occurrences of distinct sequences of the molecular label. In some embodiments, the counting is used to estimate the number of one or more targets. In some embodiments, the determining comprises sequencing the stochastic barcodes. In some embodiments, the sequencing comprises sequencing with read lengths of at least 100 bases. In some embodiments, the sequencing comprises sequencing with read lengths of at least 500 bases. In some embodiments, the identifying comprises correlating the spatial label with the spatial location in the sample. In some embodiments, the method further comprises visualizing the number of the one or more targets at the spatial location. In some embodiments, the visualizing comprises mapping the number of the one or more targets onto a map of the sample. In some embodiments, the visualizing comprises imaging the sample at a time point selected from the group consisting of: imaging the sample prior to the contacting, imaging the sample after the contacting, imaging the sample before lysing the sample, imaging the sample after lysing the sample. In some embodiments, the imaging produces an image that is used to construct a map of a physical representation of the sample. In some embodiments, the map is two dimensional. In some embodiments, the map is three dimensional. In some embodiments, the sample comprises a single cell. In some embodiments, the sample comprises a plurality of cells. In some embodiments, the plurality of cells comprises a one or more different cell types. In some embodiments, the one or more cell types are selected from the group consisting of: brain cells, heart cells, cancer cells, circulating tumor cells, organ cells, epithelial cells, metastatic cells, benign cells, primary cells, and circulatory cells, or any combination thereof. In some embodiments, the sample comprises a solid tissue. In some embodiments, the sample is obtained from a subject. In some embodiments, the subject is a subject selected from the group consisting of: a human, a mammal, a dog, a rat, a mouse, a fish, a fly, a worm, a plant, a fungus, a bacterium, a virus, a vertebrate, and an invertebrate. In some embodiments, the one or more targets are ribonucleic acid molecules. In some embodiments, the ribonucleic acid molecules are selected from the group consisting of: mRNA, microRNA, mRNA degradation products, and ribonucleic acids comprising a poly(A) tail, or any combination thereof. In some embodiments, the targets are deoxyribonucleic acid molecules. In some embodiments, the contacting is performed with a solid support. In some embodiments, the solid support comprises a plurality of stochastic barcodes. In some embodiments, each stochastic barcode of the plurality of stochastic barcodes comprises a spatial label. In some embodiments, spatial labels on different solid supports differ by at least one nucleotide. In some embodiments, the stochastic barcode further comprises a universal label, a cellular label, and a molecular label. In some embodiments, the universal label and the cellular label are the same for all stochastic barcodes on a solid support. In some embodiments, the solid supports comprise stochastic barcodes in two dimensions. In some embodiments, the solid supports comprise stochastic barcodes in three dimensions. In some embodiments, the solid supports comprise a bead. In some embodiments, the bead is selected from the group consisting of: silica gel bead, controlled pore glass bead, magnetic bead, Dynabeads, Sephadex/Sepharose beads, cellulose beads, and polystyrene beads, or any combination thereof. In some embodiments, the bead comprises a magnetic bead. In some embodiments, the solid support is semi-solid. In some embodiments, the solid support comprises a polymer, a matrix, or a hydrogel. In some embodiments, the solid support comprises a needle array device. In some embodiments, the solid support comprises an antibody.

In one aspect the disclosure provides for a method for determining the spatial location of one or more targets on a sample comprising: contacting one or more spatial locations of the sample with one or more stochastic barcodes, wherein each stochastic barcode comprises a pre-spatial label; concatenating one or more spatial label blocks onto the pre-spatial label, thereby generating a spatial label; and identifying the one or more spatial locations of the one or more targets in the sample by correlating a length of the spatial label with a spatial location in the sample. In some embodiments, spatial labels at distinct spatial locations have different lengths. In some embodiments, the contacting comprises hybridizing the stochastic barcode with the one or more targets. In some embodiments, the hybridizing comprises hybridizing the one or more targets such that each of the one or more targets is hybridized to a unique stochastic barcode. In some embodiments, the pre-spatial label comprises a molecular label. In some embodiments, the molecular label is different for each of the one or more stochastic barcodes. In some embodiments, the sample is physically divided during the contacting. In some embodiments, the sample is intact during the contacting. In some embodiments, the contacting is performed on the surface of the sample. In some embodiments, the contacting is performed inside the sample. In some embodiments, the contacting is performed subcellularly in the sample. In some embodiments, the spatial location is subcellular. In some embodiments, the contacting is performed on a substrate. In some embodiments, the substrate comprises the one or more stochastic barcodes in a known order. In some embodiments, the substrate comprises the one or more stochastic barcodes in an unknown order. In some embodiments, the method further comprises decoding the substrate. In some embodiments, the spatial label comprises from 5-20 nucleotides. In some embodiments, the method further comprises estimating the number of the distinct targets using the stochastic barcodes. In some embodiments, the estimating comprises generating a target-barcode molecule. In some embodiments, the target-barcode molecule comprises the sequence of a stochastic barcode to which it is associated. In some embodiments, the estimating further comprises determining the sequence of the spatial label and a molecular label. In some embodiments, the method further comprises counting occurrences of distinct sequences of the molecular label. In some embodiments, the counting is used to estimate the number of one or more targets. In some embodiments, the determining comprises sequencing the stochastic barcodes. In some embodiments, the sequencing comprises sequencing with read lengths of at least 100 bases. In some embodiments, the sequencing comprises sequencing with read lengths of at least 500 bases. In some embodiments, the identifying comprises correlating the spatial label with the spatial location in the sample. In some embodiments, the method further comprises visualizing the number of the one or more targets at the spatial location. In some embodiments, the visualizing comprises mapping the number of the one or more targets onto a map of the sample. In some embodiments, the visualizing comprises imaging the sample at a time point selected from the group consisting of: imaging the sample prior to the contacting, imaging the sample after the contacting, imaging the sample before lysing the sample, imaging the sample after lysing the sample. In some embodiments, the imaging produces an image that is used to construct a map of a physical representation of the sample. In some embodiments, the map is two dimensional. In some embodiments, the map is three dimensional. In some embodiments, the sample comprises a single cell. In some embodiments, the sample comprises a plurality of cells. In some embodiments, the plurality of cells comprises a one or more different cell types. In some embodiments, the one or more cell types are selected from the group consisting of:

brain cells, heart cells, cancer cells, circulating tumor cells, organ cells, epithelial cells, metastatic cells, benign cells, primary cells, and circulatory cells, or any combination thereof. In some embodiments, the sample comprises a solid tissue. In some embodiments, the sample is obtained from a subject. In some embodiments, the subject is a subject selected from the group consisting of: a human, a mammal, a dog, a rat, a mouse, a fish, a fly, a worm, a plant, a fungus, a bacterium, a virus, a vertebrate, and an invertebrate. In some embodiments, the one or more targets are ribonucleic acid molecules. In some embodiments, the ribonucleic acid molecules are selected from the group consisting of: mRNA, microRNA, mRNA degradation products, and ribonucleic acids comprising a poly(A) tail, or any combination thereof. In some embodiments, the targets are deoxyribonucleic acid molecules. In some embodiments, the contacting is performed with a solid support. In some embodiments, the solid support can comprise a plurality of stochastic barcodes. In some embodiments, each stochastic barcode of the plurality of stochastic barcodes comprises a spatial label. In some embodiments, spatial labels on different solid supports differ by at least one nucleotide. In some embodiments, the stochastic barcode further comprises a universal label, and a cellular label. In some embodiments, the universal label and the cellular label are the same for all stochastic barcodes on the solid support. In some embodiments, the solid support comprises stochastic barcodes in two dimensions. In some embodiments, the solid support comprises stochastic barcodes in three dimensions. In some embodiments, the solid support comprises a bead. In some embodiments, the bead is selected from the group consisting of: silica gel bead, controlled pore glass bead, magnetic bead, Dynabeads, Sephadex/Sepharose beads, cellulose beads, and polystyrene beads, or any combination thereof. In some embodiments, the bead comprises a magnetic bead. In some embodiments, the solid support is semi-solid. In some embodiments, the solid support comprises a polymer, a matrix, or a hydrogel. In some embodiments, the solid support comprises a needle array device. In some embodiments, the solid support comprises an antibody.

In one aspect the disclosure provides for a method for identifying distinct cells in a population of cells comprising: contacting two or more samples to a substrate, wherein the substrate comprises one or more types of stochastic barcodes, wherein each type of the types of stochastic barcodes comprises a different spatial label, and wherein each stochastic barcode comprises a molecular label; estimating the number of one or more targets in the plurality of samples using the molecular label; and distinguishing a sample from the two or more of samples by the spatial labels, wherein targets associated with different spatial labels originate from different samples. In some embodiments, the contacting comprises hybridizing the stochastic barcode with the one or more targets. In some embodiments, the hybridizing comprises hybridizing the one or more targets such that each of the one or more targets is hybridized to a unique stochastic barcode. In some embodiments, molecular labels of the stochastic barcodes are different. In some embodiments, the two or more samples are physically divided from each other during the contacting. In some embodiments, the two or more samples can be intact during the contacting. In some embodiments, the contacting is performed on the surface of the two or more samples. In some embodiments, the contacting is performed inside the two or more samples. In some embodiments, the contacting is performed subcellularly in the two or more samples. In some embodiments, the spatial location is subcellular. In some embodiments, the substrate comprises the one or more stochastic barcodes in a known order. In some embodiments, the substrate comprises the one or more stochastic barcodes in an unknown order. In some embodiments, the method further comprises decoding the substrate. In some embodiments, the spatial label comprises from 5-20 nucleotides. In some embodiments, the estimating comprises generating a target-barcode molecule. In some embodiments, the target-barcode molecule comprises the sequence of a stochastic barcode to which it is associated. In some embodiments, the estimating further comprises determining the sequence of the spatial label and the molecular label. In some embodiments, the method further comprises counting occurrences of distinct sequences of the molecular label. In some embodiments, the counting is used to estimate the number of one or more targets. In some embodiments, the determining comprises sequencing the stochastic barcodes. In some embodiments, the sequencing comprises sequencing with read lengths of at least 100 bases. In some embodiments, the sequencing comprises sequencing with read lengths of at least 500 bases. In some embodiments, the method further comprises visualizing the number of the one or more targets at the spatial location. In some embodiments, the visualizing comprises mapping the number of the one or more targets onto a map of the sample. In some embodiments, the visualizing comprises imaging the sample at a time point selected from the group consisting of: imaging the sample prior to the contacting, imaging the sample after the contacting, imaging the sample before lysing the sample, imaging the sample after lysing the sample. In some embodiments, the imaging produces an image that is used to construct a map of a physical representation of the sample. In some embodiments, the map is two dimensional. In some embodiments, the map is three dimensional. In some embodiments, the sample comprises a single cell. In some embodiments, the sample comprises a plurality of cells. In some embodiments, the plurality of cells comprises a one or more different cell types. In some embodiments, the one or more cell types are selected from the group consisting of: brain cells, heart cells, cancer cells, circulating tumor cells, organ cells, epithelial cells, metastatic cells, benign cells, primary cells, and circulatory cells, or any combination thereof. In some embodiments, the sample comprises a solid tissue. In some embodiments, the sample is obtained from a subject. In some embodiments, the subject is a subject selected from the group consisting of: a human, a mammal, a dog, a rat, a mouse, a fish, a fly, a worm, a plant, a fungus, a bacterium, a virus, a vertebrate, and an invertebrate. In some embodiments, the one or more targets are ribonucleic acid molecules. In some embodiments, the ribonucleic acid molecules are selected from the group consisting of: mRNA, microRNA, mRNA degradation products, and ribonucleic acids comprising a poly(A) tail, or any combination thereof. In some embodiments, the targets are deoxyribonucleic acid molecules. In some embodiments, the contacting is performed with a solid support. In some embodiments, the solid support comprises a plurality of stochastic barcodes. In some embodiments, each stochastic barcode of the plurality of stochastic barcodes comprises a spatial label. In some embodiments, spatial labels on different solid supports differ by at least one nucleotide. In some embodiments, the stochastic barcode further comprises a universal label, and a cellular label. In some embodiments, the universal label and the cellular label are the same for all stochastic barcodes on the solid support. In some embodiments, the solid support comprises stochastic barcodes in two dimensions. In some embodiments, the solid support comprises stochastic barcodes in three dimensions. In some embodiments, the solid support comprises a bead. In some embodiments, the bead is selected from the group consisting of: silica gel bead, controlled pore glass bead, magnetic bead, Dynabeads, Sephadex/Sepharose beads, cellulose beads, and polystyrene beads, or any combination thereof. In some embodiments, the bead comprises a magnetic bead. In some embodiments, the solid support is semi-solid. In some embodiments, the solid support comprises a polymer, a matrix, or a hydrogel. In some embodiments, the solid support comprises a needle array device. In some embodiments, the solid support comprises an antibody.

In one aspect the disclosure provides for a kit comprising: one or more types of stochastic barcodes, wherein each stochastic barcode of the one or more types of stochastic barcodes comprises a spatial label, wherein spatial labels of the one or more types of stochastic barcodes differ by at least one nucleotide; and instructions for use. In some embodiments, the one or more types of stochastic barcodes are attached to a solid support. In some embodiments, the one or more types of stochastic barcodes are attached to a substrate. In some embodiments, the kit further comprises a buffer. In some embodiments, the kit further comprises a cartridge. In some embodiments, the one or more supports are pre-loaded on a substrate. In some embodiments, the kit further comprises reagents for a reverse transcription reaction. In some embodiments, the kit further comprises reagents for an amplification reaction.

In one aspect, the disclosure provides for a method comprising: imaging a sample contacted to a substrate comprising a plurality of probes, thereby producing an image; lysing the sample thereby releasing nucleic acids from the sample; analyzing the nucleic acids from the sample at locations on the substrate; correlating locations on the image with data from the analyzing to identify a spatial location of a nucleic acid in a sample. In some embodiments, the imaging comprises staining the sample. In some embodiments, the staining comprises staining with a stain selected from the group consisting of: a fluorescent stain, a negative stain, and an antibody stain, or any combination thereof. In some embodiments, the imaging use a technique selected from the group consisting of: optical microscopy, electron microscopy, confocal microscopy, and fluorescence microscopy. In some embodiments, the performing immunohistological analysis produces an image. In some embodiments, the sample comprises a cell monolayer. In some embodiments, the sample comprises fixed cells. In some embodiments, the sample comprises a tissue section. In some embodiments, the lysing is performed by heating the sample, contacting the sample with a detergent, or changing the pH of the sample, or any combination thereof. In some embodiments, the analyzing comprises hybridizing the nucleic acids to the oligo(dT)s. In some embodiments, the nucleic acids comprise polyadenylated nucleic acids. In some embodiments, the method further comprises homopolymer tailing the nucleic acids. In some embodiments, the method further comprises amplifying the nucleic acids. In some embodiments, the amplifying comprises bridge amplification. In some embodiments, the amplifying comprises amplifying with a gene-specific primer. In some embodiments, the amplifying comprises amplifying with a universal primer. In some embodiments, the amplifying comprises amplifying with an oligo(dT) primer. In some embodiments, the method further comprises detecting the nucleic acids. In some embodiments, the detecting comprises hybridizing one or more probes to the nucleic acids. In some embodiments, the one or more probes comprise a fluorescent label. In some embodiments, the one or more probes can be 4 probes. In some embodiments, the analyzing comprises hybridizing the nucleic acids to a microarray. In some embodiments, the correlating comprises overlaying the image with the data. In some embodiments, the correlating comprises mapping the x-y location of a feature on the substrate onto the image. In some embodiments, the probes comprise oligo(dT). In some embodiments, the probes comprise gene-specific probes. In some embodiments, the probes comprise a combination of oligo(dT) probes and gene-specific probes. In some embodiments, the gene-specific probes are gene-specific for at least 2 genes.

In one aspect the disclosure provides for a method for diagnosing a subject comprising: imaging a sample from the subject contacted to a substrate comprising a plurality of probes, thereby producing an image; lysing the sample thereby releasing nucleic acids from the sample; analyzing the nucleic acids from the sample at locations on the substrate; diagnosing the subject based on the image and data from the analyzing. In some embodiments, the subject is a human. In some embodiments, the subject is a mouse, a dog, a rat, or a vertebrate. In some embodiments, the diagnosing comprises identifying different cell types of the sample. In some embodiments, the diagnosing comprises determining if different cell types respond to a therapy. In some embodiments, the diagnosing comprises determining a genotype of one or more cells in the sample. In some embodiments, the method further comprises treating the subject. In some embodiments, the treating comprises administering a drug to the subject. In some embodiments, the drug is chosen based on predicted responsiveness to the identified cell types of the sample. In some embodiments, the imaging comprises staining the sample. In some embodiments, the staining comprises staining with a stain selected from the group consisting of: a fluorescent stain, a negative stain, and an antibody stain, or any combination thereof. In some embodiments, the imaging use a technique selected from the group consisting of: optical microscopy, electron microscopy, confocal microscopy, and fluorescence microscopy. In some embodiments, the performing immunohistological analysis produces an image. In some embodiments, the sample comprises a cell monolayer. In some embodiments, the sample comprises fixed cells. In some embodiments, the sample comprises a tissue section. In some embodiments, the lysing is performed by heating the sample, contacting the sample with a detergent, or changing the pH of the sample, or any combination thereof. In some embodiments, the analyzing comprises hybridizing the nucleic acids to the oligo(dT)s. In some embodiments, the nucleic acids comprise polyadenylated nucleic acids. In some embodiments, the method further comprises homopolymer tailing the nucleic acids. In some embodiments, the method further comprises amplifying the nucleic acids. In some embodiments, the amplifying comprises bridge amplification. In some embodiments, the amplifying comprises amplifying with a gene-specific primer. In some embodiments, the amplifying comprises amplifying with a universal primer. In some embodiments, the amplifying comprises amplifying with an oligo(dT) primer. In some embodiments, the method further comprises detecting the nucleic acids. In some embodiments, the detecting comprises hybridizing one or more probes to the nucleic acids. In some embodiments, the one or more probes comprise a fluorescent label. In some embodiments, the one or more probes can be 4 probes. In some embodiments, the analyzing comprises hybridizing the nucleic acids to a microarray. In some embodiments, the probes comprise oligo(dT). In some embodiments, the probes comprise gene-specific probes. In some embodiments, the probes comprise a combination of oligo(dT) probes and gene-specific probes. In some embodiments, the gene-specific probes are gene-specific for at least 2 genes.

In one aspect, the disclosure provides for a method comprising: imaging a sample contacted to a first substrate comprising a plurality of probes, thereby producing an image; lysing the sample thereby releasing nucleic acids from the sample to hybridize to the plurality of probes; analyzing the nucleic acids from the sample at locations on the substrate; and replicating the first substrate thereby making a replicate substrate. In some embodiments, the probes of the first substrate comprise oligo(dT). In some embodiments, the probes of the first substrate comprise gene-specific primers. In some embodiments, probes of the replicate substrate comprise gene-specific primers for another location on the same gene as the gene-specific primers on the first substrate. In some embodiments, the replicating comprises contacting the first substrate with a replicate substrate. In some embodiments, the replicating comprises hybridizing nucleic acids from the first substrate to the replicate substrate. In some embodiments, the imaging comprises staining the sample. In some embodiments, the staining comprises staining with a stain selected from the group consisting of: a fluorescent stain, a negative stain, and an antibody stain, or any combination thereof. In some embodiments, the imaging use a technique selected from the group consisting of: optical microscopy, electron microscopy, confocal microscopy, and fluorescence microscopy. In some embodiments, the performing immunohistological analysis produces an image. In some embodiments, the sample comprises a cell monolayer. In some embodiments, the sample comprises fixed cells. In some embodiments, the sample comprises a tissue section. In some embodiments, the lysing is performed by heating the sample, contacting the sample with a detergent, or changing the pH of the sample, or any combination thereof. In some embodiments, the analyzing comprises hybridizing the nucleic acids to the oligo(dT)s. In some embodiments, the method further comprises homopolymer tailing the nucleic acids. In some embodiments, the method further comprises amplifying the nucleic acids to generate amplicons. In some embodiments, the amplifying comprises bridge amplification. In some embodiments, the amplifying comprises amplifying with a gene-specific primer. In some embodiments, the amplifying comprises amplifying with a universal primer. In some embodiments, the amplifying comprises amplifying with an oligo(dT) primer. In some embodiments, the replicating comprises hybridizing the amplicons onto the replicate substrate.

Definitions

Unless otherwise defined, all technical terms used herein have the same meaning as commonly understood by one of ordinary skill in the art in the field to which this disclosure belongs. As used in this specification and the appended claims, the singular forms "a," "an," and "the" include plural references unless the context clearly dictates otherwise. Any reference to "or" herein is intended to encompass "and/or" unless otherwise stated.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, barcodes, stochastic barcodes, or molecular labels. The adapters can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can also have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some embodiments two or more associated species are "tethered", "attached", or "immobilized" to one another or to a common solid or semisolid surface. An association may refer to covalent or non-covalent means for attaching labels to solid or semi-solid supports such as beads. An association may be a covalent bond between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence.

As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of stochastic barcodes made up of many different labels. A non-depleting reservoir can comprise large numbers of different stochastic barcodes such that when the non-depleting reservoir is associated with a pool of targets each target is likely to be associated with a unique stochastic barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of stochastic barcodes detected then allows calculation of the number of target molecules present in the original collection or sample. When the ratio of the number of copies of a target molecule present to the number of unique stochastic barcodes is low, the labeled target molecules are highly unique (i.e. there is a very low probability that more than one target molecule will have been labeled with a given label).

As used herein, a "nucleic acid" can generally refer to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine (1H-pyrimido(5, 4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',':4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of stochastic barcodes may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A solid support may be used interchangeably with the term "bead." A solid support can refer to a "substrate." A substrate can be a type of solid support. A substrate can refer to a continuous solid or semi-solid surface on which the methods of the disclosure may be performed. A substrate can refer to an array, a cartridge, a chip, a device, and a slide, for example. As used herein, "solid support" and "substrate" are sometimes used interchangeably.

As used here, the term, "spatial label" can refer to a label which can be associated with a position in space.

As used herein, the term "stochastic barcode" can refer to a polynucleotide sequence comprising labels. A stochastic barcode can be a polynucleotide sequence that can be used for stochastic labeling. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets.

As used herein, the term "target" can refer to a composition which can be associated with a stochastic barcode. Exemplary suitable targets for analysis by the disclosed methods, devices, and systems include oligonucleotides, DNA, RNA, mRNA, microRNA, tRNA, and the like. Targets can be single or double stranded. In some embodiments targets can be proteins. In some embodiments targets are lipids.

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the *Lactococcus lactis* LI.LtrB intron reverse transcriptase, the *Thermosynechococcus elongates* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

As used herein, the term "template switching" can refer to the ability of a reverse transcriptase to switch from an initial nucleic acid sequence template to the 3' end of a new nucleic acid sequence template having little or no complementarity to the 3' end of the nucleic acid synthesized from the initial template. Nucleic acid copies of a target polynucleotide can be made using template switching. Template switching allows, e.g., a DNA copy to be prepared using a reverse transcriptase that switches from an initial nucleic acid sequence template to the 3' end of a new nucleic acid sequence template having little or no complementarity to the 3' end of the DNA synthesized from the initial template, thereby allowing the synthesis of a continuous product DNA that directly links an adaptor sequence to a target oligonucleotide sequence without ligation. Template switching can comprise ligation of adaptor, homopolymer tailing (e.g., polyadenylation), random primer, or an oligonucleotide that the polymerase can associate with.

Stochastic Barcodes with Spatial Labels and Dimension Labels

Disclosed herein are methods, compositions, devices, systems, and kits for spatial stochastic barcoding. Some embodiments disclosed herein provide methods determining the number and spatial locations of a plurality of targets in a sample. The methods include, in some embodiments, stochastically barcoding the plurality of targets in the sample using a plurality of stochastic barcodes, wherein each of the plurality of stochastic barcodes include a spatial label and a molecular label; estimating the number of each of the plurality of targets using the molecular label; and identifying the spatial location of each of the plurality of targets using the spatial label. In some embodiments, the method can be multiplexed. The sample can comprise a plurality of cells and the plurality of targets can be associated with the plurality of cells.

Disclosed here are methods for determining spatial locations of a plurality of targets in a sample. In some embodiments, the methods include: stochastically barcoding the plurality of targets in the sample at one or more time points using a plurality of stochastic barcodes, wherein each of the plurality of stochastic barcodes comprises a spatial label; and identifying the spatial location of each of the plurality of targets using the spatial label. Stochastically barcoding the plurality of targets in the sample using the plurality of stochastic barcodes can include stochastically barcoding the plurality of targets in the sample at different time points using the plurality of stochastic barcodes. Each of the plurality of stochastic barcodes can include a dimension label, and the dimension labels of the plurality of stochastic barcodes used for stochastic barcoding the plurality of targets at the different time points can be different. The dimension labels can correlate with the different time points.

Spatial stochastic barcoding can refer to the stochastic barcoding of a plurality of target molecules in single cells to determine spatial orientation of the target molecules. As shown in FIG. 1, the disclosure provides for a method for correlating information in real physical space with information in chemical space. A sample comprising a two dimensional or three-dimensional sample (e.g., a cell) 105 can be divided into multiple sections, for example 110/111/112/113. In some embodiments, sections 110/111/112/113 can be physically divided, then chemically divided based on the physical division. In some embodiments, sections 110/111/112/113 can be chemically divided without physical division. In some embodiments, the sections 110/111/112/113 can be physically separated 115 from the sample 105. Each section 110/111/112/113 can be placed in a separate on a substrate 125. The sections 110/111/112/113 in the substrate 125 can be subjected to stochastic barcoding. Stochastic barcoding can comprise labeling distinct targets in each section 110/111/112/113 with a different barcode. In some embodiments, the different barcode comprises a spatial label. The sections can be stochastically labeled, amplified, and/or digitally counted, wherein the number of distinct targets can be estimated from the digital counting of different barcodes. The information in the spatial label of the different barcode can correspond to a location on the sample 105. In this way, the method can be used to determine the number of distinct targets in a sample 105 at distinct physical locations.

The methods, devices and systems disclosed herein may be used for a variety of applications in basic research, biomedical research, environmental testing, and clinical diagnostics. Examples of applications for the disclosed methods devices and systems include, but are not limited to, genotyping, gene expression profiling, detection and identification of rare cells, diagnosis of a disease or condition, determining prognosis for a disease or condition, determining a course of treatment for a disease or condition, and monitoring the response to treatment for a disease or condition, and understanding biological development processes. For example, the methods of the disclosure can be used for whole transcriptome analysis, rare cell (e.g., circulating tumor cell) analysis, chimeric antigen receptor T-cell (CAR-T) therapy analysis (e.g., determining specific cells that respond to CAR-T therapy versus non-responders), and neuroscience (e.g., therapies and diagnostics for, e.g., Autism, Schizophrenia, Bipolar disorder, Parkinson's disease, and Alzheimer's disease). In some embodiments, the methods can include treating the subject. Treating the subject can include administering a drug to the subject.

Figure 2:
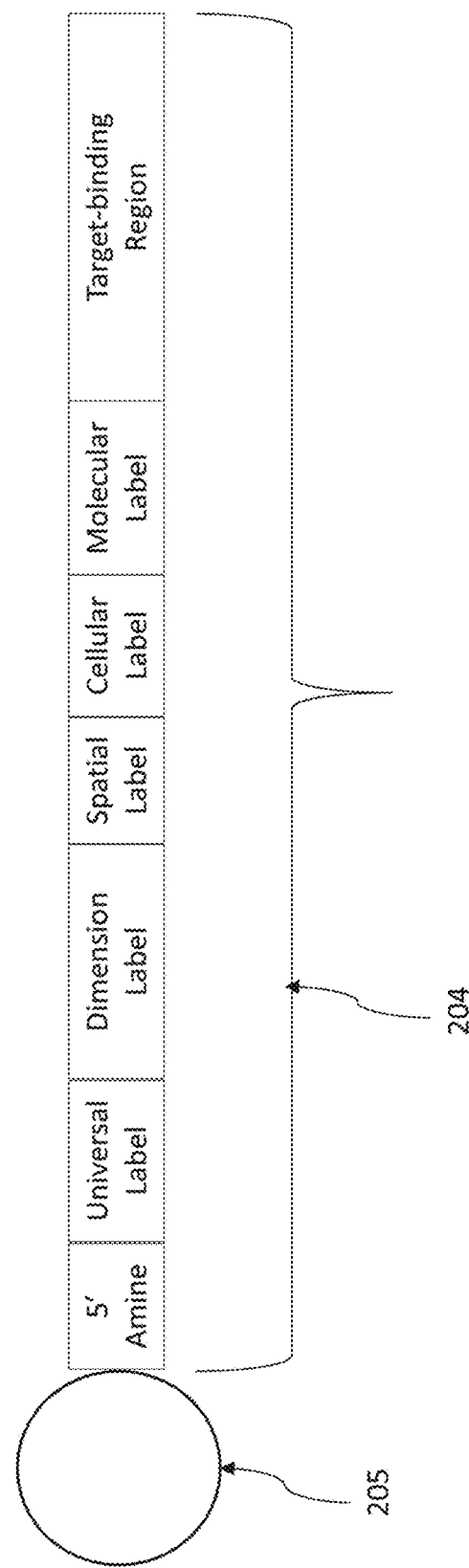
FIG. 2 illustrates a non-limiting exemplary stochastic barcode.

A stochastic barcode can refer to a polynucleotide sequence that may be used to stochastically label (e.g., barcode, tag) a target. A stochastic barcode can comprise one or more labels. Exemplary labels can include a universal label, a cellular label, a molecular label, a sample label, a plate label, a spatial label, and/or a pre-spatial label. FIG. 2 illustrates an exemplary stochastic barcode with a spatial label of the disclosure. A stochastic barcode 204 can comprise a 5'amine that may link the stochastic barcode to a solid support 205. The stochastic barcode can comprise a universal label, a dimension label, a spatial label, a cellular label, and/or a molecular label. The universal label may be 5'-most label. The molecular label may be the 3'-most label. The spatial label, dimension label, and the cellular label may be in any order. In some embodiments, the universal label, the spatial label, the dimension label, the cellular label, and the molecular label are in any order. The stochastic barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, and any combination thereof. In some embodiments, the plurality of targets can include deoxyribonucleic acids (DNAs).

For example, a target-binding region can comprise an oligo(dT) sequence which can interact with poly(A) tails of mRNAs. In some embodiments, the labels of the stochastic barcode (e.g., universal label, dimension label, spatial label, cellular label, and molecular label) may be separated by 1, 2, 3, 4, 5, 6, 7, 8, 9, 10, 11, 12, 13, 14, 15, 16, 17, 18, 19, or 20 or more nucleotides.

In some embodiments, stochastically barcoding the plurality of targets in the sample includes hybridizing the plurality of stochastic barcodes with the plurality of targets to generate stochastically barcoded targets, and at least one of the plurality of targets is hybridized to one of the plurality of stochastic barcodes. A portion or all of the plurality of targets can be hybridized to the plurality of stochastic barcodes. For example, in some embodiments, each of the plurality of targets is hybridized to one of the plurality of stochastic barcodes. In some embodiments, each of at least two, three, four, five, ten, twenty, fifty, one hundred, or one thousand of the plurality of targets is hybridized to one of the plurality of stochastic barcodes. A stochastic barcode can comprise one or more universal labels. The one or more universal labels can be the same for all stochastic barcodes in the set of stochastic barcodes attached to a given solid support. In some embodiments, the one or more universal labels can be the same for all stochastic barcodes attached to a plurality of beads. In some embodiments, a universal label can comprise a nucleic acid sequence that is capable of hybridizing to a sequencing primer. Sequencing primers can be used for sequencing stochastic barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the stochastic barcode. A universal label can comprise a sequence that can be used for extension of the stochastic barcode or a region within the stochastic barcode. A universal label can be at least about 1, 2, 3, 4, 5, 10, 15, 20, 25, 30, 35, 40, 45, 50 or more nucleotides in length. A universal label can comprise at least about 10 nucleotides. A universal label can be at most about 1, 2, 3, 4, 5, 10, 15, 20, 25, 30, 35, 40, 45, 50 or more nucleotides in length. In some embodiments, a cleavable linker or modified nucleotide can be part of the universal label sequence to enable the stochastic barcode to be cleaved off from the support.

A stochastic barcode can comprise a dimension label. A dimension label can comprise a nucleic acid sequence that provides information about a dimension in which the stochastic labeling occurred. For example, a dimension label can provide information about the time at which a target was stochastically barcoded. A dimension label can be associated with a time of stochastic barcoding in a sample. A dimension label can be activated at the time of stochastic labeling. Different dimension labels can be activated at different times. The dimension label provides information about the order in which targets, groups of targets, and/or samples were stochastically barcoded. For example, a population of cells can be stochastically barcoded at the G0 phase of the cell cycle. The cells can be pulsed again with stochastic barcodes at the G1 phase of the cell cycle. The cells can be pulsed again with stochastic barcodes at the S phase of the cell cycle, and so on. Stochastic barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be stochastically labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, or 10 or more times. The dimension label can be reversibly activatable, for example, at least 1, 2, 3, 4, 5, 6, 7, 8, 9, or 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all stochastic barcodes attached to a given solid support (e.g., bead), but different for different solid supports (e.g., beads). In some embodiments, at least 60%, 70%, 80%, 85%, 90%, 95%, 97%, 99% or 100% of stochastic barcodes on the same solid support can comprise the same dimension label. In some embodiments, at least 60% of stochastic barcodes on the same solid support can comprise the same dimension label. In some embodiments, at least 95% of stochastic barcodes on the same solid support can comprise the same dimension label.

There can be as many as $10^6$ or more unique dimension label sequences represented in a plurality of solid supports (e.g., beads). A dimension label can be at least about 1, 2, 3, 4, 5, 10, 15, 20, 25, 30, 35, 40, 45, 50 or more nucleotides in length. A dimension label can be at most about 300, 200, 100, 90, 80, 70, 60, 50, 40, 30, 20, 15, 12, 10, 9, 8, 7, 6, 5, 4 or fewer or more nucleotides in length. A dimension label can comprise between about 5 to about 200 nucleotides. A dimension label can comprise between about 10 to about 150 nucleotides. A dimension label can comprise between about 20 to about 125 nucleotides in length.

A stochastic barcode can comprise a spatial label. A spatial label can comprise a nucleic acid sequence that provides information about the spatial orientation of a target molecule which is associated with the stochastic barcode. A spatial label can be associated with a coordinate in a sample.

The coordinate can be a fixed coordinate. For example a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g. a well, a container, or a droplet). In some embodiments, multiple spatial labels are used together to encode one or more positions in space.

The spatial label can be identical for all stochastic barcodes attached to a given solid support (e.g., bead), but different for different solid supports (e.g., beads). In some embodiments, at least 60%, 70%, 80%, 85%, 90%, 95%, 97%, 99% or 100% of stochastic barcodes on the same solid support can comprise the same spatial label. In some embodiments, at least 60% of stochastic barcodes on the same solid support can comprise the same spatial label. In some embodiments, at least 95% of stochastic barcodes on the same solid support can comprise the same spatial label.

There can be as many as $10^6$ or more unique spatial label sequences represented in a plurality of solid supports (e.g., beads). A spatial label can be at least about 1, 2, 3, 4, 5, 10, 15, 20, 25, 30, 35, 40, 45, 50 or more nucleotides in length. A spatial label can be at most about 300, 200, 100, 90, 80, 70, 60, 50, 40, 30, 20, 15, 12, 10, 9, 8, 7, 6, 5, 4 or fewer or more nucleotides in length. A spatial label can comprise between about 5 to about 200 nucleotides. A spatial label can comprise between about 10 to about 150 nucleotides. A spatial label can comprise between about 20 to about 125 nucleotides in length.

Stochastic barcodes can comprise a cellular label. A cellular label can comprise a nucleic acid sequence that provides information for determining which target nucleic acid originated from which cell. In some embodiments, the cellular label is identical for all stochastic barcodes attached to a given solid support (e.g., bead), but different for different solid supports (e.g., beads). In some embodiments, at least 60%, 70%, 80%, 85%, 90%, 95%, 97%, 99% or 100% of stochastic barcodes on the same solid support can comprise the same cellular label. In some embodiments, at least 60% of stochastic barcodes on the same solid support can comprise the same cellular label. In some embodiment, at least 95% of stochastic barcodes on the same solid support can comprise the same cellular label.

There can be as many as $10^6$ or more unique cellular label sequences represented in a plurality of solid supports (e.g., beads). A cellular label can be at least about 1, 2, 3, 4, 5, 10, 15, 20, 25, 30, 35, 40, 45, 50 or more nucleotides in length. A cellular label can be at most about 300, 200, 100, 90, 80, 70, 60, 50, 40, 30, 20, 15, 12, 10, 9, 8, 7, 6, 5, 4 or fewer or more nucleotides in length. A cellular label can comprise between about 5 to about 200 nucleotides. A cellular label can comprise between about 10 to about 150 nucleotides. A cellular label can comprise between about 20 to about 125 nucleotides in length.

The cellular label can further comprise a unique set of nucleic acid sub-sequences of defined length, e.g. 7 nucleotides each (equivalent to the number of bits used in some Hamming error correction codes), which can be designed to provide error correction capability. The set of error correction sub-sequences comprise 7 nucleotide sequences can be designed such that any pairwise combination of sequences in the set exhibits a defined "genetic distance" (or number of mismatched bases), for example, a set of error correction sub-sequences can be designed to exhibit a genetic distance of 3 nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be 3 nucleotides, 7 nucleotides, 15 nucleotides, or 31 nucleotides in length. In some embodiments, nucleic acid sub-sequences of other lengths can be used for creating error correction codes.

In some embodiments, stochastic barcodes can comprise a molecular label. A molecular label can comprise a nucleic acid sequence that provides identifying information for the specific type of target nucleic acid species hybridized to the stochastic barcode. A molecular label can comprise a nucleic acid sequence that provides a counter for the specific occurrence of the target nucleic acid species hybridized to the stochastic barcode (e.g., target-binding region). In some embodiments, a diverse set of molecular labels are attached to a given solid support (e.g., bead). In some embodiments, there can be as many as $10^5$ or more unique molecular label sequences attached to a given solid support (e.g., bead). In some embodiments, there can be as many as $10^4$ or more unique molecular label sequences attached to a given solid support (e.g., bead). In some embodiments, there can be as many as $10^3$ or more unique molecular label sequences attached to a given solid support (e.g., bead). In some embodiments, there can be as many as $10^2$ or more unique molecular label sequences attached to a given solid support (e.g., bead). A molecular label can be at least about 1, 2, 3, 4, 5, 10, 15, 20, 25, 30, 35, 40, 45, 50 or more nucleotides in length. A molecular label can be at most about 300, 200, 100, 90, 80, 70, 60, 50, 40, 30, 20, 15, 12, 10, 9, 8, 7, 6, 5, 4 or fewer nucleotides in length.

Stochastic barcodes can comprise a target binding region. In some embodiments, the target binding regions can comprise a nucleic acid sequence that hybridizes specifically to a target (e.g. target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g. an EcoRI sticky-end overhang). The stochastic barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, or an oligo-dT sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all stochastic barcodes attached to a given bead. In some embodiments, the target binding regions for the plurality of stochastic barcodes attached to a given bead can comprise two or more different target binding sequences. A target binding region can be at least about 5, 10, 15, 20, 25, 30, 35, 40, 45, 50 or more nucleotides in length. A target binding region can be at most about 5, 10, 15, 20, 25, 30, 35, 40, 45, 50 or more nucleotides in length.

A stochastic barcode can comprise an orientation property which can be used to orient (e.g., align) the stochastic barcodes. A stochastic barcode can comprise a moiety for isoelectric focusing. Different stochastic barcodes can comprise different isoelectric focusing points. When these stochastic barcodes are introduced to a sample, the sample can undergo isoelectric focusing in order to orient the stochastic barcodes into a known way. In this way, the orientation property can be used to develop a known map of stochastic barcodes in a sample. Exemplary orientation properties can include, electrophoretic mobility (e.g., based on size of the stochastic barcode), isoelectric point, spin, conductivity, and/or self-assembly. For example, stochastic barcodes with an orientation property of self-assembly, can self-assemble into a specific orientation (e.g., nucleic acid nanostructure) upon activation.

A stochastic barcode can comprise an affinity property. A spatial label can comprise an affinity property. An affinity property can include a chemical and/or biological moiety that can facilitate binding of the stochastic barcode to another entity (e.g., cell receptor). For example, an affinity property can comprise an antibody. An antibody can be specific for a specific moiety (e.g., receptor) on a sample. An antibody can guide the stochastic barcode to a specific cell type or molecule. Targets at and/or near the specific cell type or molecule can be stochastically labeled. An affinity property can also provide spatial information in addition to the nucleotide sequence of the spatial label because the antibody can guide the stochastic barcode to a specific location. An antibody can be a therapeutic antibody. An antibody can be a monoclonal antibody. An antibody can be a polyclonal antibody. An antibody can be humanized. An antibody can be chimeric. An antibody can be a naked antibody. An antibody can be a fusion antibody.

An antibody, can refer to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody can be an antibody fragment. An antibody fragment can be a portion of an antibody such as F(ab')2, Fab', Fab, Fv, sFv and the like. An antibody fragment can bind with the same antigen that is recognized by the full-length antibody. An antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for antibodies for cancer cells, antibodies for viruses, antibodies that bind to cell surface receptors (CD8, CD34, CD45), and therapeutic antibodies.

Solid Supports

The stochastic barcodes disclosed herein can be associated to (e.g., attached to) a solid support (e.g., a bead). In some embodiments, stochastically barcoding the plurality of targets in the sample can be performed with a solid support including a plurality of synthetic particles associated with the plurality of stochastic barcodes. In some embodiments, the solid support can include a plurality of synthetic particles associated with the plurality of stochastic barcodes. The spatial labels of the plurality of stochastic barcodes on different solid supports can differ by at least one nucleotide. The solid support can, for example, include the plurality of stochastic barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The stochastic barcodes may not be associated with solid supports. The stochastic barcodes can be individual nucleotides. The stochastic barcodes can be associated with a substrate.

As used herein, the terms "tethered", "attached", and "immobilized" are used interchangeably, and can refer to covalent or non-covalent means for attaching stochastic barcodes to a solid support. Any of a variety of different solid supports can be used as solid supports for attaching pre-synthesized stochastic barcodes or for in situ solid-phase synthesis of stochastic barcode.

In some embodiments, a solid support is a bead. A bead can encompass one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, sepharose, agarose, hydrogel, polymer, cellulose, nylon, and any combination thereof.

The diameter of the beads can vary, for example, be at least about 100 nm, 500 nm, 1 μm, 5 μm, 10 μm, 20 μm, 25 μm, 30 μm, 35 μm, 40 μm, 45 μm or 50 μm. In some embodiments, the diameter of the beads can be at most about 100 nm, 500 nm, 1 μm, 5 μm, 10 μm, 20 μm, 25 μm, 30 μm, 35 μm, 40 μm, 45 μm or 50 μm. In some embodiments, the diameter of the bead can be related to the diameter of the wells of the substrate. For example, the diameter of the bead can be at least 10%, 20%, 30%, 40%, 50%, 60%, 70%, 80%, 90% or 100% longer or shorter than the diameter of the well. In some embodiments, the diameter of the bead can be at most 10%, 20%, 30%, 40%, 50%, 60%, 70%, 80%, 90% or 100% longer or shorter than the diameter of the well. The diameter of the bead can be related to the diameter of a cell (e.g., a single cell entrapped by a well of the substrate). The diameter of the bead can be at least 10%, 20%, 30%, 40%, 50%, 60%, 70%, 80%, 90%, 100%, 150%, 200%, 250%, or 300% or more longer or shorter than the diameter of the cell. The diameter of the bead can be at most 10%, 20%, 30%, 40%, 50%, 60%, 70%, 80%, 90%, 100%, 150%, 200%, 250%, or 300% or more longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the stochastic barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g. impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a stochastic barcode. A bead can change size, for example due to swelling in an organic or inorganic solution. A bead can be hydrophobic. A bead can be hydrophilic. A bead can be biocompatible.

A solid support (e.g., bead) can be visualized. The solid support can comprise a visualizing tag (e.g., fluorescent dye). A solid support (e.g., bead) can be etched with an identifier (e.g., a number). The identifier can be visualized through imaging the beads.

A solid support can refer to an insoluble, semi-soluble, or insoluble material. A solid support can be referred to as "functionalized" when it includes a linker, a scaffold, a building block, or other reactive moiety attached thereto, whereas a solid support can be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, synthetic particles, nanoparticles, plates, and arrays. Solid supports can include beads (e.g., silica gel, controlled pore glass, magnetic beads, Dynabeads, Wang resin; Merrifield resin, Sephadex/Sepharose beads, cellulose beads, polystyrene beads etc.), capillaries, flat supports such as glass fiber filters, glass surfaces, metal surfaces (steel, gold silver, aluminum, silicon and copper), glass supports, plastic supports, silicon supports, chips, filters, membranes, microwell plates, slides, or the like. plastic materials including multi-well plates or membranes (e.g., formed of polyethylene, polypropylene, polyamide, polyvinylidene difluoride), wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

In some embodiments stochastic barcodes of the disclosure can be attached to a polymer matrix (e.g., gel, hydrogel). The polymer matrix can be able to permeate intracellular space (e.g., around organelles). The polymer matrix can able to be pumped throughout the circulatory system.

A solid support can be a biological molecule. For example a solid support can be a nucleic acid, a protein, an antibody, a histone, a cellular compartment, a lipid, a carbohydrate, and the like. Solid supports that are biological molecules can be amplified, translated, transcribed, degraded, and/or modified (e.g., pegylated, sumoylated). A solid support that is a biological molecule can provide spatial and time information in addition to the spatial label that is attached to the biological molecule. For example, a biological molecule can comprise a first confirmation when unmodified, but can change to a second confirmation when modified. The different conformations can expose stochastic barcodes of the disclosure to targets. For example, a biological molecule can comprise stochastic barcodes that are inaccessible due to folding of the biological molecule. Upon modification of the biological molecule (e.g., acetylation), the biological molecule can change conformation to expose the stochastic labels. The timing of the modification can provide another time dimension to the method of stochastic barcoding of the disclosure.

In another example, the biological molecule comprising stochastic barcodes of the disclosure can be located in the cytoplasm of a cell. Upon activation, the biological molecule can move to the nucleus, whereupon stochastic barcoding can take place. In this way, modification of the biological molecule can encode additional space-time information for the targets identified by the stochastic barcodes.

A dimension label can provide information about space-time of a biological event (e.g., cell division). For example, a dimension label can be added to a first cell, the first cell can divide generating a second daughter cell, the second daughter cell can comprise all, some or none of the dimension labels. The dimension labels can be activated in the original cell and the daughter cell. In this way, the dimension label can provide information about time of stochastic barcoded in distinct spaces.

Microarrays

In some embodiments, a solid support/substrate can refer to a microarray. A microarray can comprise a plurality of polymers, e.g., oligomers, synthesized in situ or pre-synthesized and deposited on a substrate in an array pattern. Microarrays of oligomers manufactured by solid-phase DNA synthesis can have oligomer densities approaching 106/micron2. As used herein, the support-bound oligomers can be referred to as called "probes", which function to bind or hybridize with a sample of DNA or RNA material under test. However, the terms can be used interchangeably wherein the surface-bound oligonucleotides as targets and the solution sample of nucleic acids as probes. Further, some investigators bind the target sample under test to the microarray substrate and put the oligomer probes in solution for hybridization. Either of the "target" or "probes" can be the one that is to be evaluated by the other (thus, either one could be an unknown mixture of polynucleotides to be evaluated by binding with the other). All of these iterations are within the scope of this discussion herein. For the purpose of simplicity only, herein the probe is the surface-bound oligonucleotide of known sequence and the target is the moiety in a mobile phase (typically fluid), to be detected by the surface-bound probes. The plurality of probes and/or targets in each location in the array can be referred to as a "nucleic acid feature" or "feature." A feature is defined as a locus onto which a large number of probes and/or targets all having the same nucleotide sequence are immobilized.

Depending on the make-up of the target sample, hybridization of probe features may or may not occur at all probe feature locations and can occur to varying degrees at the different probe feature locations.

An "array" can refer to an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. Array Plate or a Plate a body having a plurality of arrays in which each array can be separated from the other arrays by a physical barrier resistant to the passage of liquids and forming an area or space, referred to as a well.

The density of the microarrays can be higher than 500, 5000, 50000, or 500,000 different probes per $cm^2$. The feature size of the probes can be smaller than 500, 150, 25, 9, or 1 $\mu m^2$. The locations of the probes can be determined or decipherable. For example, in some arrays, the specific locations of the probes are known before binding assays. In some other arrays, the specific locations of the probes are unknown until after the assays. The probes can be immobilized on a substrate, optionally, via a linker, beads, etc.

The array can comprise features made up of oligo(dT) probes. The array can comprise features made up of gene-specific probes. In some embodiments, the array is a microarray. In some embodiments, the array is an array of solid supports (e.g., beads). In some embodiments, the array is planar. In some embodiments, the array has topographical features.

Substrates

A substrate can refer to a type of solid support. A substrate can refer to a solid support that can comprise stochastic barcodes of the disclosure. A substrate can comprise a plurality of microwells. A microwell can comprise a small reaction chamber of defined volume. A microwell can entrap one or more cells. A microwell can entrap only one cell. A microwell can entrap one or more solid supports. A microwell can entrap only one solid support. In some embodiments, a microwell entraps a single cell and a single solid support (e.g., bead).

The microwells of the array can be fabricated in a variety of shapes and sizes. Appropriate well geometries can include, but are not limited to, cylindrical, conical, hemispherical, rectangular, or polyhedral (e.g., three dimensional geometries comprised of several planar faces, for example, hexagonal columns, octagonal columns, inverted triangular pyramids, inverted square pyramids, inverted pentagonal pyramids, inverted hexagonal pyramids, or inverted truncated pyramids). The microwells can comprise a shape that combines two or more of these geometries. For example, a microwell can be partly cylindrical, with the remainder having the shape of an inverted cone. A microwell can include two side-by-side cylinders, one of larger diameter (e.g. that corresponds roughly to the diameter of the beads) than the other (e.g. that corresponds roughly to the diameter of the cells), that are connected by a vertical channel (that is, parallel to the cylinder axes) that extends the full length (depth) of the cylinders. The opening of the microwell can be at the upper surface of the substrate. The opening of the microwell can be at the lower surface of the substrate. The closed end (or bottom) of the microwell can be flat. The closed end (or bottom) of the microwell can have a curved surface (e.g., convex or concave). The shape and/or size of the microwell can be determined based on the types of cells or solid supports to be trapped within the microwells.

Microwell dimensions can be characterized in terms of the diameter and depth of the well. As used herein, the diameter of the microwell refers to the largest circle that can be inscribed within the planar cross-section of the microwell geometry. The diameter of the microwells can range from about 1-fold to about 10-folds the diameter of the cells or solid supports to be trapped within the microwells. The microwell diameter can be at least 1-fold, at least 1.5-fold, at least 2-folds, at least 3-folds, at least 4-folds, at least 5-folds, or at least 10-folds the diameter of the cells or solid supports to be trapped within the microwells. The microwell diameter can be at most 10-folds, at most 5-folds, at most 4-folds, at most 3-folds, at most 2-folds, at most 1.5-fold, or at most 1-fold the diameter of the cells or solid supports to be trapped within the microwells. The microwell diameter can be about 2.5-folds the diameter of the cells or solid supports to be trapped within the microwells.

The diameter of the microwells can be specified in terms of absolute dimensions. The diameter of the microwells can range from about 5 to about 50 micrometers. The microwell diameter can be at least 5 micrometers, at least 10 micrometers, at least 15 micrometers, at least 20 micrometers, at least 25 micrometers, at least 30 micrometers, at least 35 micrometers, at least 40 micrometers, at least 45 micrometers, or at least 50 micrometers. The microwell diameter can be at most 50 micrometers, at most 45 micrometers, at most 40 micrometers, at most 35 micrometers, at most 30 micrometers, at most 25 micrometers, at most 20 micrometers, at most 15 micrometers, at most 10 micrometers, or at most 5 micrometers. The microwell diameter can be about 30 micrometers.

In some embodiments, the diameter of each microwell can be, or can be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number between any two of these values, nanometer. In some embodiments, the diameter of each microwell can be, or can be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number between any two of these values, micrometer. In some embodiments, the diameter of each microwell can be, or can be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number between any two of these values, minimeter.

The microwell depth can be chosen to provide efficient trapping of cells and solid supports. The microwell depth can be chosen to provide efficient exchange of assay buffers and other reagents contained within the wells. The ratio of diameter to height (i.e. aspect ratio) can be chosen such that once a cell and solid support settle inside a microwell, they will not be displaced by fluid motion above the microwell. In some embodiments, the height of the microwell can be smaller than the diameter of the bead. For example, the height of the microwell can be at least 5, 10, 15, 20, 25, 30, 35, 40, 45, 50, 55, 60, 65, 70, 75, 80, 85, 90, 95, or 100% of the diameter of the bead. The bead can protrude outside of the microwell.

The dimensions of the microwell can be chosen such that the microwell has sufficient space to accommodate a solid support and a cell of various sizes without being dislodged by fluid motion above the microwell. The depth of the microwells can range from about 1-fold to about 10-fold the diameter of the cells or solid supports to be trapped within the microwells. The microwell depth can be at least 1-fold, at least 1.5-fold, at least 2-folds, at least 3-folds, at least 4-folds, at least 5-folds, or at least 10-folds the diameter of the cells or solid supports to be trapped within the microwells. The microwell depth can be at most 10-folds, at most 5-folds, at most 4-folds, at most 3-folds, at most 2-folds, at most 1.5-fold, or at most 1-fold the diameter of the cells or solid supports to be trapped within the microwells. The microwell depth can be about 2.5-folds the diameter of the cells or solid supports to be trapped within the microwells.

The depth of the microwells can be specified in terms of absolute dimensions. The depth of the microwells can range from about 10 to about 60 micrometers. The microwell depth can be at least 10 micrometers, at least 20 micrometers, at least 25 micrometers, at least 30 micrometers, at least 35 micrometers, at least 40 micrometers, at least 50 micrometers, or at least 60 micrometers. The microwell depth can be at most 60 micrometers, at most 50 micrometers, at most 40 micrometers, at most 35 micrometers, at most 30 micrometers, at most 25 micrometers, at most 20 micrometers, or at most 10 micrometers. The microwell depth can be about 30 micrometers.

In some embodiments, the depth of each microwell can be, or can be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number between any two of these values, nanometers. In some embodiments, the depth of each microwell can be, or can be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number between any two of these values, micrometers. In some embodiments, the depth of each microwell can be, or can be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number between any two of these values, minimeters.

The volume of the microwells used in the methods, devices, and systems of the present disclosure can vary, for example range from about 200 micrometers$^3$ to about 120,000 micrometers$^3$. The microwell volume can be at least 200 micrometers$^3$, at least 500 micrometers$^3$, at least 1,000 micrometers$^3$, at least 10,000 micrometers$^3$, at least 25,000 micrometers$^3$, at least 50,000 micrometers$^3$, at least 100,000 micrometers$^3$, or at least 120,000 micrometers$^3$. The microwell volume can be at most 120,000 micrometers$^3$, at most 100,000 micrometers$^3$, at most 50,000 micrometers$^3$, at most 25,000 micrometers$^3$, at most 10,000 micrometers$^3$, at most 1,000 micrometers$^3$, at most 500 micrometers$^3$, or at most 200 micrometers$^3$. The microwell volume can be about 25,000 micrometers$^3$. The microwell volume can fall within any range bounded by any of these values (e.g. from about 18,000 micrometers$^3$ to about 30,000 micrometers$^3$).

In some embodiments, each of the microwells can have a volume of 10, 20, 30, 40, 50, 60, 70, 80, 90, 100, 200, 300, 400, 500, 600, 700, 800, 900, 1000, or a number between any two of these values, nanoliters. In some embodiments, each of the microwells can have a volume of 1, 2, 3, 4, 5, 6, 7, 8, 9, 10, 20, 30, 40, 50, 60, 70, 80, 90, 100, 200, 300, 400, 500, 600, 700, 800, 900, 1000, or a number between any two of these values, microliters. In some embodiments, each of the microwells can have a volume of 1, 2, 3, 4, 5, 6, 7, 8, 9, 10, 20, 30, 40, 50, 60, 70, 80, 90, 100, 200, 300, 400, 500, 600, 700, 800, 900, 1000, or a number between any two of these values, miniliters.

The volumes of the microwells used in the methods, devices, and systems of the present disclosure can be further characterized in terms of the variation in volume from one microwell to another. The coefficient of variation (expressed as a percentage) for microwell volume can range from about 1% to about 10%. The coefficient of variation for microwell volume can be at least 1%, at least 2%, at least 3%, at least 4%, at least 5%, at least 6%, at least 7%, at least 8%, at least 9%, or at least 10%. The coefficient of variation for microwell volume can be at most 10%, at most 9%, at most 8%, at most 7%, at most 6%, at most 5%, at most 4%, at most 3%, at most 2%, or at most 1%. The coefficient of variation for microwell volume can have any value within a range encompassed by these values, for example between about 1.5% and about 6.5%. In some embodiments, the coefficient of variation of microwell volume can be about 2.5%.

The ratio of the volume of the microwells to the surface area of the beads (or to the surface area of a solid support to which stochastic barcode oligonucleotides can be attached) used in the methods, devices, and systems of the present disclosure can vary, for example range from about 2.5 to about 1,520 micrometers. The ratio can be at least 2.5, at least 5, at least 10, at least 100, at least 500, at least 750, at least 1,000, or at least 1,520. The ratio can be at most 1,520, at most 1,000, at most 750, at most 500, at most 100, at most 10, at most 5, or at most 2.5. In some embodiments, the ratio can be, or be about 67.5. The ratio of microwell volume to the surface area of the bead (or solid support used for immobilization) can fall within any range bounded by any of these values (e.g. from about 30 to about 120).

The wells of the microwell array can be arranged in a one dimensional, two dimensional, or three-dimensional array. A three dimensional array can be achieved, for example, by stacking a series of two or more two dimensional arrays (that is, by stacking two or more substrates comprising microwell arrays).

The pattern and spacing between microwells can be chosen to optimize the efficiency of trapping a single cell and single solid support (e.g., bead) in each well, as well as to maximize the number of wells per unit area of the array. The microwells can be distributed according to a variety of random or non-random patterns. For example, they can be distributed entirely randomly across the surface of the array substrate, or they can be arranged in a square grid, rectangular grid, hexagonal grid, or the like. The center-to-center distance (or spacing) between wells can vary from about 15 micrometers to about 75 micrometers. In other embodiments, the spacing between wells is at least 15 micrometers, at least 20 micrometers, at least 25 micrometers, at least 30 micrometers, at least 35 micrometers, at least 40 micrometers, at least 45 micrometers, at least 50 micrometers, at least 55 micrometers, at least 60 micrometers, at least 65 micrometers, at least 70 micrometers, or at least 75 micrometers. The microwell spacing can be at most 75 micrometers, at most 70 micrometers, at most 65 micrometers, at most 60 micrometers, at most 55 micrometers, at most 50 micrometers, at most 45 micrometers, at most 40 micrometers, at most 35 micrometers, at most 30 micrometers, at most 25 micrometers, at most 20 micrometers, or at most 15 micrometers. The microwell spacing can be about 55 micrometers. The microwell spacing can fall within any range bounded by any of these values (e.g. from about 18 micrometers to about 72 micrometers).

In some embodiments, microwells can be separated from each other by no more than 0.01, 0.1, 1, 2, 3, 4, 5, 6, 7, 8, 9, 10, 20, 30, 40, 50, 60, 70, 80, 90, 100, 200, 300, 400, 500, 600, 700, 800, 900, 1000, or a number between any two of these values, micrometers. In some embodiments, the microwells can be separated from one another by no more than 1, 2, 3, 4, 5, 6, 7, 8, 9, 10, 20, 30, 40, 50, 60, 70, 80, 90, 100, 200, 300, 400, 500, 600, 700, 800, 900, 1000, or a number between any two of these values, minimeters.

In some embodiments, the microwell array can comprise 100, 200, 300, 400, 500, 600, 700, 800, 900, 1000, 2000, 3000, 4000, 5000, 6000, 7000, 8000, 9000, 10000, or a number between any two of these values, wells per inch. In some embodiments, the microwell array can comprise 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number between any two of these values, wells per cm$^2$.

The microwell array can comprise surface features between the microwells that are designed to help guide cells and solid supports into the wells and/or prevent them from settling on the surfaces between wells. Examples of suitable surface features can include, but are not limited to, domed, ridged, or peaked surface features that encircle the wells or straddle the surface between wells.

The total number of wells in the microwell array can be determined by the pattern and spacing of the wells and the overall dimensions of the array. The number of microwells in the array can vary, for example, range from about 96 to about 5,000,000 or more. The number of microwells in the array can be at least 96, at least 384, at least 1,536, at least 5,000, at least 10,000, at least 25,000, at least 50,000, at least 75,000, at least 100,000, at least 500,000, at least 1,000,000, or at least 5,000,000. The number of microwells in the array can be at most 5,000,000, at most 1,000,000, at most 75,000, at most 50,000, at most 25,000, at most 10,000, at most 5,000, at most 1,536, at most 384, or at most 96 wells. The number of microwells in the array can be about 96. The number of microwells can be about 150,000. The number of microwells in the array can fall within any range bounded by any of these values (e.g. from about 100 to 325,000).

Microwell arrays can be fabricated using any of a number of fabrication techniques. Examples of fabrication methods that can be used include, but are not limited to, bulk micromachining techniques such as photolithography and wet chemical etching, plasma etching, or deep reactive ion etching; micro-molding and micro-embossing; laser micro-machining; 3D printing or other direct write fabrication processes using curable materials; and similar techniques.

Microwell arrays can be fabricated from any of a number of substrate materials. The choice of material can depend on the choice of fabrication technique, and vice versa. Examples of suitable materials can include, but are not limited to, silicon, fused-silica, glass, polymers (e.g. agarose, gelatin, hydrogels, polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COL), polyethylene terephthalate (PET), epoxy resins, thiol-ene based resins, metals or metal films (e.g. aluminum, stainless steel, copper, nickel, chromium, and titanium), and the like. A hydrophilic material can be desirable for fabrication of the microwell arrays (e.g. to enhance wettability and minimize non-specific binding of cells and other biological material). Hydrophobic materials that can be treated or coated (e.g. by oxygen plasma treatment, or grafting of a polyethylene oxide surface layer) can also be used. The use of porous, hydrophilic materials for the fabrication of the microwell array can be desirable in order to facilitate capillary wicking/venting of entrapped air bubbles in the device. The microwell array can be fabricated from a single material. The microwell array can comprise two or more different materials that have been bonded together or mechanically joined.

Microwell arrays can be fabricated using substrates of any of a variety of sizes and shapes. For example, the shape (or footprint) of the substrate within which microwells are fabricated can be square, rectangular, circular, or irregular in shape. The footprint of the microwell array substrate can be similar to that of a microtiter plate. The footprint of the microwell array substrate can be similar to that of standard microscope slides, e.g. about 75 mm long×25 mm wide (about 3" long×1" wide), or about 75 mm long×50 mm wide (about 3" long×2" wide). The thickness of the substrate within which the microwells are fabricated can range from about 0.1 mm thick to about 10 mm thick, or more. The thickness of the microwell array substrate can be at least 0.1 mm thick, at least 0.5 mm thick, at least 1 mm thick, at least 2 mm thick, at least 3 mm thick, at least 4 mm thick, at least 5 mm thick, at least 6 mm thick, at least 7 mm thick, at least 8 mm thick, at least 9 mm thick, or at least 10 mm thick. The thickness of the microwell array substrate can be at most 10 mm thick, at most 9 mm thick, at most 8 mm thick, at most 7 mm thick, at most 6 mm thick, at most 5 mm thick, at most 4 mm thick, at most 3 mm thick, at most 2 mm thick, at most 1 mm thick, at most 0.5 mm thick, or at most 0.1 mm thick. The thickness of the microwell array substrate can be about 1 mm thick. The thickness of the microwell array substrate can be any value within these ranges, for example, the thickness of the microwell array substrate can be between about 0.2 mm and about 9.5 mm.

A variety of surface treatments and surface modification techniques can be used to alter the properties of microwell array surfaces. Examples can include, but are not limited to, oxygen plasma treatments to render hydrophobic material surfaces more hydrophilic, the use of wet or dry etching techniques to smooth (or roughen) glass and silicon surfaces, adsorption or grafting of polyethylene oxide or other polymer layers (such as pluronic), or bovine serum albumin to substrate surfaces to render them more hydrophilic and less prone to non-specific adsorption of biomolecules and cells, the use of silane reactions to graft chemically-reactive functional groups to otherwise inert silicon and glass surfaces, etc. Photodeprotection techniques can be used to selectively activate chemically-reactive functional groups at specific locations in the array structure, for example, the selective addition or activation of chemically-reactive functional groups such as primary amines or carboxyl groups on the inner walls of the microwells can be used to covalently couple oligonucleotide probes, peptides, proteins, or other biomolecules to the walls of the microwells. The choice of surface treatment or surface modification utilized can depend both or either on the type of surface property that is desired and on the type of material from which the microwell array is made.

The openings of microwells can be sealed, for example, during cell lysis steps to prevent cross hybridization of target nucleic acid between adjacent microwells. A microwell (or array of microwells) can be sealed or capped using, for example, a flexible membrane or sheet of solid material (i.e. a plate or platten) that clamps against the surface of the microwell array substrate, or a suitable bead, where the diameter of the bead is larger than the diameter of the microwell.

A seal formed using a flexible membrane or sheet of solid material can comprise, for example, inorganic nanopore membranes (e.g., aluminum oxides), dialysis membranes, glass slides, coverslips, elastomeric films (e.g. PDMS), or hydrophilic polymer films (e.g., a polymer film coated with a thin film of agarose that has been hydrated with lysis buffer).

Solid supports (e.g., beads) used for capping the microwells can comprise any of the solid supports (e.g., beads) of the disclosure. In some embodiments, the solid supports are cross-linked dextran beads (e.g., Sephadex). Cross-linked dextran can range from about 10 micrometers to about 80 micrometers. The cross-linked dextran beads used for capping can be from 20 micrometers to about 50 micrometers. In some embodiments, the beads can be at least about 10, 20, 30, 40, 50, 60, 70, 80 or 90% larger than the diameter of the microwells. The beads used for capping can be at most about 10, 20, 30, 40, 50, 60, 70, 80 or 90% larger than the diameter of the microwells.

The seal or cap can allow buffer to pass into and out of the microwell, while preventing macromolecules (e.g., nucleic acids) from migrating out of the well. A macromolecule of at least about 1, 2, 3, 4, 5, 6, 7, 8, 9, 10, 12, 13, 14, 15, 16, 17, 18, 19, or 20 or more nucleotides can be blocked from migrating into or out of the microwell by the seal or cap. A macromolecule of at most about 1, 2, 3, 4, 5, 6, 7, 8, 9, 10, 12, 13, 14, 15, 16, 17, 18, 19, or 20 or more nucleotides can be blocked from migrating into or out of the microwell by the seal or cap.

Solid supports (e.g., beads) can be distributed among a substrate. Solid supports (e.g., beads) can be distributed among wells of the substrate, removed from the wells of the substrate, or otherwise transported through a device comprising one or more microwell arrays by means of centrifugation or other non-magnetic means. A microwell of a substrate can be pre-loaded with a solid support. A microwell of a substrate can hold at least 1, 2, 3, 4, or 5, or more solid supports. A microwell of a substrate can hold at most 1, 2, 3, 4, or 5 or more solid supports. In some embodiments, a microwell of a substrate can hold one solid support.

Individual cells and beads can be compartmentalized using alternatives to microwells, for example, a single solid support and single cell could be confined within a single droplet in an emulsion (e.g. in a droplet digital microfluidic system).

Cells could potentially be confined within porous beads that themselves comprise the plurality of tethered stochastic barcodes. Individual cells and solid supports can be compartmentalized in any type of container, microcontainer, reaction chamber, reaction vessel, or the like.

Single cell, stochastic barcoding or can be performed without the use of microwells. Single cell, stochastic barcoding assays can be performed without the use of any physical container. For example, stochastic barcoding without a physical container can be performed by embedding cells and beads in close proximity to each other within a polymer layer or gel layer to create a diffusional barrier between different cell/bead pairs. In another example, stochastic barcoding without a physical container can be performed in situ, in vivo, on an intact solid tissue, on an intact cell, and/or subcellularly.

Microwell arrays can be a consumable component of the assay system. Microwell arrays can be reusable. Microwell arrays can be configured for use as a stand-alone device for performing assays manually, or they can be configured to comprise a fixed or removable component of an instrument system that provides for full or partial automation of the assay procedure. In some embodiments of the disclosed methods, the bead-based libraries of stochastic barcodes can be deposited in the wells of the microwell array as part of the assay procedure. In some embodiments, the beads can be pre-loaded into the wells of the microwell array and provided to the user as part of, for example, a kit for performing stochastic barcoding and digital counting of nucleic acid targets.

In some embodiments, two mated microwell arrays can be provided, one pre-loaded with beads which are held in place by a first magnet, and the other for use by the user in loading individual cells. Following distribution of cells into the second microwell array, the two arrays can be placed face-to-face and the first magnet removed while a second magnet is used to draw the beads from the first array down into the corresponding microwells of the second array, thereby ensuring that the beads rest above the cells in the second microwell array and thus minimizing diffusional loss of target molecules following cell lysis, while maximizing efficient attachment of target molecules to the stochastic barcodes on the bead.

In some embodiments, a substrate does not include microwells. For example, beads can be assembled (e.g., self-assembled). The beads can self-assemble into a monolayer. The monolayer can be on a flat surface of the substrate. The monolayer can be on a curved surface of the substrate. The bead monolayer can be formed by any method, such as alcohol evaporation.

Three-Dimensional Substrates

A three-dimensional array can be any shape. A three-dimensional substrate can be made of any material used in a substrate of the disclosure. In some embodiments, a three-dimensional substrate comprises a DNA origami. DNA origami structures incorporate DNA as a building material to make nanoscale shapes. The DNA origami process can involve the folding of one or more long, "scaffold" DNA strands into a particular shape using a plurality of rationally designed "staple DNA strands. The sequences of the staple strands can be designed such that they hybridize to particular portions of the scaffold strands and, in doing so, force the scaffold strands into a particular shape. The DNA origami can include a scaffold strand and a plurality of rationally designed staple strands. The scaffold strand can have any sufficiently non-repetitive sequence.

The sequences of the staple strands can be selected such that the DNA origami has at least one shape to which stochastic labels can be attached. In some embodiments, the DNA origami can be of any shape that has at least one inner surface and at least one outer surface. An inner surface can be any surface area of the DNA origami that is sterically precluded from interacting with the surface of a sample, while an outer surface is any surface area of the DNA origami that is not sterically precluded from interacting with the surface of a sample. In some embodiments, the DNA origami has one or more openings (e.g., two openings), such that an inner surface of the DNA origami can be accessed by particles (e.g., solid supports). For example, in certain embodiments the DNA origami has one or more openings that allow particles smaller than 10 micrometers, 5 micrometers, 1 micrometer, 500 nm, 400 nm, 300 nm, 250 nm, 200 nm, 150 nm, 100 nm, 75 nm, 50 nm, 45 nm or 40 nm to contact an inner surface of the DNA origami.

The DNA origami can change shape (conformation) in response to one or more certain environmental stimuli. Thus an area of the DNA origami can be an inner surface when the DNA origami takes on some conformations, but can be an outer surface when the device takes on other conformations. In some embodiments, the DNA origami can respond to certain environmental stimuli by taking on a new conformation.

In some embodiments, the staple strands of the DNA origami can be selected such that the DNA origami is substantially barrel- or tube-shaped. The staples of the DNA origami can be selected such that the barrel shape is closed at both ends or is open at one or both ends, thereby permitting particles to enter the interior of the barrel and access its inner surface. In certain embodiments, the barrel shape of the DNA origami can be a hexagonal tube.

In some embodiments, the staple strands of the DNA origami can be selected such that the DNA origami has a first domain and a second domain, wherein the first end of the first domain is attached to the first end of the second domain by one or more single-stranded DNA hinges, and the second end of the first domain is attached to the second domain of the second domain by the one or more molecular latches. The plurality of staples can be selected such that the second end of the first domain becomes unattached to the second end of the second domain if all of the molecular latches are contacted by their respective external stimuli. Latches can be formed from two or more staple stands, including at least one staple strand having at least one stimulus-binding domain that is able to bind to an external stimulus, such as a nucleic acid, a lipid or a protein, and at least one other staple strand having at least one latch domain that binds to the stimulus binding domain. The binding of the stimulus-binding domain to the latch domain supports the stability of a first conformation of the DNA origami.

Spatial labels can be delivered to a sample in three dimensions. For example a sample can be associated with an array, wherein the array has spatial labels distributed or distributable in three dimensions. A three dimensional array can be a scaffolding, a porous substrate, a gel, a series of channels, or the like.

A three dimensional pattern of spatial labels can be associated with a sample by injecting the samples into known locations with the sample, for example using a robot. A single needle can be used to serially inject spatial labels at different depths into a sample. An array of needles can inject spatial labels at different depths to generate a three dimensional distribution of labels.

In some embodiments, a three dimensional solid support can be a device. For example, a needle array device (e.g., a biopsy needle array device) can be a substrate. Stochastic barcodes of the disclosure can be attached to the device. Placing the device in and/or on a sample can bring the stochastic barcodes of the disclosure into proximity with targets in and/or on the sample. Different parts of the device can have stochastic barcodes with different spatial labels. For example, on a needle array device, each needle of the device can be coated with stochastic barcodes with different spatial labels on each needle. In this way, spatial labels can provide information about the location of the targets (e.g., location in orientation to the needle array).

Probes

The solid support/substrate of the disclosure can comprise a plurality of probes. The probes can be at least 1, 2, 3, 4, 5, 6, 7, 8, 9, 10, 11, 12, 13, 14, 15, 16, 17, 18, 19, or 20 or more nucleotides in length. The probes can be at most 1, 2, 3, 4, 5, 6, 7, 8, 9, 10, 11, 12, 13, 14, 15, 16, 17, 18, 19, or 20 or more nucleotides in length.

The probes can be oligo(dT) probes. The probes can be any homopolymer sequence (e.g., poly(A), poly(C), poly (G), poly(U)).

The probes can be gene-specific. The probes can target any location of a gene (e.g., 3' UTR, 5' UTR, coding region, promoter). The probes on the substrate can be gene-specific for a plurality of genes. For example, a substrate can comprise probes that are gene-specific for at least 10, 20, 30, 40, 50, 60, 70, 80, 90, or 100 or more genes. A substrate can comprise probes that are gene-specific for at least 10, 20, 30, 40, 50, 60, 70, 80, 90, or 100 or more genes. The plurality of gene-specific probes can be dispersed throughout the substrate evenly. The plurality of gene-specific probes can be dispersed throughout the substrate in discrete locations. There can be an equivalent number of gene-specific probes for each gene. There can be an inequivalent number of gene-specific probes for each gene. For examples, one or more gene-specific probes can be represented on the substrate at least 10, 20, 30, 40, 50, 60, 70, or 80% or more compared to one or more other gene-specific probes. One or more gene-specific probes can be represented on the substrate at most 10, 20, 30, 40, 50, 60, 70, or 80% or more compared to one or more other gene-specific probes.

The substrate can comprise a plurality of gene-specific probes for a plurality of genes and a plurality of oligo(dT) probes. The combination of gene-specific probes and oligo (dT) probes can be useful for bridge amplification methods of the disclosure. The ratio of a gene-specific probe to an oligo(dT) probe can be at least 1:1, 1:2, 1:3, 1:4, or 1:5 or more. The ratio of a gene-specific probe to an oligo(dT) probe can be at most 1:1, 1:2, 1:3, 1:4, or 1:5 or more. The ratio of an oligo(dT) probe to a gene-specific probe can be at least 1:1, 1:2, 1:3, 1:4, or 1:5 or more. The ratio of an oligo(dT) probe to a gene-specific probe can be at most 1:1, 1:2, 1:3, 1:4, or 1:5 or more.

The probes on the replicate substrate can comprise any of the probes, or combination of probes of the disclosure. The probes on the replicate substrate can be the same as the initial substrate. The probes on the replicate substrate can be different from the initial substrate. For example, the probes on the initial substrate can be gene-specific for a first location of a gene. The probes on the replicate slide can be gene-specific for a second location on the same gene. In this way, the probes can be used to identify (e.g., generate and/or detect) multiple amplicons from the same gene. The multiple amplicons can comprise different genetic features such as SNPs. Identification of multiple amplicons on the same gene can be useful for identification of SNPs and/or genetic mobility events (e.g., truncations, translocations, transpositions).

In some embodiments, the probes on the initial substrate can be oligo(dT) and the probes on the replicate substrate can be gene-specific or a combination of gene-specific and oligo(dT).

Synthesis of Stochastic Barcodes on Solid Supports and Substrates

A stochastic barcode can be synthesized on a solid support (e.g., bead). Pre-synthesized stochastic barcodes (e.g., comprising the 5'amine that can link to the solid support) can be attached to solid supports (e.g., beads) through any of a variety of immobilization techniques involving functional group pairs on the solid support and the stochastic barcode. The stochastic barcode can comprise a functional group. The solid support (e.g., bead) can comprise a functional group. The stochastic barcode functional group and the solid support functional group can comprise, for example, biotin, streptavidin, primary amine(s), carboxyl(s), hydroxyl(s), aldehyde(s), ketone(s), and any combination thereof. A stochastic barcode can be tethered to a solid support, for example, by coupling (e.g. using 1-Ethyl-3-(3-dimethylaminopropyl) carbodiimide) a 5' amino group on the stochastic barcode to the carboxyl group of the functionalized solid support. Residual non-coupled stochastic barcodes can be removed from the reaction mixture by performing multiple rinse steps. In some embodiments, the stochastic barcode and solid support are attached indirectly via linker molecules (e.g. short, functionalized hydrocarbon molecules or polyethylene oxide molecules) using similar attachment chemistries. The linkers can be cleavable linkers, e.g. acid-labile linkers or photo-cleavable linkers.

The stochastic barcodes can be synthesized on solid supports (e.g., beads) using any of a number of solid-phase oligonucleotide synthesis techniques, such as phosphodiester synthesis, phosphotriester synthesis, phosphite triester synthesis, and phosphoramidite synthesis. Single nucleotides can be coupled in step-wise fashion to the growing, tethered stochastic barcode. A short, pre-synthesized sequence (or block) of several oligonucleotides can be coupled to the growing, tethered stochastic barcode.

Stochastic barcodes can be synthesized by interspersing step-wise or block coupling reactions with one or more rounds of split-pool synthesis, in which the total pool of synthesis beads is divided into a number of individual smaller pools which are then each subjected to a different coupling reaction, followed by recombination and mixing of the individual pools to randomize the growing stochastic barcode sequence across the total pool of beads. Split-pool synthesis is an example of a combinatorial synthesis process in which a maximum number of chemical compounds are synthesized using a minimum number of chemical coupling steps. The potential diversity of the compound library thus created is determined by the number of unique building blocks (e.g. nucleotides) available for each coupling step, and the number of coupling steps used to create the library. For example, a split-pool synthesis comprising 10 rounds of coupling using 4 different nucleotides at each step will yield $4^{10}=1,048,576$ unique nucleotide sequences. In some embodiments, split-pool synthesis can be performed using enzymatic methods such as polymerase extension or ligation reactions rather than chemical coupling. For example, in each round of a split-pool polymerase extension reaction, the 3' ends of the stochastic barcodes tethered to beads in a given pool can be hybridized with the 5'ends of a set of semi-random primers, e.g. primers having a structure of 5'-$(M)_k$-$(X)_i$—$(N)_j$-3', where $(X)_i$ is a random sequence of nucleotides that is i nucleotides long (the set of primers comprising all possible combinations of $(X)_i$), $(N)_j$ is a specific nucleotide (or series of j nucleotides), and $(M)_k$ is a specific nucleotide (or series of k nucleotides), wherein a different deoxyribonucleotide triphosphate (dNTP) is added to each pool and incorporated into the tethered oligonucleotides by the polymerase.

The number of stochastic barcodes conjugated to or synthesized on a solid support can comprise at least 100, 1000, 10000, or 1000000 or more stochastic barcodes. The number of stochastic barcodes conjugated to or synthesized on a solid support can comprise at most 100, 1000, 10000, or 1000000 or more stochastic barcodes. The number of oligonucleotides conjugated to or synthesized on a solid support such as a bead can be at least 1, 2, 3, 4, 5, 6, 7, 8, 9, or 10-folds more than the number of target nucleic acids in a cell. The number of oligonucleotides conjugated to or synthesized on a solid support such as a bead can be at most 1, 2, 3, 4, 5, 6, 7, 8, 9, or 10-folds more than the number of target nucleic acids in a cell. At least 10, 20, 30, 40, 50, 60, 70, 80, 90 or 100% of the stochastic barcode can be bound by a target nucleic acid. At most 10, 20, 30, 40, 50, 60, 70, 80, 90 or 100% of the stochastic barcode can be bound by a target nucleic acid. At least 1, 2, 3, 4, 5, 6, 7, 8, 9, 10, 20, 30, 40, 50, 60, 70, 80, 90 or 100 or more different target nucleic acids can be captured by the stochastic barcode on the solid support. At most 1, 2, 3, 4, 5, 6, 7, 8, 9, 10, 20, 30, 40, 50, 60, 70, 80, 90 or 100 or more different target nucleic acids can be captured by the stochastic barcode on the solid support.

In some embodiments, stochastic barcodes can be synthesized by randomly distributing a single-stranded DNA mixture onto a substrate pre-coated with primers. The single-stranded DNA can hybridize to the primers. Bridge amplification can be performed to convert the single-stranded DNAs into a cluster. Sequencing can be performed to determine the sequence of the DNA at each cluster on the substrate. A sample can be applied to the substrate, followed by the stochastic barcoding methods of the disclosure.

In some embodiments, barcodes can be synthesized using size and/or electrophoretic mobility. For example, a mixture of stochastic barcodes can be prepared and separated into two-dimensions using gel electrophoresis. The gel can be the substrate.

Methods of Stochastic Barcoding

The disclosure provides for methods for estimating the number of distinct targets at distinct locations in a physical sample (e.g., tissue, organ, tumor, cell). The methods can comprise placing the stochastic barcodes in close proximity with the sample, lysing the sample, associating distinct targets with the stochastic barcodes, amplifying the targets and/or digitally counting the targets. The method can further comprise analyzing and/or visualizing the information obtained from the spatial labels on the stochastic barcodes. In some embodiments, the methods comprise visualizing the plurality of targets in the sample. Mapping the plurality of targets onto the map of the sample can include generating a two dimensional map or a three dimensional map of the sample. The two dimensional map and the three dimensional map can be generated prior to or after stochastically barcoding the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after stochastically barcoding the plurality of targets in the sample. in some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

Figure 3:
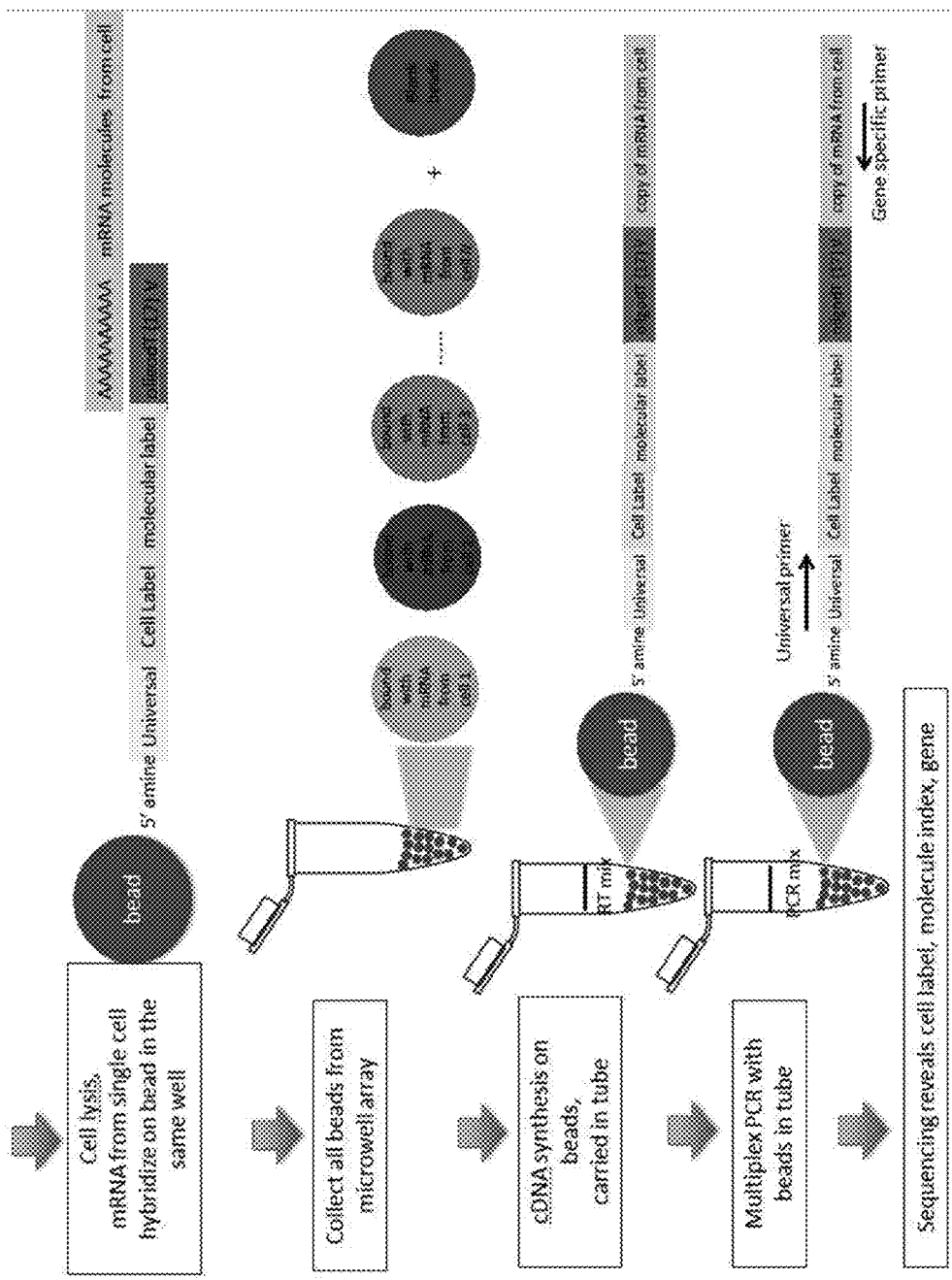
FIG. 3 shows a non-limiting exemplary workflow of stochastic barcoding and digital counting.

FIG. 3 illustrates an exemplary embodiment of the stochastic barcoding method of the disclosure. A sample (e.g., section of a sample, thin slice, and cell) can be contacted with a solid support comprising a stochastic barcode. Targets in the sample can be associated with the stochastic barcodes. The solid supports can be collected. cDNA synthesis can be performed on the solid support. cDNA synthesis can be performed off the solid support. cDNA synthesis can incorporate the label information from the labels in the stochastic barcode into the new cDNA target molecule being synthesized, thereby generating a target-barcode molecule. The target-barcode molecules can be amplified using PCT. The sequence of the targets and the labels of the stochastic barcode on the target-barcode molecule can be determined by sequencing methods.

Contacting a Sample and a Stochastic Barcode

The disclosure provides for methods for contacting a sample (e.g., cells) to a substrate of the disclosure. A sample comprising, for example, a cell, organ, or tissue thin section, can be contacted to stochastic barcodes. The cells can be contacted, for example, by gravity flow wherein the cells can settle and create a monolayer. The sample can be a tissue thin section. The thin section can be placed on the substrate. The sample can be one-dimensional (e.g., form a planar surface). The sample (e.g., cells) can be spread across the substrate, for example, by growing/culturing the cells on the substrate.

When stochastic barcodes are in close proximity to targets, the targets can hybridize to the stochastic barcode. The stochastic barcodes can be contacted at a non-depletable ratio such that each distinct target can associate with a distinct stochastic barcode of the disclosure. To ensure efficient association between the target and the stochastic barcode, the targets can be crosslinked to the stochastic barcode.

Cell Lysis

Following the distribution of cells and stochastic barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g. SDS, Li dodecyl sulfate, Triton X-100, Tween-20, or NP-40), an organic solvent (e.g. methanol or acetone), or digestive enzymes (e.g. proteinase K, pepsin, or trypsin), or any combination thereof. To increase the association of a target and a stochastic barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1M or more Tris HCl. A lysis buffer can comprise at most about 0.01, 0.05, 0.1, 0.5, or 1M or more Tris HCL. A lysis buffer can comprise about 0.1 M Tris HCl. The pH of the lysis buffer can be at least about 1, 2, 3, 4, 5, 6, 7, 8, 9, or 10 or more. The pH of the lysis buffer can be at most about 1, 2, 3, 4, 5, 6, 7, 8, 9, or 10 or more. In some embodiments, the pH of the lysis buffer is about 7.5. The lysis buffer can comprise a salt (e.g., LiCl). The concentration of salt in the lysis buffer can be at least about 0.1, 0.5, or 1M or more. The concentration of salt in the lysis buffer can be at most about 0.1, 0.5, or 1M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001, 0.0005, 0.001, 0.005, 0.01, 0.05, 0.1, 0.5, 1, 2, 3, 4, 5, 6, or 7% or more. The concentration of the detergent in the lysis buffer can be at most about 0.0001, 0.0005, 0.001, 0.005, 0.01, 0.05, 0.1, 0.5, 1, 2, 3, 4, 5, 6, or 7% or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.Lysis can be performed at a temperature of about 4, 10, 15, 20, 25, or 30 C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Stochastic Barcodes to Target Nucleic Acid Molecules

Following lysis of the cells and release of nucleic acid molecules therefrom, the nucleic acid molecules can randomly associate with the stochastic barcodes of the co-localized solid support. Association can comprise hybridization of a stochastic barcode's target recognition region to a complementary portion of the target nucleic acid molecule (e.g., oligo(dT) of the stochastic barcode can interact with a poly(A) tail of a target). The assay conditions used for hybridization (e.g. buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule.

Attachment can further comprise ligation of a stochastic barcode's target recognition region and a portion of the target nucleic acid molecule. For example, the target binding region can comprise a nucleic acid sequence that can be capable of specific hybridization to a restriction site overhang (e.g. an EcoRI sticky-end overhang). The assay procedure can further comprise treating the target nucleic acids with a restriction enzyme (e.g. EcoRI) to create a restriction site overhang. The stochastic barcode can then be ligated to any nucleic acid molecule comprising a sequence complementary to the restriction site overhang. A ligase (e.g., T4 DNA ligase) can be used to join the two fragments.

The labeled targets from a plurality of cells (or a plurality of samples) (e.g., target-barcode molecules) can be subsequently pooled, for example by retrieving the stochastic barcodes and/or the beads to which the target-barcode molecules are attached. The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription

The disclosure provides for a method to create a stochastic target-barcode conjugate using reverse transcription. The stochastic target-barcode conjugate can comprise the stochastic barcode and a complementary sequence of all or a portion of the target nucleic acid (i.e. a stochastically barcoded cDNA molecule). Reverse transcription of the associated RNA molecule can occur by the addition of a reverse transcription primer along with the reverse transcriptase. The reverse transcription primer can be an oligo-dT primer, a random hexanucleotide primer, or a target-specific oligonucleotide primer. Oligo-dT primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A)+ tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular and/or molecular label. The amplification reactions can comprise amplifying at least a portion of a sample tag, a cellular label, a spatial label, a molecular label, a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cellular label, a spatial label, and/or a molecular label.

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a stochastically labeled-amplicon. The labeled-amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cellular label, and/or a molecular label. The stochastically labeled-amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of stochastically labeled targets. The one or more primers can anneal to the 3' end or 5' end of the plurality of stochastically labeled targets. The one or more primers can anneal to an internal region of the plurality of stochastically labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of stochastically labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cellular label, a molecular label, a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total stochastically labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cellular label and molecular index on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more oligonucleotides can comprise a sequence selected from a group consisting of sequences in Table 23. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, stochastically barcoding the plurality of targets in the sample further comprises generating an indexed library of the stochastically barcoded targets. The molecular labels of different stochastic barcodes can be different from one another. Generating an indexed library of the stochastically barcoded targets includes generating a plurality of indexed polynucleotides from the plurality of targets in the sample. For example, for an indexed library of the stochastically barcoded targets comprising a first indexed target and a second indexed target, the label region of the first indexed polynucleotide can differ from the label region of the second indexed polynucleotide by at least one, two, three, four, or five nucleotides. In some embodiments, generating an indexed library of the stochastically barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the stochastically barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Stochastic barcoding can use nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS).

Figure 4:
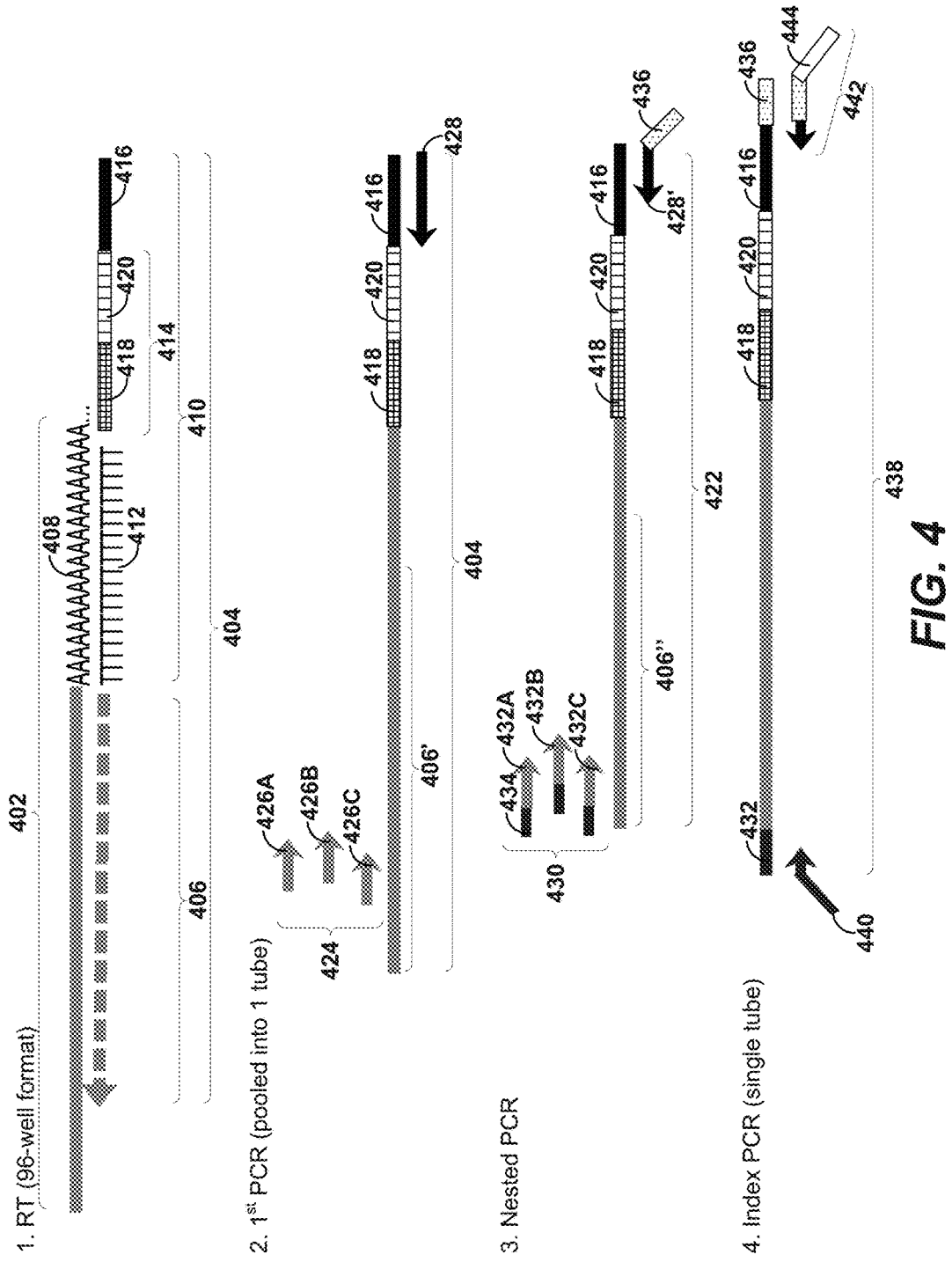
FIG. 4 is a schematic illustration showing a non-limiting exemplary process for generating an indexed library of the stochastically barcoded targets from a plurality of targets.

FIG. 4 is a schematic illustration showing a non-limiting exemplary process of generating an indexed library of the stochastically barcoded targets, for example mRNAs. As shown in step 1, the reverse transcription process can encode each mRNA molecule with a unique molecular label, a spatial label, and a universal PCR site. In particular, RNA molecules 402 can be reverse transcribed to produce labeled cDNA molecules 404, including a cDNA region 406, by the stochastic hybridization of a set of molecular identifier labels 410 to the poly(A) tail region 408 of the RNA molecules 402. Each of the molecular identifier labels 410 can comprise a target-binding region, for example a poly (dT) region 412, a label region 414, and a universal PCR region 416.

In some embodiments, the spatial label can include 3 to 20 nucleotides. In some embodiments, the molecular label can include 3 to 20 nucleotides. In some embodiments, each of the plurality of stochastic barcodes further comprises one or more of a universal label and a cellular label, wherein universal labels are the same for the plurality of stochastic barcodes on the solid support and cellular labels are the same for the plurality of stochastic barcodes on the solid support. In some embodiments, the universal label can include 3 to 20 nucleotides. In some embodiments, the cellular label comprises 3 to 20 nucleotides.

In some embodiments, the label region 414 can include a molecular label 418 and a spatial label 420. In some embodiments, the label region 414 can include one or more of a universal label, a dimension label, and a cellular label. The molecular label 418 can be, or can be about, 1, 2, 3, 4, 5, 6, 7, 8, 9, 10, 20, 30, 40, 50, 60, 70, 80, 90, 100, or a number or a range between any of these values, of nucleotides in length. The spatial label 420 can be, or can be about, 1, 2, 3, 4, 5, 6, 7, 8, 9, 10, 20, 30, 40, 50, 60, 70, 80, 90, 100, or a number or a range between any of these values, of nucleotides in length. The universal label can be, or can be about, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cellular labels are the same for the plurality of stochastic barcodes on the solid support. The dimension label can be, or can be about, 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 414 can comprise 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a molecular label 418 and a spatial label 420. Each label can be, or can be about, 1, 2, 3, 4, 5, 6, 7, 8, 9, 10, 20, 30, 40, 50, 60, 70, 80, 90, 100, or a number or a range between any of these values, of nucleotides in length. A set of molecular identifier labels 410 can contain 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, molecular identifier labels 410. And the set of molecular identifier labels 410 can, for example, each contain a unique label region 414. The labeled cDNA molecules 404 can be purified to remove excess molecular identifier labels 410. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 414. In particular, the labeled cDNA molecules 404 can be amplified to produce nested PCR labeled amplicons 422. Amplification can comprise multiplex PCR amplification. Amplification can comprise a multiplex PCR amplification with 96 multiplex primers in a single reaction volume. In some embodiments, multiplex PCR amplification can utilize 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise $1^{st}$ PCR primer pool 424 of custom primers 426A-C targeting specific genes and a universal primer 428. The custom primers 426 can hybridize to a region within the cDNA portion 406' of the labeled cDNA molecule 404. The universal primer 428 can hybridize to the universal PCR region 416 of the labeled cDNA molecule 404.

As shown in step 3 of FIG. 4, products from PCR amplification in step 2 can be amplified with a nested PCR primers pool and a $2^{nd}$ universal PCR primer. Nested PCR can minimize PCR amplification bias. In particular, the nested PCR labeled amplicons 422 can be further amplified by nested PCR. The nested PCR can comprise multiplex PCR with nested PCR primers pool 430 of nested PCR primers 432A-C and a $2^{nd}$ universal PCR primer 428' in a single reaction volume. The nested PCR primer pool 428 can contain, or contain about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 430. The nested PCR primers 432 can contain an adaptor 434 and hybridize to a region within the cDNA portion 406" of the labeled amplicon 422. The universal primer 428' can contain an adaptor 436 and hybridize to the universal PCR region 416 of the labeled amplicon 422. Thus, step 3 produces adaptor-labeled amplicon 438. In some embodiments, nested PCR primers 432 and the $2^{nd}$ universal PCR primer 428' may not contain the adaptors 434 and 436. The adaptors 434 and 436 can instead be ligated to the products of nested PCR to produce adaptor-labeled amplicon 438.

As shown in step 4, PCR products from step 3 can be PCR amplified for sequencing using library amplification primers. In particular, the adaptors 434 and 436 can be used to conduct one or more additional assays on the adaptor-labeled amplicon 438. The adaptors 434 and 436 can be hybridized to primers 440 and 442. The one or more primers 440 and 442 can be PCR amplification primers. The one or more primers 440 and 442 can be sequencing primers. The one or more adaptors 434 and 436 can be used for further amplification of the adaptor-labeled amplicons 438. The one or more adaptors 434 and 436 can be used for sequencing the adaptor-labeled amplicon 438. The primer 442 can contain a plate index 444 so that amplicons generated using the same set of molecular identifier labels 408 can be sequenced in one sequencing reaction using NGS.

Sequencing

In some embodiments, estimating the number of the plurality of targets using the molecular label includes determining sequences of the spatial labels and molecular labels of the plurality of the stochastic labels and counting the number of the molecular labels with distinct sequences. Determining the sequences of the spatial labels and the molecular labels of the plurality of the stochastic barcodes can include sequencing some or all of the plurality of stochastic barcodes. Sequencing some or all of the plurality of stochastic barcodes can include generating sequences each with a read length of 100 or more bases.

Determining the number of different stochastically labeled nucleic acids can comprise determining the sequence of the labeled target, the spatial label, the molecular label, the sample label, and the cellular label or any product thereof (e.g. labeled-amplicons, labeled-cDNA molecules). An amplified target can be subjected to sequencing. Determining the sequence of the stochastically labeled nucleic acid or any product thereof can comprise conducting a sequencing reaction to determine the sequence of at least a portion of a sample label, a spatial label, a cellular label, a molecular label, at least a portion of the stochastically labeled target, a complement thereof, a reverse complement thereof, or any combination thereof.

Determination of the sequence of a nucleic acid (e.g. amplified nucleic acid, labeled nucleic acid, cDNA copy of a labeled nucleic acid, etc.) can be performed using variety of sequencing methods including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, or single template molecule OLA using a ligated circular padlock probe and a rolling circle amplification (RCA) readout), and the like.

In some embodiments, determining the sequence of the labeled nucleic acid or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the labeled nucleic acid or any product thereof can be determined by electron microscopy or a chemical-sensitive field effect transistor (chemFET) array.

High-throughput sequencing methods, such as cyclic array sequencing using platforms such as Roche 454, Illumina Solexa, ABI-SOLiD, ION Torrent, Complete Genomics, Pacific Bioscience, Helicos, or the Polonator platform, can also be utilized. In some embodiment, sequencing can comprise MiSeq sequencing. In some embodiment, sequencing can comprise HiSeq sequencing.

The stochastically labeled targets can comprise nucleic acids representing from about 0.01% of the genes of an organism's genome to about 100% of the genes of an organism's genome. For example, about 0.01% of the genes of an organism's genome to about 100% of the genes of an organism's genome can be sequenced using a target complimentary region comprising a plurality of multimers by capturing the genes containing a complimentary sequence from the sample. In some embodiments, the labeled nucleic acids comprise nucleic acids representing from about 0.01% of the transcripts of an organism's transcriptome to about 100% of the transcripts of an organism's transcriptome. For example, about 0.501% of the transcripts of an organism's transcriptome to about 100% of the transcripts of an organism's transcriptome can be sequenced using a target complimentary region comprising a poly-T tail by capturing the mRNAs from the sample.

Determining the sequences of the spatial labels and the molecular labels of the plurality of the stochastic barcodes can include sequencing 0.00001%, 0.0001%, 0.001%, 0.01%, 0.1%, 1%, 2%, 3%, 4%, 5%, 6%, 7%, 8%, 9%, 10%, 20%, 30%, 40%, 50%, 60%, 70%, 80%, 90%, 99%, 100%, or any number or range between two of these values, of the plurality of stochastic barcodes. Determining the sequences of the spatial labels and the molecular labels of the plurality of the stochastic barcodes can include sequencing 1, 10, 20, 30, 40, 50, 60, 70, 80, 90, 100, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or any number or range between two of these values, of the plurality of stochastic barcodes. Sequencing some or all of the plurality of stochastic barcodes can include generating sequences each with a read length of 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or any number or range between two of these values, of nucleotides or bases.

Sequencing can comprise sequencing at least about 10, 20, 30, 40, 50, 60, 70, 80, 90, 100 or more nucleotides or base pairs of the labeled nucleic acid. Sequencing can comprise sequencing at least about 200, 300, 400, 500, 600, 700, 800, 900, 1,000 or more nucleotides or base pairs of the labeled nucleic acid. Sequencing can comprise sequencing at least about 1,500; 2,000; 3,000; 4,000; 5,000; 6,000; 7,000; 8,000; 9,000; or 10,000 or more nucleotides or base pairs of the labeled nucleic acid.

Sequencing can comprise at least about 200, 300, 400, 500, 600, 700, 800, 900, 1,000 or more sequencing reads per run. In some embodiments, sequencing comprises sequencing at least about 1,500; 2,000; 3,000; 4,000; 5,000; 6,000; 7,000; 8,000; 9,000; or 10,000 or more sequencing reads per run. Sequencing can comprise less than or equal to about 1,600,000,000 sequencing reads per run. Sequencing can comprise less than or equal to about 200,000,000 reads per run.

Samples

A sample for use in the method of the disclosure can comprise one or more cells. A sample can refer to one or more cells. In some embodiments, the plurality of cells can include one or more cell types. At least one of the one or more cell types can be brain cell, heart cell, cancer cell, circulating tumor cell, organ cell, epithelial cell, metastatic cell, benign cell, primary cell, circulatory cell, or any combination thereof. In some embodiments, the cells are cancer cells excised from a cancerous tissue, for example, breast cancer, lung cancer, colon cancer, prostate cancer, ovarian cancer, pancreatic cancer, brain cancer, melanoma and non-melanoma skin cancers, and the like. In some embodiments, the cells are derived from a cancer but collected from a bodily fluid (e.g. circulating tumor cells). Non-limiting examples of cancers can include, adenoma, adenocarcinoma, squamous cell carcinoma, basal cell carcinoma, small cell carcinoma, large cell undifferentiated carcinoma, chondrosarcoma, and fibrosarcoma. The sample can include a tissue, a cell monolayer, fixed cells, a tissue section, or any combination thereof. The sample can include a biological sample, a clinical sample, an environmental sample, a biological fluid, a tissue, or a cell from a subject. The sample can be obtained from a human, a mammal, a dog, a rat, a mouse, a fish, a fly, a worm, a plant, a fungus, a bacterium, a virus, a vertebrate, or an invertebrate.

In some embodiments, the cells are cells that have been infected with virus and contain viral oligonucleotides. In some embodiments, the viral infection can be caused by a virus selected from the group consisting of double-stranded DNA viruses (e.g. adenoviruses, herpes viruses, pox viruses), single-stranded (+ strand or "sense") DNA viruses (e.g. parvoviruses), double-stranded RNA viruses (e.g. reoviruses), single-stranded (+ strand or sense) RNA viruses (e.g. picornaviruses, togaviruses), single-stranded (− strand or antisense) RNA viruses (e.g. orthomyxoviruses, rhabdoviruses), single-stranded ((+ strand or sense) RNA viruses with a DNA intermediate in their life-cycle) RNA-RT viruses (e.g. retroviruses), and double-stranded DNA-RT viruses (e.g. hepadnaviruses). Exemplary viruses can include, but are not limited to, SARS, HIV, coronaviruses, Ebola, Malaria, Dengue, Hepatitis C, Hepatitis B, and Influenza.

In some embodiments, the cells are bacteria. These can include either gram-positive or gram-negative bacteria. Examples of bacteria that can be analyzed using the disclosed methods, devices, and systems include, but are not limited to, *Actinomedurae, Actinomyces israelii, Bacillus anthracis, Bacillus cereus, Clostridium botulinum, Clostridium difficile, Clostridium perfringens, Clostridium tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumoniae* and the like. Gram negative bacteria include, but are not limited to, *Afipia felis, Bacteroides, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis* and the like. Other bacteria can include *Myobacterium avium, Myobacterium leprae, Myobacterium tuberculosis, Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium, Meningococci* and the like.

In some embodiments, the cells are fungi. Non-limiting examples of fungi that can be analyzed using the disclosed methods, devices, and systems include, but are not limited to, *Aspergilli, Candidae, Candida albicans, Coccidioides immitis, Cryptococci*, and combinations thereof.

In some embodiments, the cells are protozoans or other parasites. Examples of parasites to be analyzed using the methods, devices, and systems of the present disclosure include, but are not limited to, *Balantidium coli, Cryptosporidium parvum, Cyclospora cayatanensis, Encephalitozoa, Entamoeba histolytica, Enterocytozoon bieneusi, Giardia lamblia, Leishmaniae, Plasmodii, Toxoplasma gondii, Trypanosomae, trapezoidal amoeba*, worms (e.g., helminthes), particularly parasitic worms including, but not limited to, Nematoda (roundworms, e.g., whipworms, hookworms, pinworms, ascarids, filarids and the like), Cestoda (e.g., tapeworms).

As used herein, the term "cell" can refer to one or more cells. In some embodiments, the cells are normal cells, for example, human cells in different stages of development, or human cells from different organs or tissue types (e.g. white blood cells, red blood cells, platelets, epithelial cells, endothelial cells, neurons, glial cells, fibroblasts, skeletal muscle cells, smooth muscle cells, gametes, or cells from the heart, lungs, brain, liver, kidney, spleen, pancreas, thymus, bladder, stomach, colon, small intestine). In some embodiments, the cells can be undifferentiated human stem cells, or human stem cells that have been induced to differentiate. In some embodiments, the cells can be fetal human cells. The fetal human cells can be obtained from a mother pregnant with the fetus. In some embodiments, the cells are rare cells. A rare cell can be, for example, a circulating tumor cell (CTC), circulating epithelial cell, circulating endothelial cell, circulating endometrial cell, circulating stem cell, stem cell, undifferentiated stem cell, cancer stem cell, bone marrow cell, progenitor cell, foam cell, mesenchymal cell, trophoblast, immune system cell (host or graft), cellular fragment, cellular organelle (e.g. mitochondria or nuclei), pathogen infected cell, and the like.

In some embodiments, the cells are non-human cells, for example, other types of mammalian cells (e.g. mouse, rat, pig, dog, cow, or horse). In some embodiments, the cells are other types of animal or plant cells. In other embodiments, the cells can be any prokaryotic or eukaryotic cells.

In some embodiments, a first cell sample is obtained from a person not having a disease or condition, and a second cell sample is obtained from a person having the disease or condition. In some embodiments, the persons are different. In some embodiments, the persons are the same but cell samples are taken at different time points. In some embodiments, the persons are patients, and the cell samples are patient samples. The disease or condition can be a cancer, a bacterial infection, a viral infection, an inflammatory disease, a neurodegenerative disease, a fungal disease, a parasitic disease, a genetic disorder, or any combination thereof.

In some embodiments, cells suitable for use in the presently disclosed methods can range in size from about 2 micrometers to about 100 micrometers in diameter. In some embodiments, the cells can have diameters of at least 2 micrometers, at least 5 micrometers, at least 10 micrometers, at least 15 micrometers, at least 20 micrometers, at least 30 micrometers, at least 40 micrometers, at least 50 micrometers, at least 60 micrometers, at least 70 micrometers, at least 80 micrometers, at least 90 micrometers, or at least 100 micrometers. In some embodiments, the cells can have diameters of at most 100 micrometers, at most 90 micrometers, at most 80 micrometers, at most 70 micrometers, at most 60 micrometers, at most 50 micrometers, at most 40 micrometers, at most 30 micrometers, at most 20 micrometers, at most 15 micrometers, at most 10 micrometers, at most 5 micrometers, or at most 2 micrometers. The cells can have a diameter of any value within a range, for example from about 5 micrometers to about 85 micrometers. In some embodiments, the cells have diameters of about 10 micrometers.

In some embodiments the cells are sorted prior to associating a cell with a bead. For example the cells can be sorted by fluorescence-activated cell sorting or magnetic-activated cell sorting, or more generally by flow cytometry. The cells can be filtered by size. In some embodiments a retentate contains the cells to be associated with the bead. In some embodiments the flow through contains the cells to be associated with the bead.

A sample can refer to a plurality of cells. The sample can refer to a monolayer of cells. The sample can refer to a thin section (e.g., tissue thin section). The sample can refer to a solid or semi-solid collection of cells that can be place in one dimension on an array.

Resolution of Spatial Labels

The methods of the disclosure relate to the relationship between the resolution of spatial labels and the size and/or spacing of the stochastic barcodes (e.g., cells). When samples are larger the spacing of spatial labels, the resolution of targets in the sample can be higher. When samples are smaller than the spacing of spatial labels the resolution of the location of targets in the sample can be lower.

The stochastic barcodes can be spaced at a distance at least 5, 10, 15, 20, 25, 30, 35, 40, 45, 50, 55, 60, 65, 70, 75, 80, 85, 90, 95, or 100% of the longest dimension of the sample. The stochastic barcodes can be spaced at a distance at most 5, 10, 15, 20, 25, 30, 35, 40, 45, 50, 55, 60, 65, 70, 75, 80, 85, 90, 95, or 100% of the longest dimension of the sample. The stochastic barcodes can be spaced at a distance at least 5, 10, 15, 20, 25, 30, 35, 40, 45, 50, 55, 60, 65, 70, 75, 80, 85, 90, 95, or 100% of the shortest dimension of the sample. The stochastic barcodes can be spaced at a distance at most 5, 10, 15, 20, 25, 30, 35, 40, 45, 50, 55, 60, 65, 70, 75, 80, 85, 90, 95, or 100% of the shortest dimension of the sample.

A sample can associate with one or more types of stochastic barcodes, wherein each type of stochastic barcode comprises a different spatial label. A sample can associate with at least 1, 2, 3, 4, 5, 6, 7, 8, 9, or 10 or more types of stochastic barcodes (e.g., different spatial labels). A sample can associate with at most 1, 2, 3, 4, 5, 6, 7, 8, 9, or 10 or more types of stochastic barcodes (e.g., different spatial labels). The number of types of stochastic barcodes to which a sample can associate with can be related to the spacing of the barcodes relative to the size of the sample.

In some embodiments, the methods of the disclosure relate to the relationship between the resolution of spatial labels and the spacing of the samples. When samples are spaced far apart (e.g., on a substrate), the spatial resolution of the targets in the sample can be higher because diffusion between samples may not contaminate the samples. When samples are spaced close together (e.g., on a substrate), the spatial resolution of the targets in the sample can be lower because diffusion of targets between the samples can contaminate a neighboring sample.

The samples can be spaced at least 1, 100, 200, 300, 400, 500, 600, 700, 800, 900 or more micrometers apart. The samples can be spaced at most 1, 100, 200, 300, 400, 500, 600, 700, 800, 900 or more micrometers apart. The samples can be spaced at least 1, 100, 200, 300, 400, 500, 600, 700, 800, 900 or more millimeters apart. The samples can be spaced at most 1, 100, 200, 300, 400, 500, 600, 700, 800, 900 or more millimeters apart. The samples can be spaced at least 1, 100, 200, 300, 400, 500, 600, 700, 800, 900 or more meters apart. The samples can be spaced at most 1, 100, 200, 300, 400, 500, 600, 700, 800, 900 or more meters apart.

Targets from a sample can diffuse at least 1, 2, 3, 4, 5, 6, 7, 8, 9, 10, 15, 20, 25, 30, 35, 40, 45, 50, 55, 60, 65, 70, 75, 80, 85, 90, 95, or 100 or more nanometers. Targets from a sample can diffuse at most 1, 2, 3, 4, 5, 6, 7, 8, 9, 10, 15, 20, 25, 30, 35, 40, 45, 50, 55, 60, 65, 70, 75, 80, 85, 90, 95, or 100 or more nanometers. Targets from a sample can diffuse at least 0.1, 0.2, 0.3, 0.4, 0.5, 0.6, 0.7, 0.8, 0.9, or 1 or more millimeters. Targets from a sample can diffuse at most 0.1, 0.2, 0.3, 0.4, 0.5, 0.6, 0.7, 0.8, 0.9, or 1 or more millimeters.

Methods for Spatial Identification of a Nucleic Acid in a Sample

Disclosed herein are methods for determining spatial locations of a plurality of targets in a sample. In some embodiments, the methods include: imaging the sample to generate a sample image; stochastically barcoding the plurality of targets in the sample using a plurality of stochastic barcodes to generate stochastically barcoded targets, wherein each of the plurality of stochastic barcodes comprises a spatial label; and identifying the spatial location of each of the plurality of targets using the spatial label. Identifying the spatial location of each of the plurality of targets using the spatial label can include correlating the sample image with the spatial labels of the plurality of targets in the sample. Imaging the sample can include staining the sample with a stain, wherein the stain is a fluorescent stain, a negative stain, an antibody stain, or any combination thereof. Imaging the sample can include imaging the sample using optical microscopy, electron microscopy, confocal microscopy, fluorescence microscopy, or any combination thereof. Correlating the sample image with the spatial labels of the plurality of targets in the sample can include overlaying the sample image with the spatial labels of the plurality of targets in the sample. The sample can include a biological sample, a clinical sample, an environmental sample, a biological fluid, a tissue, or a cell from a subject. In some embodiments, the methods can include determining genotype, phenotype, or one or more genetic mutations of the subject based on the spatial labels of the plurality of targets in the sample. In some embodiments, the methods can include predicting susceptibility of the subject to one or more diseases. At least one of the one or more diseases can be cancer or a hereditary disease. The sample can include a plurality of cells and the plurality of targets can be associated with the plurality of cells. The plurality of cells can include one or more cell types. In some embodiments, the methods can include determining cell types of the plurality of cells in the sample. The drug can be chosen based on predicted responsiveness of the cell types of the plurality of cells in the sample.

Imaging

The sample contacted to the substrate can be analyzed (e.g., with immunohistochemistry, staining and/or imaging). Exemplary methods of immunohistochemistry can comprise a step of reacting a labeled probe biological substance obtained by introducing a label into a substance capable of recognizing a biological substance to be detected to a tissue section, to visualize the biological substance to be detected present on the tissue section via a specific binding reaction between the biological substances.

For histology specimens, the tissue pieces can be fixed in a suitable fixative, typically formalin, and embedded in melted paraffin wax. The wax block can be cut on a microtome to yield a thin slice of paraffin containing the tissue. The specimen slice can be applied to a substrate, air dried, and heated to cause the specimen to adhere to the glass slide. Residual paraffin can be dissolved with a suitable solvent, typically xylene, toluene, or others. These so-called deparaffinizing solvents can be removed with a washing-dehydrating type reagent prior to staining. Slices can be prepared from frozen specimens, fixed briefly in 10% formalin, then infused with dehydrating reagent. The dehydrating reagent can be removed prior to staining with an aqueous stain.

In some embodiments, the Papanicolaou staining technique can be used (e.g., a progressive stain and/or hematoxylineosin [H&E], i.e., a regressive stain). HE (hematoxylin-eosin) stain uses hematoxylin and eosin as a dye. Hematoxylin is a blue-violet dye, and has a property of staining basophilic tissues such as cell nuclei, bone tissues, part of cartilage tissues, and serous components. Eosin is a red to pink dye, and has a property of staining eosinophilic tissues such as cytoplasm, connective tissues of the softtissue, red blood cells, fibrin, and endocrine granules.

Immunohistochemistry (IHC) can be referred to as "immunological staining" due to the process of color development for visualizing an antigen-antibody reaction which is otherwise invisible (hereinafter, the term "immunohistochemical staining" can be used for immunohistochemistry). Lectin staining is a technique that can use a property of lectin of binding to a specific sugar chain in a non-immunological and specific manner in order to detect a sugar chain in a tissue specimen using lectin.

HE staining, immunohistochemistry and lectin staining can be used for detecting a location of, for example, cancer cells in a cell specimen. For example, when it is desired to confirm a location of cancer cells in a cell specimen, a pathologist, in order to determine the presence or absence of cancer cells in the cell specimen, can prepare tissue sections and place them on a substrate of the disclosure. The section on the array can be subjected to HE staining, imaging, or any immunohistochemical analysis in order to obtain its morphological information and/or any other identifying features (such as presence or absence of rare cells). The sample can be lysed and the presence or absence of nucleic acid molecules can be determined using the methods of the disclosure. The nucleic acid information can be compared (e.g., spatially compared) to the image, thereby indicating the spatial location of nucleic acids in a sample.

In some embodiments, the tissue is stained with a staining enhancer (e.g., a chemical penetrant enhancer). Examples of tissue chemical penetrant enhancers that facilitate penetration of the stain into the tissue include, but are not limited to, polyethylene glycol (PEG), surfactants such as polyoxyethylenesorbitans, polyoxyethylene ethers (polyoxyethylenesorbitan monolaurate (Tween 20) and other Tween derivatives, polyoxyethylene 23 lauryl ether (Brij 35), Triton X-100, Brij 35, Nonidet P-40, detergent-like substances such as lysolecithins, saponins, non-ionic detergents such as TRITON® X-100, etc., aprotic solvents such as dimethyl sulfoxide (DMSO), ethers such as tetrahydrofuran, dioxane, etc.; esters such as ethyl acetate, butyl acetate, isopropyl acetate; hydrocarbons such as toluene, chlorinated solvents such as dichloromethane, dichloroethane, chlorobenzene, etc.; ketones such as acetone, nitriles such as acetonitrile, and/or other agents that increase cell membrane permeability.

In some embodiments, a composition is provided that facilitates staining of a mammalian tissue sample. The composition can comprise a stain, such as hematoxylin, or hematoxylin and eosin-Y, at least one tissue chemical penetrant enhancer, such as a surfactant, an aprotic solvent, and/or PEG, or any combination thereof.

In some embodiments, the sample is imaged (e.g., either before or after IHC or without IHC). Imaging can comprise microscopy such as bright field imaging, oblique illumination, dark field imaging, dispersion staining, phase contrast, differential interference contrast, interference reflection microscopy, fluorescence, confocal, electron microscopy, transmission electron microscopy, scanning electron microscopy, and single plane illumination, or any combination thereof. Imaging can comprise the use of a negative stain (e.g., nigrosin, ammonium molybdate, uranyl acetate, uranyl formate, phosphotungstic acid, osmium tetroxide). Imaging can comprise the use of heavy metals (e.g., gold, osmium) that can scatter electrons.

Imaging can comprise imaging a portion of the sample (e.g., slide/array). Imaging can comprise imaging at least 10, 20, 30, 40, 50, 60, 70, 80, 90, or 100% of the sample. Imaging can comprise imaging at most 10, 20, 30, 40, 50, 60, 70, 80, 90, or 100% of the sample. Imaging can be done in discrete steps (e.g., the image may not need to be contiguous). Imaging can comprise taking at least 1, 2, 3, 4, 5, 6, 7, 8, 9, or 10 or more different images. Imaging can comprise taking at most 1, 2, 3, 4, 5, 6, 7, 8, 9, or 10 or more different images.

Detection

The substrate surface can be contacted with one or more targets under conditions that promote specific, high-affinity binding (i.e., hybridization) of the target to one or more of the probes. The target nucleic acids can hybridize with complementary nucleic acids of the known oligonucleotide optical labels and thus, information about the target samples can be obtained. The targets can be labeled with an optically detectable label, such as a fluorescent tag or fluorophore, so that the targets are detectable with scanning equipment after a hybridization assay. The targets can be labeled either prior to, during, or even after the hybridization protocol, depending on the labeling system chosen, such that the fluorophore will associate only with probe-bound hybridized targets.

The targets (e.g., molecules, amplified molecules) can be detected, for example, using detection probes (e.g., fluorescent probes). The array can be hybridized with at least 1, 2, 3, 4, 5, 6, 7, 8, 9, or 10 or more detection probes. The array can be hybridized with at most 1, 2, 3, 4, 5, 6, 7, 8, 9, or 10 or more detection probes. In some embodiments, the array is hybridized with 4 detection probes.

The detection probes can comprise a sequence complementary to a sequence of a gene of interest. The length of the detection probe can be at least 1, 2, 3, 4, 5, 6, 7, 8, 9, 10, 11, 12, 13, 14, or 15 or more nucleotides. The length of the detection probe can be at most 1, 2, 3, 4, 5, 6, 7, 8, 9, 10, 11, 12, 13, 14, or 15 or more nucleotides. The detection probes can comprise a sequence that is perfectly complementary to a sequence in a gene of interest (e.g., target). The detection probes can comprise a sequence that is imperfectly complementary to a sequence in a gene of interest (e.g., target). The detection probes can comprise a sequence with at least 1, 2, 3, 4, 5, 6, 7, 8, 9, or 10 or more mismatches to the sequence of the gene of interest. The detection probes can comprise a sequence with at most 1, 2, 3, 4, 5, 6, 7, 8, 9, or 10 or more mismatches to the sequence of the gene of interest.

The detection probes can comprise a detectable label. Exemplary detectable labels can comprise a fluorophore, chromophore, small molecule, nanoparticle, hapten, enzyme, antibody, and magnetic property, or any combination thereof.

Hybridized probes can be imaged. The image can be used to determine the relative expression level of the genes of interest based on the intensity of the detectable signal (e.g., fluorescent signal). Scanning laser fluorescence microscopes or readers can be used to acquire digital images of the emitted light from substrate (e.g., microarray). A focused light source (usually a laser) can be scanned across the hybridized substrate causing the hybridized areas to emit an optical signal, such as fluorescence. The fluorophore-specific fluorescence data can be collected and measured during the scanning operation, and then an image of the substrate can be reconstructed via appropriate algorithms, software and computer hardware. The expected or intended locations of probe nucleic acid features can then be combined with the fluorescence intensities measured at those locations, to yield the data that is then used to determine gene expression levels or nucleic acid sequence of the target samples. The process of collecting data from expected probe locations can be referred to as "feature extraction". The digital images can be comprised of several thousand to hundreds of millions of pixels that typically range in size from 5 to 50 microns. Each pixel in the digital image can be represented by a 16 bit integer, allowing for 65,535 different grayscale values. The reader can sequentially acquire the pixels from the scanned substrate and writes them into an image file which can be stored on a computer hard drive. The substrates can contain several different fluorescently tagged probe DNA samples at each spot location. The scanner repeatedly scans the entire substrate with a laser of the appropriate wavelength to excite each of the probe DNA samples and store them in their separate image files. The image files are analyzed and subsequently viewed with the aid of a programmed computer.

The substrate can be imaged with a confocal laser scanner. The scanner can scan the substrate slide to produce one image for each dye used by sequentially scanning the with a laser of a proper wavelength for the particular dye. Each dye can have a known excitation spectra and a known emission spectra. The scanner can include a beam splitter which reflects a laser beam towards an objective lens which, in turn, focuses the beam at the surface of slide to cause fluorescence spherical emission. A portion of the emission can travel back through the lens and the beam splitter. After traveling through the beam splitter, the fluorescence beam can be reflected by a mirror, travels through an emission filter, a focusing detector lens and a central pinhole.

Correlation Between Probing and Imaging Data

The data from the substrate scan can be correlated to the image of the unlysed sample on the substrate. The data can be overlayed thereby generating a map. A map of the location of targets from a sample can be constructed using information generated using the methods described herein. The map can be used to locate a physical location of a target. The map can be used to identify the location of multiple targets. The multiple targets can be the same species of target, or the multiple targets can be multiple different targets. For example a map of a brain can be constructed to show the amount and location of multiple targets.

The map can be generated from data from a single sample. The map can be constructed using data from multiple samples, thereby generating a combined map. The map can be constructed with data from tens, hundreds, and/or thousands of samples. A map constructed from multiple samples can show a distribution of targets associated with regions common to the multiple samples. For example, replicated assays can be displayed on the same map. At least 1, 2, 3, 4, 5, 6, 7, 8, 9, or 10 or more replicates can be displayed (e.g., overlaid) on the same map. At most 1, 2, 3, 4, 5, 6, 7, 8, 9, or 10 or more replicates can be displayed (e.g., overlaid) on the same map. The spatial distribution and number of targets can be represented by a variety of statistics.

Combining data from multiple samples can increase the locational resolution of the combined map. The orientation of multiple samples can be registered by common landmarks and/or x-y positions on the array, wherein the individual locational measurements across samples are at least in part non-contiguous. Multiplexing the above approach will allow for high resolution maps of target nucleic acids in a sample.

The data analysis and correlation can be useful for determining the presence and/or absence of a specific cell type (e.g., rare cell, cancer cell). The data correlation can be useful for determining the relative ratios of target nucleic acids in distinct locations either within a cell, or within a sample.

The methods and compositions disclosed herein can be companion diagnostics for a medical professional (e.g., a pathologist) wherein a subject can be diagnosed by visually looking at a pathology image and correlating the image to genetic expression (e.g., identification of expression of oncogenes). The methods and compositions can be useful for identifying a cell from a population of cells, and determining the genetic heterogeneity of the cells within a sample. The methods and compositions can be useful for determining the genotype of a sample.

The disclosure provides for methods for making replicates of substrates. The substrates can be reprobed with different probes for different genes of interest, or to selectively choose specific genes. For example, a sample can be placed on a substrate comprising a plurality of oligo(dT) probes. mRNAs can hybridize to the probes. Replicate substrates comprising oligo(dT) probes can be contacted to the initial slide and make replicates of the mRNAs. Replicate substrates comprising RNA gene-specific probes can be contacted to the initial slide to make a replicate.

The mRNA can be reverse transcribed into cDNA. The cDNA can be homopolymer tailed and/or amplified (e.g., via bridge amplification). The array can be contacted with a replicate array. The replicate array can comprise gene-specific probes that can bind to the cDNAs of interest. The replicate array can comprise polyA probes that can bind to cDNAs with a polyadenylation sequence.

The number of replicates that can be made can be at least 1, 2, 3, 4, 5, 6, 7, 8, 9, or 10 or more. The number of replicates that can be made can be at most 1, 2, 3, 4, 5, 6, 7, 8, 9, or 10 or more.

In some embodiments, the initial substrate comprises a plurality of gene-specific probes and the replicate substrate comprises the same gene-specific probes, or different probes that correspond to the same genes as the gene-specific probes.

Stochastic Barcoding with Physical Separation of Samples

In some embodiments, the sample can be physically divided or can be intact during stochastically barcoding the plurality of targets in the sample. The spatial locations of the plurality of targets in the sample can be on a surface of the sample, inside the sample, subcellularly in the sample, or any combination thereof. In some embodiments, stochastic barcoding the plurality of targets in the sample can be performed on the surface of the sample, subcellularly in the sample, inside the sample, or any combination thereof.

A sample can be physically separated into different containers. Physical separation can be accomplished by dissection, for example by physically cutting a sample. Physical separation can be accomplished by sectioning, for example sectioning with a microtome. Physical separation can be accomplished by using a blade grid (e.g., a substrate wherein the edges of containers in the substrate are sharp such that they can cut a sample, and wherein the pieces of the cut sample can fall into the containers on the substrate). A blade grid can simultaneously separate and physically isolate the parts of the samples.

The process of physical separation can preserve information about the physically separated sample. Information preservation can occur by associating a known part of the sample with a particular spatial label and/or container. The containers can comprise spatial labels which can be used to represent the original physical relationships present before the sample was separated. The spatial labels can then be associated with targets within the parts of the physically separated samples. In this way targets from an identifiable location within the sample can be stochastically labeled and digitally counted.

In a basic example, a sample, for example a solid tissue, can be bisected along a midsagittal plane. The right half of the organ can be placed in one container. The left half of the organ can be placed in a second container. A pool of non-depletable labels can be associated with targets in each container. The labels can be used to stochastically label targets within the sample. The labels can comprise a spatial label which can be used to identify which targets were in each container. The labeled targets from each container can be recombined for analysis. The analysis can include an amplification step. The amplified labeled-targets can be sequenced or hybridized to an array for analysis. The data generated from the analysis can include a stochastic count of the number of starting targets and, for each target, spatial information regarding whether the target was to the left or right of the midsagittal bisection.

A sample can be physically separated into more than two sections. A sample can be divided into at least 2, 3, 4, 5, 6, 7, 8, 9, 10 or more sections. A sample can be divided into at most 2, 3, 4, 5, 6, 7, 8, 9, 10 or more sections. A sample can be divided into hundreds of sections. A sample can be divided into at least 100, 200, 300, 400, 500, 600, 700, 800, or 900 or more sections. A sample can be divided into at most 100, 200, 300, 400, 500, 600, 700, 800, or 900 or more sections. A sample can be divided into thousands of sections. A sample can be divided into at least 1000, 10000, 20000, 30000, 40000, 50000, 60000, 70000, 80000 or 90000 or more sections. A sample can be divided into at most 1000, 10000, 20000, 30000, 40000, 50000, 60000, 70000, 80000 or 90000 or more sections. A sample can be divided into 16, 32, 48, 96, or 384 sections. The higher the number of sections the sample is divided into the greater the spatial resolution imparted by the spatial labels.

Figure 5:
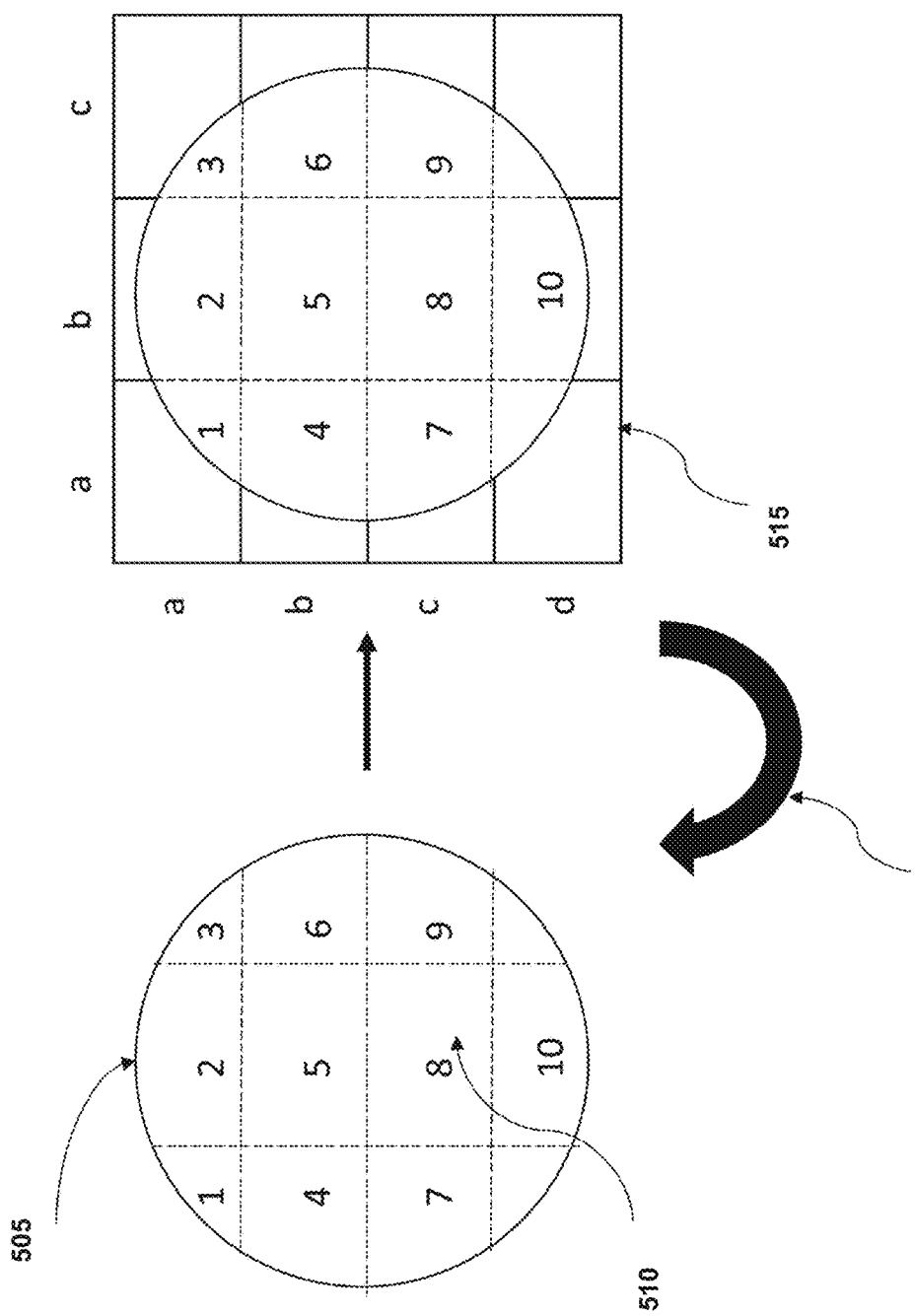
FIG. 5 illustrates a non-limiting exemplary embodiment for determining spatial locations of targets in a sample by maintaining physiological orientation of sections of the sample.

The sections (e.g., of the solid tissue and/or comprising the targets) can be arranged such that a physical relationship of sections is similar to the physical relationship between containers on a substrate (e.g., a grid). For example a target that is in a "top right" section of a sample can be located in a "top right" container. This can allow for a sample to be directly applied to a substrate to preserve the physical relationship between the sections of the sample (e.g., solid tissue). FIG. 5 illustrates how a solid tissue 505 can be divided into sections 510 (e.g., sections 1-10). The sections can be placed on a substrate 515 (e.g., grid). The sections 510 of the solid tissue 505 can be placed onto a specific location within the substrate 515, wherein the specific location is a replicated map of the solid tissue 505. The placement of sections of a solid tissue onto the substrate can be performed in two or three dimensions. FIG. 5 illustrates an exemplary embodiment of a two dimensional substrate. In some embodiments, the substrate can be three-dimensional. Tens, hundreds, thousands, or millions of sections from a sample can be reflected by physical locations of containers on the substrate.

If the location of the first section in the sample is known, then that information can be associated with targets within the container containing the section. For example, as shown in FIG. 5, after the sections 510 of the solid tissue 505 have been placed in containers on the substrate 515, the targets of the sections can be stochastically labeled, amplified, and/or counted. The information (e.g., number of types of molecules) arising from container aa on the grid 515 can correspond 520 to physical section (e.g., location) 1 of the solid tissue 505. Similarly, the information arising from container ab of the substrate 515 can correspond 520 to physical section 4 of the solid tissue 505.

In some embodiments, the methods of the disclosure can be used for identifying the surface of a sample. For example, spatial labels can be added to the surface of sample (e.g., solid tissue). The sample can be lysed, stochastically labeled with the spatial labels, amplified, and/or digitally counted. Targets which were on the surface of the sample can be distinguished from targets on the interior of the sample, based on the spatial label. Identifying the surface of a sample, and/or distinguishing between the interior and exterior of a sample can be useful for determining boundaries of a solid tissue (e.g., tumor), determining if resection of a solid tissue was performed completely, and/or identifying boundaries of different physiological structure or cell types.

Spatial labels can be associated with a spatially intact sample. For example, a needle, or array of needles, can insert spatial labels into an intact sample. Spatial labels can be inserted into an intact sample in a variety of ways, including but not limited to, needle insertion, pin insertion, insertion through blood capillaries, injection, electroporation, transduction, and transformation. The intact sample can then be lysed for stochastic barcoding, amplification, and digital counting.

Stochastic Barcoding with Physical Separation of Samples Combined with Time Separation In some embodiments, stochastically barcoding the plurality of targets in the sample can include contacting the sample with a device. The device can be a needle, a needle array, a tube, a suction device, an injection device, an electroporation device, a fluorescent activated cell sorter device, a microfluidic device, or any combination thereof. The device can contact sections of the sample at a specified rate. The specified rate can correlate the spatial locations of the plurality of targets with the one or more time points.

Containers on a substrate can be filled in an order that reflects a physical location. Spatial labels can be combined with a section as a part of the sample collection. For example a sampling device comprising a suction device could be used to remove a sample in a predefined pattern. As the section of the sample travels through the suction device spatial labels can be associated with the section. The serial addition of the spatial labels can identify where the suction device was in space at the time of sectioning.

Figure 6:
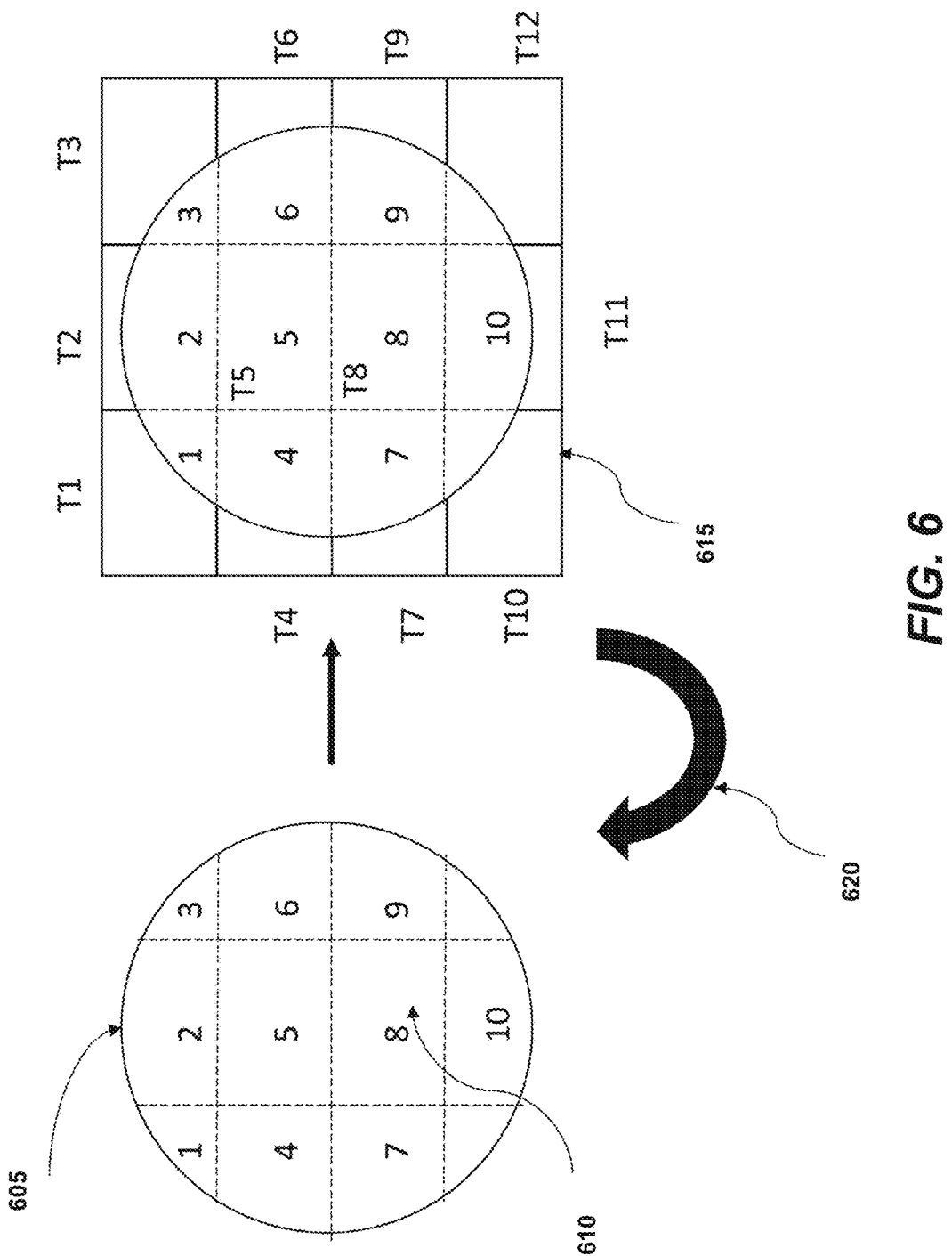
FIG. 6 illustrates a non-limiting exemplary embodiment for determining spatial locations of targets in a sample by time points.

For example, as shown in FIG. 6, a solid tissue 605 can be divided into sections 610 with a sampling device. The sections 610 can be transported to a substrate 615 based on the order in which they were obtained from the sample. For example, section 1 can be placed in a container in the substrate 615 which corresponds to time 1 (T1). The container which corresponds to T1 can comprise a time label (see below). The targets in the sections can be stochastically labeled, amplified, and/or counted. The information (e.g., number of types of molecules) arising from container T1 on the substrate 615 can correspond 620 to physical section (e.g., location) 1 of the solid tissue 605. Similarly, the information arising from container T4 of the substrate 615 can correspond 620 to physical section 4 of the solid tissue 605. The time label can indicate the physical location of the section in the sample by comparing the rate at which the sampling device processes each section from the sample to the substrate. Obtainment of the sections by the sampling device can be performed serially. The time labels can be added to sections and/or containers in serial before sections are added, simultaneously with addition of the section to the container, or after the section is added to the container.

For example, a needle array device can inject solid supports comprising stochastic barcodes with spatial labels into a solid tissue. As the needle retracts the solid support is left in the tissue. As the needle retracts further up a column of a solid tissue, a series of solid supports can be placed in the tissue (e.g., along a column). The rate of movement of the device can be correlated to a time that the device was in a specific position. In this way, the time a spatial label was associated with a target can be indicative of its position in the sample.

In another example, the sampling device can comprise a microfluidic chip. The sampling device can be capable of taking a section of a sample, and placing it in a microfluidic chip. Inside the microfluidic chip the section can be encapsulated in an emulsion (e.g., droplet). The emulsion can comprise a stochastic barcode with a spatial label. The emulsion can be placed in a container of a substrate. The location in the substrate in which the emulsion is placed can be indicative of the physical location of the section in the sample because of the information carried in the time label.

Non-Physical Representation of Containers

Figure 7:
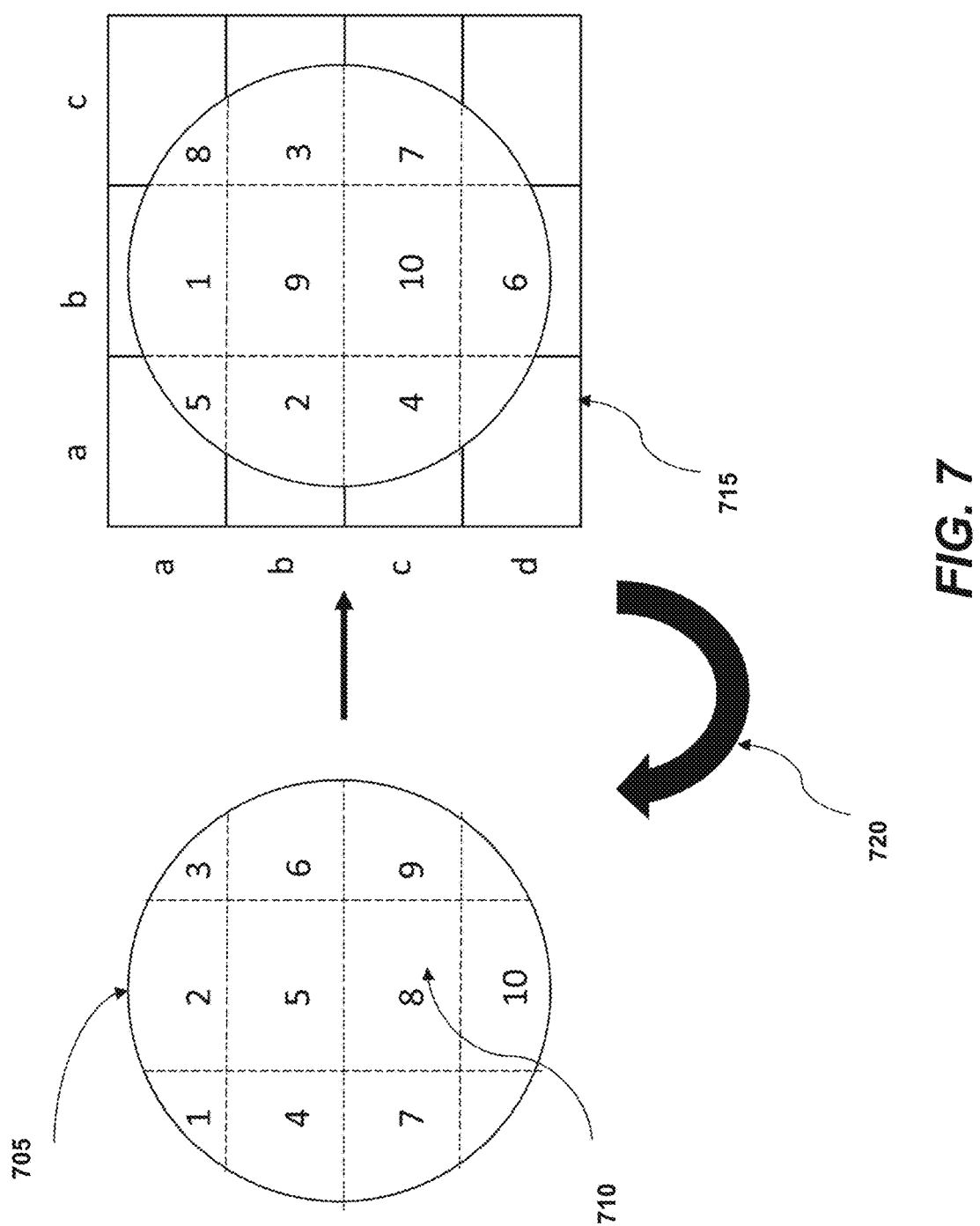
FIG. 7 illustrates a non-limiting exemplary embodiment for determining spatial locations of targets in a sample by randomizing the orientation of sections of the sample.

The disclosure provides for a method for estimating the number of molecules in a specific location of a sample. The method can comprise dividing the sample into sections and stochastically labeling the sections with a barcode such that they contain information about the physical location of the sections. The stochastic barcoding does not have to occur in containers that have a similar physical relationship to the sample, as described in FIGS. 5 and 6. The containers do not have a similar physical relationship to the sample. The method do not need to make use of containers. For example, as shown in FIG. 7, the sample 605 can be divided into sections 710. The sections 710 can be placed into one or more randomly located containers on a substrate 715, wherein the location of the section has no physical relationship to the physical structure, shape and/or morphology of the sample 705. The placement of sections of a solid tissue onto the substrate can be performed in two or three dimensions. FIG. 7 illustrates an exemplary embodiment of a two dimensional substrate. In some embodiments, the substrate can be three-dimensional. Tens, hundreds, thousands, or millions of sections from a sample can be reflected by physical locations of containers on the substrate.

If the location of the first section in the sample is known, then that information can be associated with targets within the container containing the section. For example, as shown in FIG. 7, after the sections 710 of the solid tissue 705 have been placed in containers on the substrate 715 the targets of the sections can be stochastically labeled, amplified, and/or counted. The information (e.g., number of types of molecules) arising from container aa on the grid 715 can correspond 720 to a physical section (e.g., location) of the solid tissue 605 (container aa corresponds to section 5, though it is located where section 1 of the sample is).

Addition of Stochastic Barcodes to Samples

Samples and/or sections of samples can be added to containers on a substrate in parallel. A sampling device can obtain spatially known samples in parallel and then be used associate the samples with a spatial label. For example an array of biopsies can be obtained. The biopsies can be associated with labels on the device which obtains the biopsies. The biopsies can be associated with labels after the biopsies are put into containers. In some embodiments a needle array is used to obtain samples.

The spatial labels can be combined with a sample as a part of the sample collection. For example a suction device could be used to remove a sample in a predefined pattern. As the sample travels through the suction device spatial labels can be associated with the sample. The serial addition of the label can identify where the suction device was in space at the time of collection.

For example a solid tumor can be resected. The resected tumor has its exterior labeled with spatial labels, for example by spraying the sample, immersing the sample, or contact the sample with a composition comprising a spatial label.

Spatial Barcoding of Specific Cells

In some embodiments, spatial labels are delivered to a specific target location. The target location can refer to a location in the body, a specific type of cell, and/or a subcellular compartment. A spatial label can be associated with a molecule known to target a specific organ in the body. For example, a spatial label can be associated with a molecule that is processed in the liver, a spatial label can be associated with a molecule that can cross the blood brain barrier, a spatial label can be associated with a molecule that can be taken up by blood capillaries. The molecule to which a spatial label is associated with can bring the spatial label in close proximity to a location in the body of interest. The location of the body of interest can be isolated, stochastically labeled with the spatial labeled, amplified, and/or digitally counted to obtain information about the number of targets in the location of interest.

A spatial label can be associated with a molecule known to target a specific cell. For example, a spatial label can be associated with a molecule that targets an immune cell (e.g., a targeting molecule). A spatial label can be associated with a molecule that targets a virus. A spatial label can be associated with a molecule that targets the blood brain barrier. The molecule can be a targeting molecule that can bring the spatial label to a location in a sample (e.g., subject).

A spatial label can be associated with a molecule known to target a specific subcellular compartment. For example, a spatial label can be associated with a vesicle which can comprise a location tag, such as for the endoplasmic reticulum. The vesicle can deliver the spatial label within close proximity of the endoplasmic reticulum. The endoplasmic reticulum can be isolated, stochastically labeled with the spatial label, amplified, and/or digitally counted.

Exemplary subcellular compartments can include, but are not limited to mitochondria, Golgi complex, cell wall, endoplasmic reticulum, nucleus, nucleolus, lysosomes, protein complexes (e.g., APC, lincRNAs), and the like. Exemplary targeting molecules can include but are not limited to nuclear localization sequences, nuclear export sequences, chloroplast localization signals, mitochondrial localization signals, and the like. In some embodiments, the targeting molecule can comprise a vesicle. Exemplary vesicles can include liposomes, microsomes, nanodots, quantum dots, nanoparticles, and viral capsids, or any combination thereof.

Method of Label Lithography

The methods of the disclosure can provide for building a spatial label after the label has been constricted within and/or contacted to a sample. In some embodiments, the methods include: stochastically barcoding the plurality of targets in the sample using a plurality of stochastic barcodes, wherein each of the plurality of stochastic barcodes comprises a pre-spatial label; concatenating one or more spatial label blocks onto the pre-spatial label to generate a spatial label; and identifying the spatial location of each of the plurality of targets using the spatial label.

Figure 8:
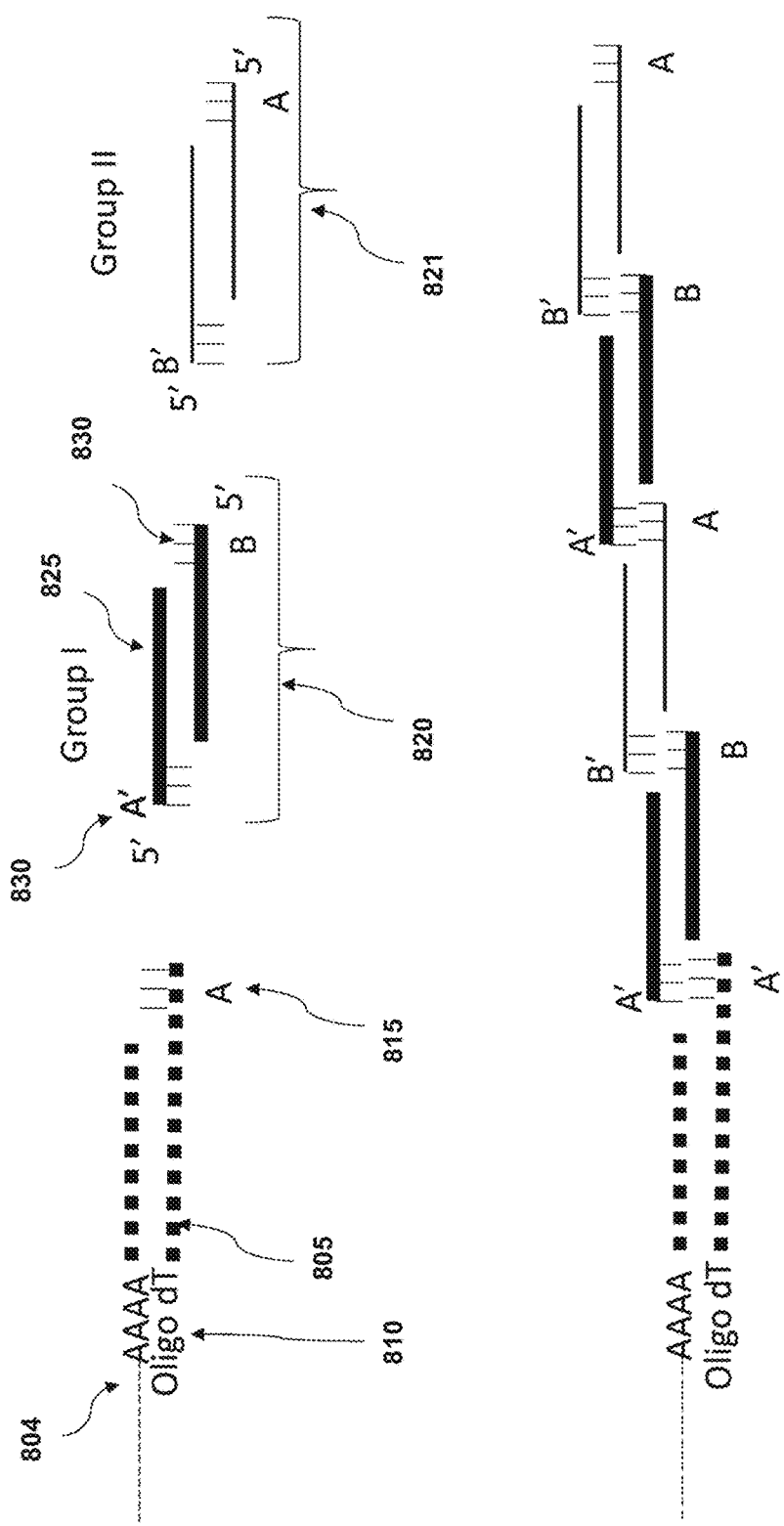
FIG. 8 shows a non-limiting exemplary schematic of label lithography.

FIG. 8 shows an exemplary embodiment of the label lithography method of the disclosure. A target 804 can associate with a pre-spatial label 805. A pre-spatial label 805 can comprise a nucleotide sequence that can hybridize with targets of interest (e.g., gene specific nucleotide sequence or oligo(dT)) 810. The pre-spatial label 805 can comprise an activatable consensus sequence 815. The activatable consensus sequence 815 can be a nucleotide sequence that can be linked to another nucleotide sequence or base. For example, an activatable sequence 815 can be a restriction site, a site for TA-ligation, and/or a photo-activatable nucleotide. The activatable consensus sequence 815 can be linked to a spatial label block 820/821. A spatial label block 820/821 can comprise a nucleotide sequence that is indicative of a spatial location 825. A spatial label block can comprise linking sequences 830. Linking sequences 830 can interact with the activatable consensus sequence 815 and/or other linking sequences in spatial label blocks 820. For example, a first group (Group I) of spatial label blocks 820/821 can comprise a first (A') and second (B) linking sequence. The first linking sequence (A') can interact with the activatable consensus sequence 815 in the pre-spatial label 705. A second group (Group II) of spatial label blocks 821 can comprise a first (B') and second (A) linking sequence. The first linking sequence (B') can interact with the second linking sequence (B) of the first group of spatial label blocks 821. In this way spatial label blocks 820/821 can be linked together.

Pre-Spatial Labels, Spatial Label Blocks, and Spatial Labels

A pre-spatial label can comprise a sequence that can associate with a target of interest. A pre-spatial label can associate with nucleic acid, including but not limited to, DNA, mRNA, RNA fragments, gene-specific regions, and regulatory elements (e.g., promoter, enhancer). A sequence that can bind to a target of interest can comprise a gene-specific region (e.g., a nucleotide sequence that is adapted to bind to a specific region of a gene), or a non-specific binding region (e.g., oligo(dT), random hexamer, random oligomer). A sequence that can associate with a target of interest can be at least 1, 2, 3, 4, 5, 6, 7, 8, 9, or 10 or more nucleotides in length. A sequence that can associate with a target of interest can be at least 1, 2, 3, 4, 5, 6, 7, 8, 9, or 10 or more nucleotides in length.

A pre-spatial label can comprise a molecular label, a cellular label, and/or a sample label. A pre-spatial label can comprise a sequence that can associate (e.g., hybridize) with a target. A pre-spatial label can be associated with a solid support. A pre-spatial label can be associated with a substrate.

A pre-spatial label can comprise an activatable consensus sequence. An activatable consensus sequence can comprise a sequence that can be activated to bind to a spatial label block. An activatable consensus sequence can be a cleavable sequence (e.g., restriction endonuclease cleavage site), a sequence that can be tagged, and/or a sequenced that can be ligated. An activatable consensus sequence can comprise a chemical moiety that can be activated. For example, the chemical moiety can comprise a fluorophore that can be excited, a photo-cleavable moiety, a moiety that responds to magnets, and a binding moiety (e.g., biotin/streptavidin).

An activatable consensus sequence can comprise at least 1, 2, 3, 4, 5, 6, 7, 8, 9, or 10 or more nucleotides. An activatable consensus sequence can comprise at most 1, 2, 3, 4, 5, 6, 7, 8, 9, or 10 or more nucleotides.

A pre-spatial label can comprise a sequence that can associate with a target of interest, a molecular label, a sample label and/or an activatable consensus sequence. In some embodiments, a pre-spatial label comprises a sequence that can associate with a target of interest, a molecular label, a sample label and/or an activatable consensus sequence.

A pre-spatial label can be at least 1, 2, 3, 4, 5, 6, 7, 8, 9, 10, 11, 12, 13, 14, 15 16, 17, 18, 19, 20, 21, 222, 23, 24, 25, 26, 27, 28, 29, 30, 31, 32, 33, 34, 35, 36, 37, 38, 39, 40, 41, 42, 43, 44, 45, 46, 47, 48, 49, or 50 or more nucleotides in length. A pre-spatial label can be at most 1, 2, 3, 4, 5, 6, 7, 8, 9, 10, 11, 12, 13, 14, 15 16, 17, 18, 19, 20, 21, 222, 23, 24, 25, 26, 27, 28, 29, 30, 31, 32, 33, 34, 35, 36, 37, 38, 39, 40, 41, 42, 43, 44, 45, 46, 47, 48, 49, or 50 or more nucleotides in length.

A spatial label block can comprise a sequence of nucleotides. The sequence can comprise at least 1, 2, 3, 4, 5, 6, 7, 8, 9, or 10 or more nucleotides. The sequence can comprise at most 1, 2, 3, 4, 5, 6, 7, 8, 9, or 10 or more nucleotides. A spatial label block can be linked to another (e.g., previous) spatial label block. Spatial label blocks can be linked together, for example, by chemistry (e.g., click chemistry), ligation, split-pool synthesis, combinatorial chemistry, and/or photoactivatable chemistry.

For example, a first group of spatial label blocks can comprise two sticky end sequences, wherein the sense strand has a first sticky end sequence, and the antisense strand has a second sticky end sequence on the 5' ends of each strand. A second group of spatial label blocks can comprise two sticky end sequences, wherein the sense strand has the second complementary sticky end sequence and the antisense strand has the first complementary sticky end sequence. The first group can be ligated to the second group. Only one ligation can occur. Subsequently, the first group can be contacted to the growing spatial label. The first group can ligate to the sticky end of the second group. Only one ligation can occur. In this way, a spatial label can be able to be lithographically produced on sample.

Linking of spatial label blocks can be performed before, during, and/or after contacting the pre-spatial label with a target of interest. Pre-spatial labels can be associated with targets before, during and/or after linking with spatial label blocks using chemical means such as cross-linking, hybridization to aid the association between the pre-spatial label and the target. This can reduce dissociation and/or diffusion of the pre-spatial labels away from the targets.

Linking of spatial label blocks can be performed in a geometric manner such that the resulting length of the spatial label corresponds to the geometric manner in which the spatial label blocks were linked. FIG. 9 shows an exemplary embodiment of a geometric manner of linking spatial label blocks. For example, as one moves left to right on a sample, spatial label blocks can be increasingly added to the pre-spatial label, thereby generating spatial labels with different lengths. The length of the spatial label can correspond to a physical location in the sample. A sample 905 can be divided into sections 910. The sections can be contacted with a pre-spatial label. The pre-spatial label can be contacted with an integer number of spatial label blocks. For example, the sections in row a are contacted with one spatial label block. The sections in row b are contacted with two spatial label blocks. The sections in row c are contacted with three spatial label blocks. The sections in row d are contacted with four spatial label blocks. Moving right to left, sections in column A can be contacted with one spatial label block, sections in column B can be contacted with two spatial label blocks. Sections in column C can be contacted with three spatial label blocks. The number of spatial label blocks in each section can be a representation of its location in a first dimension (y, vertical) and a second dimension (x horizontal) space within the sample.

The sections can be contacted with the spatial label blocks in any order. The sections can be contacted by rows only. The sections can be contacted by columns only. The sections can be contacted first by rows and then by columns. The sections can be contacted first by columns and then by rows.

The sections can be stochastically labeled, amplified, and/or digitally counted. The length of the spatial label can provide information about the x and y location of the section in the sample. In the embodiment shown in FIG. 7, the shortest spatial label corresponds to the top left-most corner and the longest spatial label corresponds to the bottom right-most corner.

Methods for Determining Spatial Location of Targets

Disclosed herein are methods for identifying distinct cells in two or more samples. In some embodiments, the methods include: stochastically barcoding a plurality of targets in the two or more samples using a plurality of stochastic barcodes, wherein each of the plurality of stochastic barcodes comprises a spatial label and a molecular label; estimating the number of the plurality of targets in the two or more samples using the molecular label; and distinguishing the two or more samples from each other using the spatial label, wherein the plurality of targets associated with stochastic barcodes with different spatial labels are from different samples.

Stochastically barcoding the plurality of targets in the two or more samples can include hybridizing the plurality of stochastic barcodes with the plurality of targets to generate stochastically barcoded targets, and at least one of the plurality of targets can be hybridized to one of the plurality of stochastic barcodes. Stochastically barcoding the plurality of targets in the two or more samples can include generating an indexed library of the stochastically barcoded targets.

Each of the two or more samples can include a plurality of cells and the plurality of targets are associated with the plurality of cells. Stochastically barcoding the plurality of targets in the two or more samples can be performed with a solid support comprising a plurality of synthetic particles associated with the plurality of stochastic barcodes.

Identification of Specific Cells in a Population of Cells

Spatial labels can be used to identify and label distinct samples (e.g., cells) in a mixed population of samples (e.g., cells). The samples can be, for example, cells in a mixed population of cells.

Figure 10:
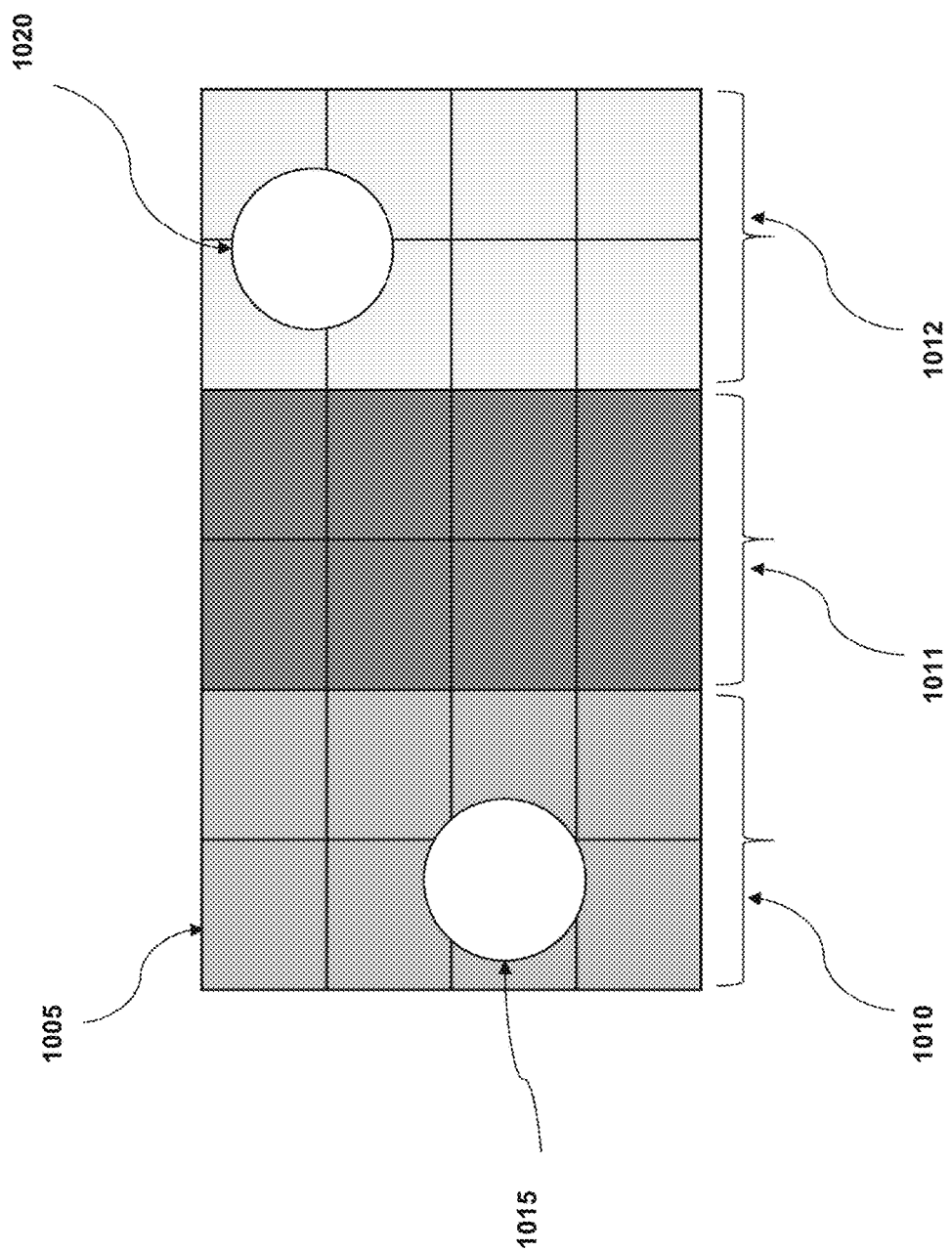
FIG. 10 shows a non-limiting exemplary embodiment for distinguishing targets of a sample for a plurality of samples.

FIG. 10 illustrates an exemplary embodiment of the method of identifying distinct cells with a spatial label. A sample, for example, comprising a mixed population of cells 1015/1020 can be contacted to a substrate 10905, wherein the substrate 1005 comprises a distribution of different groups of spatial labels 1010/1011/1012. Targets from an individual cell 1015 can be physically close to a first group of same spatial labels 1010. Targets from a different individual cell 1020 can be physically more distant from the first group of spatial labels 1010, but can be close in physical space to other spatial labels 1012 (e.g., a second group of spatial labels). The cells can be lysed, stochastically labeled, amplified, and/or digitally counted. The spatial label can then be used as a code to distinguish between targets from different individual cells.

The targets can be associated with the closest spatial labels. Spatial labels can be any spatial labels of the disclosure (e.g., pre-spatial labels, spatial labels). The targets can be associated with spatial labels that are at least 1, 2, 3, 4, 5, 6, 7, 8, 9, 10, 15, 20, 25, 30, 35, 40, 45, or 50 more micrometers from the outer edge of the sample (e.g., cell). The targets can be associated with spatial labels that are at most 1, 2, 3, 4, 5, 6, 7, 8, 9, 10, 15, 20, 25, 30, 35, 40, 45, or 50 more micrometers from the outer edge of the sample (e.g., cell).

Identification of Spatial Location of Targets in a Sample

Figure 11:
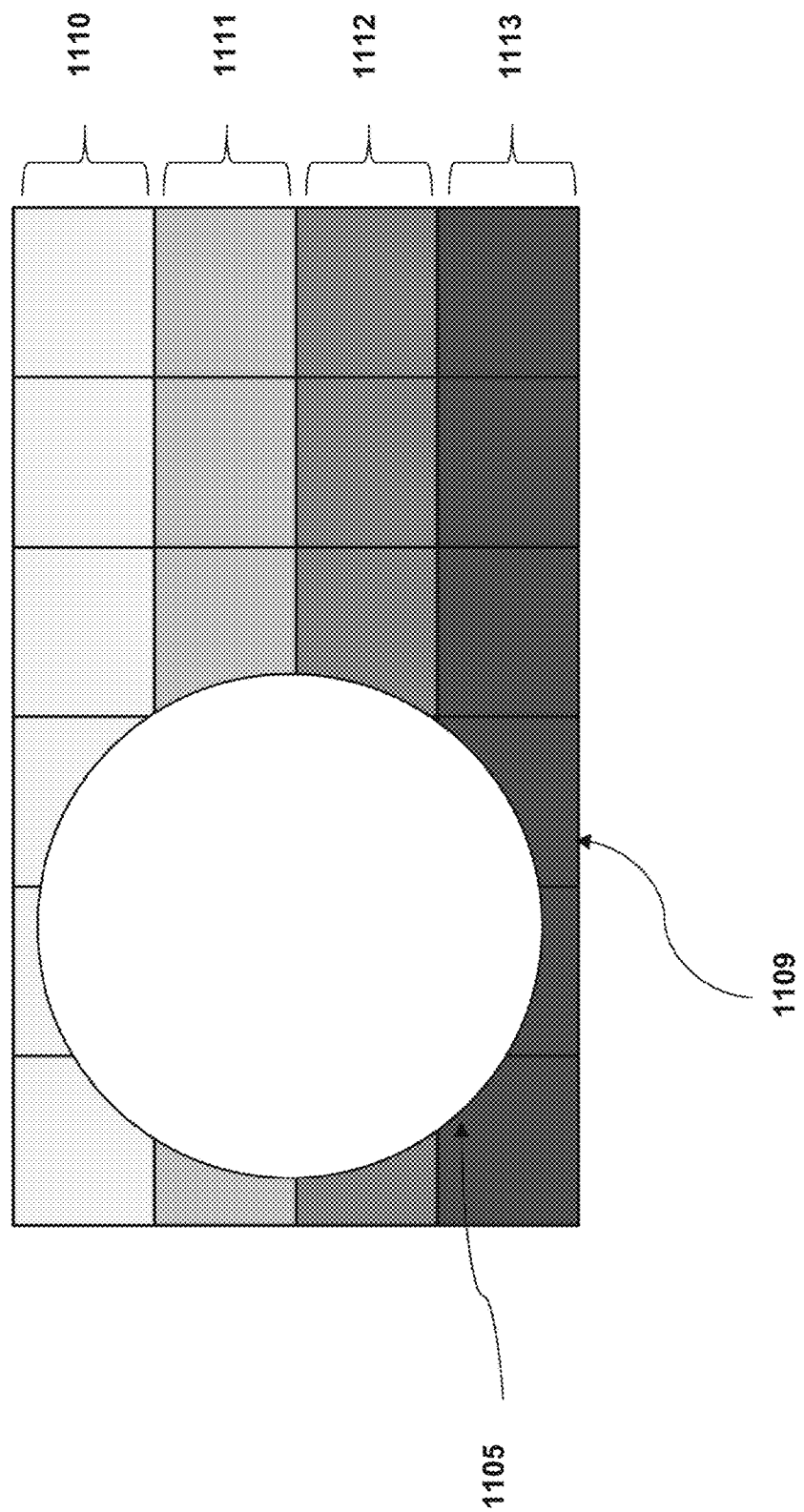
FIG. 11 shows a non-limiting exemplary embodiment for distinguishing subcellular localization of targets in a cell.

The disclosure provides for methods for determining the subcellular location of targets in a cell. FIG. 11 illustrates how subcellular information can be obtained using spatial labels. A sample (e.g., a cell) 1105 can be contacted to a substrate 1009 comprising one or more groups of spatial labels 1110/1111/1112/1113. The groups of spatial labels 1110/1111/1112/1113 can be distributed over the surface of a substrate. The groups of spatial labels 1110/1111/1112/1113 can be distributed over containers (e.g., microwells) of the substrate. The groups of spatial labels 1110/1111/1112/1113 can be distributed into the sample 1105. The groups of spatial labels 1110/1111/1112/1113 can be arranged such that the sample (e.g., a cell) 1105 contacts multiple distinct groups of spatial labels 1110/1111/1112/1113. The sample 1005 can be crosslinked, physically separated, lysed, stochastically labeled with the distinct groups of spatial labels 1110/1111/1112/1113, amplified, and/or digitally counted.

Because the location of the distinct groups of spatial labels 1110/1111/1112/1113 can be known, the location of the targets in the cell can be correlated to the identification of the spatial labels 1110/1111/1112/1113. In this way, spatial labels can be used to identify the spatial location of targets in a sample.

Methods for Optical Barcoding and Optical Barcoding

Disclosed herein are methods for determining spatial locations of a plurality of singles cells. In some embodiments, the methods include: stochastically barcoding the plurality of singe cells using a plurality of synthetic particles, wherein each of the plurality of synthetic particles comprises a plurality of stochastic barcodes, a first group of optical labels, and a second group of optical labels, wherein each of the plurality of stochastic barcodes comprises a cellular label and a molecular label, wherein each optical label in the first group of optical labels comprises a first optical moiety and each optical label in the second group of optical labels comprises a second optical moiety, and wherein each of the plurality of synthetic particles is associated with an optical barcode comprising the first optical moiety and the second optical moiety; detecting the optical barcode of each of the plurality of synthetic particles to determine the location of each of the plurality of synthetic particles; and determining the spatial locations of the plurality of single cells based on the locations of the plurality of synthetic particles.

Synthetic Particles with Stochastic Barcodes and Optical Barcodes

Disclosed herein are synthetic particles (for examples beads and magnetic beads) associated with (e.g., attached with) stochastic barcodes and optical labels. For example, a synthetic particle can have one or more optical label regions in which the optical labels are associated with the synthetic particle. In some embodiments, each synthetic particle can have, or have about, 1, 2, 3, 4, 5, 6, 7, 8, 9, 10, 11, 12, 13, 14, 15, 16, 17, 18, 19, 20, 30, 40, 50, 60, 70, 80, 90, 100, 1000, 2000, 3000, 4000, 5000, 6000, 7000, 8000, 9000, 10000, or a number or a range between any two of these values, optical label regions. The size of the optical label region can vary, for example, an optical label region can be, or be about, a few microns to tens of microns in width, length, or diameter. In some embodiments, the width, length, or diameter of the optical label region can be, or be about, 1, 2, 3, 4, 5, 6, 7, 8, 9, 10, 11, 12, 13, 14, 15, 16, 17, 18, 19, 20, 30, 40, 50, 60, 70, 80, 90, 100, 1000, 2000, 3000, 4000, 5000, 6000, 7000, 8000, 9000, 10000 microns, or a number or a range between any two of these values. In some embodiments, the length of the optical label region can be, or be about, 1, 2, 3, 4, 5, 6, 7, 8, 9, 10, 11, 12, 13, 14, 15, 16, 17, 18, 19, 20, 30, 40, 50, 60, 70, 80, 90, 100, 1000, 2000, 3000, 4000, 5000, 6000, 7000, 8000, 9000, 10000 microns, or a number or a range between any two of these values. For a synthetic particle with more than one optical label regions, each of the optical label regions can have the same size or different sizes. For example, at least 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, of the optical label regions can have different sizes. For example, at least 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, of the optical label regions can have the same size.

The arrangement of the optical label regions can vary. Non-limiting examples of the arrangement of the optical label regions include a longitudinal format, a vertical format, a grid manner, a circular format, or any combination thereof. The shape of the optical label regions can also vary. For example, the optical label regions can be oval-, rectangle-, triangle-, diamond-shaped, or any combination thereof. The optical label regions can be grouped together or be separated from one another. For example, two optical label regions can be separated from one another by, or by about, 1, 2, 3, 4, 5, 6, 7, 8, 9, 10, 11, 12, 13, 14, 15, 16, 17, 18, 19, 20, 30, 40, 50, 60, 70, 80, 90, 100, 1000, 2000, 3000, 4000, 5000, 6000, 7000, 8000, 9000, 10000 microns, or a number or a range between any two of these values.

The optical label regions can occupy substantially the entire synthetic particle surface, or part of the synthetic particle surface. In some embodiments, the optical label regions can occupy, or occupy about, 0.00001%, 0.0001%, 0.01%, 0.1%, 1%, 2%, 3%, 4%, 5%, 6%, 7%, 8%, 9%, 10%, 20%, 30%, 40%, 50%, 60%, 70%, 80%, 90%, 99.9%, or a number or a range between any two of these values, of the synthetic particle surface. Optical label regions can include optical labels. In some embodiments, an optical label region can have an optical label (OL) attached to the surface of the synthetic particle. The number of optical labels in each of the optical label region can vary, for example, be or be about, 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000. In some embodiments, an optical label comprises a probe sequence.

In some embodiments, each synthetic particle can include 9 types of optical labels, OL1-9, attached to the surface of the synthetic particle. In some embodiments, each synthetic particle can include 1, 2, 3, 4, 5, 6, 7, 8, 9, 10, 11, 12, 13, 14, 15, 16, 17, 18, 19, 20, 30, 40, 50, 60, 70, 80, 90, 100, 1000, 2000, 3000, 4000, 5000, 6000, 7000, 8000, 9000, 10000, or a number or a range between any two of these numbers, types of optical labels. For each synthetic particle, OL1-9 can be the same or different. In some embodiments, each type of optical labels is attached to the synthetic particle in one optical label region. In some embodiments, at least one of the optical label regions on the synthetic particle comprises more than one type of optical labels. In some embodiments, two, three, four, five, or more types of optical labels are present in one optical label region.

An optical label can comprise an oligonucleotide sequence. The optical label can comprise an oligonucleotide. In some embodiments, the optical label can comprise two or more oligonucleotides with the same sequence. The optical label can be, or be about, 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, nucleotides in length. The oligonucleotides of optical labels can be, or be about, 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, nucleotides in length.

In some embodiments, OL1-3 can be used to encode cellular label part 1 corresponding to a first 96 unique cellular labels in the first encoding step; OS4-6 can be used to encode cellular label part 2 corresponding to a second 96 unique cellular labels in the second split step; and OL7-9 can be used to encode cellular label part 3 corresponding to a third 96 unique cellular labels in the third split step. In some embodiments, OLs encode 1, 2, 3, 4, 5, 6, 7, 8, 9, 10, 20, 30, 40, 50, 60, 70, 80, 90, 100, or a number between any two of these values cellular label parts. In some embodiments, 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number between any two of these values, optical labels can be used to encode a part of a cellular label. In some embodiments, each part of a cellular label can represent 1, 2, 3, 4, 5, 6, 7, 8, 9, 10, 20, 30, 40, 50, 60, 70, 80, 90, 100, 1000, 10000, 100000, 1000000, 10000000, 10000000, 100000000, 1000000000, or a number or a range between any two of these values, unique cellular labels. An optical barcode of a synthetic particle can include the optical labels on the synthetic particle. The optical barcode of a synthetic particle can include 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number between any two of these values, optical labels.

In some embodiments, an optical label can comprise an optical moiety, for example a fluorophore or a chromophore. In some embodiments, each nucleotide of an optical label can be associated with an optical moiety, for example a fluorophore or a chromophore, on the 3' end. The optical moiety can be selected from a group of spectrally-distinct optical moieties. Spectrally-distinct optical moieties include optical moieties with distinguishable emission spectra even if their emission spectral may overlap.

Non-limiting examples of optical moieties include Xanthene derivatives: fluorescein, rhodamine, Oregon green, eosin, and Texas red; Cyanine derivatives: cyanine, indocarbocyanine, oxacarbocyanine, thiacarbocyanine, and merocyanine; Squaraine derivatives and ring-substituted squaraines, including Seta, SeTau, and Square dyes; Naphthalene derivatives (dansyl and prodan derivatives); Coumarin derivatives; oxadiazole derivatives: pyridyloxazole, nitrobenzoxadiazole and benzoxadiazole; Anthracene derivatives: anthraquinones, including DRAQ5, DRAQ7 and CyTRAK Orange; Pyrene derivatives: cascade blue; Oxazine derivatives: Nile red, Nile blue, cresyl violet, oxazine 170; Acridine derivatives: proflavin, acridine orange, acridine yellow; Arylmethine derivatives: auramine, crystal violet, malachite green; and Tetrapyrrole derivatives: porphin, phthalocyanine, bilirubin. Other non-limiting examples of optical moieties include Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Hoechst 33342, DAPI, Hoechst 33258, SYTOX Blue, Chromomycin A3, Mithramycin, YOYO-1, Ethidium Bromide, Acridine Orange, SYTOX Green, TOTO-1, TO-PRO-1, TO-PRO: Cyanine Monomer, Thiazole Orange, CyTRAK Orange, Propidium Iodide (PI), LDS 751, 7-AAD, SYTOX Orange, TOTO-3, TO-PRO-3, DRAQ5, DRAQ7, Indo-1, Fluo-3, Fluo-4, DCFH, DHR, and SNARF.

The excitation wavelength of the optical moieties can vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, or a number or a range between any two of these values. The emission wavelength of the optical moieties can also vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, or a number or a range between any two of these values.

The molecular weights of the optical moieties can vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 Daltons (Da), or a number or a range between any two of these values. The molecular weights of the optical moieties can also vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 kilo Daltons (kDa), or a number or a range between any two of these values.

The group of spectrally distinct optical moieties can, for example, include five different fluorophores, five different chromophores, a combination of five fluorophores and chromophores, a combination of four different fluorophores and a non-fluorophore, a combination of four chromophores and a non-chromophore, or a combination of four fluorophores and chromophores and a non-fluorophore non-chromophore. In some embodiments, the optical moieties can be one of 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, of spectrally-distinct moieties.

In some embodiments, each of a plurality of synthetic particles has a unique optical barcode. For example, the plurality of synthetic particles can include, include about, or include more than 1, 2, 3, 4, 5, 6, 7, 8, 9, 10, 100, 200, 300, 400, 500, 600, 700, 800, 900, $10^3$, $10^4$, $10^5$, $10^6$, $10^7$, $10^8$, $10^9$, $10^{10}$, $10^{11}$, $10^{12}$, or a number or a range between any two of these values, synthetic particles each with a unique optical barcode. Some of a plurality of synthetic particles can have the same optical barcode. The plurality of synthetic particles can include, include about, or include more than 1, 2, 3, 4, 5, 6, 7, 8, 9, 10, 100, 200, 300, 400, 500, 600, 700, 800, 900, $10^3$, $10^4$, $10^5$, $10^6$, $10^7$, $10^8$, $10^9$, $10^{10}$, $10^{11}$, $10^{12}$, or a number or a range between any two of these values, synthetic particles some of which with the same optical barcodes.

In addition to the "optical labels," substantially entire synthetic particle surface or some part of the synthetic particle surface can be attached with stochastic barcodes. For example, the stochastic barcodes can occupy 0.00001%, 0.0001%, 0.01%, 0.1%, 1%, 2%, 3%, 4%, 5%, 6%, 7%, 8%, 9%, 10%, 20%, 30%, 40%, 50%, 60%, 70%, 80%, 90%, 99.9%, or a number or a range between any two of these values, of the synthetic particle surface. The stochastic barcodes can be, or be about, 1, 2, 3, 4, 5, 6, 7, 8, 9, 10, 20, 30, 40, 50, 60, 70, 80, 90, 100, 1000, or a number or a range between any two of these values, nucleotides in length.

Methods for Loading Spatial Labels on a Substrate

Spatial labels can be pre-located on a substrate. A surface of substrate can be pre-imprinted with stochastic barcodes. In other words, the coordinates of each stochastic barcode on the surface of the substrate can be known. Stochastic barcodes can be pre-imprinted in any geometric manner. In some embodiments, a solid support comprising stochastic barcodes can be pre-located on a substrate. In some embodiments, the coordinates of the stochastic barcodes on a substrate can be unknown. The location of the stochastic barcodes can be user-generated. When the location of the stochastic barcodes on a substrate is unknown, the location of the stochastic barcodes can be decoded.

Methods for Encoding Solid Supports

Disclosed herein are methods for creating encoded solid supports, such as encoded synthetic particles, for determining spatial locations of a plurality of singles cells. Each synthetic particle can contain 9 "anchor regions." In some embodiments, each synthetic particle can contain, or contain about, 1, 2, 3, 4, 5, 6, 7, 8, 9, 10, 11, 12, 13, 14, 15, 16, 17, 18, 19, 20, 30, 40, 50, 60, 70, 80, 90, 100, 1000, 2000, 3000, 4000, 5000, 6000, 7000, 8000, 9000, 10000, or a number or a range between any two of these values, anchor regions. Each anchor region can have a size of about a few microns to tens of microns wide. In some embodiments, each anchor region can have a size of 1, 2, 3, 4, 5, 6, 7, 8, 9, 10, 11, 12, 13, 14, 15, 16, 17, 18, 19, 20, 30, 40, 50, 60, 70, 80, 90, 100, 1000, 2000, 3000, 4000, 5000, 6000, 7000, 8000, 9000, 10000, or a number or a range between any two of these values, microns in size.

The arrangement of the anchor regions can vary. Non-limiting examples of the arrangement of the anchor regions include a longitudinal format, a vertical format, a grid manner, a circular format, or any combination thereof. The shape of the anchor regions can also vary. For example, the anchor regions can be oval-, rectangle-, triangle-, diamond-shaped, or any combination thereof, in shape. The anchor regions can be grouped together or be separated from one another. For example, two anchor regions can be separated from one another by, or by about, 1, 2, 3, 4, 5, 6, 7, 8, 9, 10, 11, 12, 13, 14, 15, 16, 17, 18, 19, 20, 30, 40, 50, 60, 70, 80, 90, 100, 1000, 2000, 3000, 4000, 5000, 6000, 7000, 8000, 9000, 10000 microns, or a number or a range between any two of these values.

The anchor regions can occupy substantially the entire synthetic particle surface, or part of the synthetic particle surface In some embodiments, the anchor regions can occupy, or occupy about, 0.00001%, 0.0001%, 0.01%, 0.1%, 1%, 2%, 3%, 4%, 5%, 6%, 7%, 8%, 9%, 10%, 20%, 30%, 40%, 50%, 60%, 70%, 80%, 90%, 99.9%, or a number or a range between any two of these values, of the synthetic particle surface. Anchor regions can include optical labels. In some embodiments, an anchor region can have an optical label (OL) attached to the surface of the synthetic particle. The number of optical labels in each of the anchor region can vary, for example, be or be about, 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000. In some embodiments, an optical label comprises a probe sequence. Anchor regions with optical labels attached can be referred to as optical label regions.

Each anchor region can have a unique optical label (OL) attached to the surface of the synthetic particle. In some embodiments, each synthetic particle can include 9 types of optical labels, OL1-9, attached to the surface of the synthetic particle. In some embodiments, each synthetic particle can include 1, 2, 3, 4, 5, 6, 7, 8, 9, 10, 11, 12, 13, 14, 15, 16, 17, 18, 19, 20, 30, 40, 50, 60, 70, 80, 90, 100, 1000, 2000, 3000, 4000, 5000, 6000, 7000, 8000, 9000, 10000, or a number or a range between any two of these numbers, types of optical labels. For each synthetic particle, OL1-9 can be the same or different. In some embodiments, each type of optical labels is attached to the synthetic particle in one anchor region. In some embodiments, at least one of the anchor regions on the synthetic particle comprises more than one type of optical labels. In some embodiments, two, three, four, five, or more types of optical labels are present in one anchor region.

An optical label can comprise an oligonucleotide sequence. The optical label can comprise an oligonucleotide. In some embodiments, the optical label can comprise two or more oligonucleotides with the same sequence. The optical label can be, or can be about, 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, nucleotides in length. The oligonucleotides of optical labels can be, or can be about, 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, nucleotides in length.

In some embodiments, OL1-3 can be used to encode cellular label part 1 corresponding to a first 96 unique cellular labels in the first encoding step; OS4-6 can be used to encode cellular label part 2 corresponding to a second 96 unique cellular labels in the second split step; and OL7-9 can be used to encode cellular label part 3 corresponding to a third 96 unique cellular labels in the third split step. In some embodiments, 1, 2, 3, 4, 5, 6, 7, 8, 9, 10, 20, 30, 40, 50, 60, 70, 80, 90, 100, or a number between any two of these values, optical labels can be used to encode a part of a cellular label. In some embodiments, each part of a cellular label correspond to 1, 2, 3, 4, 5, 6, 7, 8, 9, 10, 20, 30, 40, 50, 60, 70, 80, 90, 100, 1000, 10000, 100000, 1000000, 10000000, 10000000, 100000000, 1000000000, or a number or a range between any two of these values, unique cellular labels. An optical barcode of a synthetic particle can include the optical labels on the synthetic particle. The optical barcode of a synthetic particle can include 1, 2, 3, 4, 5, 6, 7, 8, 9, 10, 20, 30, 40, 50, 60, 70, 80, 90, 100, 1000, or a number between any two of these values, optical labels.

In addition to the "optical label" constituting the optical barcode, the entire synthetic particle surface or part of the synthetic particle surface can be attached with the universal sequence (US) with 3' up, i.e. 3' end of the oligonucleotide is not attached to the synthetic particle. In some embodiments, the OL oligonucleotides can be 5' up and not 3' ends up. If the OL oligonucleotides are 5' up, the optical moieties can be added by ligation method. The universal sequence can occupy 0.00001%, 0.0001%, 0.01%, 0.1%, 1%, 2%, 3%, 4%, 5%, 6%, 7%, 8%, 9%, 10%, 20%, 30%, 40%, 50%, 60%, 70%, 80%, 90%, 99.9%, or a number or a range between any two of these values, of the synthetic particle surface. The universal sequence can be, or can be about, 1, 2, 3, 4, 5, 6, 7, 8, 9, 10, 20, 30, 40, 50, 60, 70, 80, 90, 100, 1000, or a number or a range between any two of these values, nucleotides in length.

For cellular labels each comprising three parts, encoding the synthetic particles can include three encoding steps. The cellular label can include part 1 of the cellular label, part 2 of the cellular label, and part 3 of the cellular label. In some embodiments, the cellular label can include 1, 2, 3, 4, 5, 6, 7, 8, 9, 10, 20, 30, 40, 50, 60, 70, 80, 90, 100, 1000, or a number or a range between any two of these values, parts. Encoding the synthetic particles can include 1, 2, 3, 4, 5, 6, 7, 8, 9, 10, 20, 30, 40, 50, 60, 70, 80, 90, 100, 1000, or a number or a range between any two of these values, encoding steps.

At the first encoding step/the first split step, synthetic particles can be distributed across 96 wells of a first plate and hybridize to oligonucleotides in each well. In some embodiments, the first plate can include 96, 394, 1000, 2000, 3000, 4000, 5000, 6000, 7000, 8000, 9000, 10000, or a number between any two of these values, wells. Each well can contain 4 types of oligonucleotides, possibly including the universal sequence (US) and three additional types of oligonucleotides. Each additional type of oligonucleotides can include an optical label with an optical moiety, for example a fluorophore or a chromophore, on the 3' end. The three additional types of oligonucleotides encode a cellular label part. In some embodiments, each well can contain, or contain about, 1, 2, 3, 4, 5, 6, 7, 8, 9, 10, 11, 12, 13, 14, 15, 16, 17, 18, 19, 20, 30, 40, 50, 60 70, 80, 90, 100, 1000, or a number of range between any two of these values, additional types of oligonucleotides. Each type of oligonucleotides can be, or can be about, 1, 2, 3, 4, 5, 6, 7, 8, 9, 10, 20, 30, 40, 50, 60, 70, 80, 90, 100, 1000, 10000, or a number or a range between any two of these values, nucleotides in length. Each cellular part can be, or can be about, 1, 2, 3, 4, 5, 6, 7, 8, 9, 10, 20, 30, 40, 50, 60, 70, 80, 90, 100, 1000, or a number or a range between any two of these values, nucleotides in length.

The first type of oligonucleotides each can contain a region complementary to the universal sequence (US), followed by part 1 of the cellular label (1 of 96), followed by a linker sequence (linker 1). The region complementary to the universal sequence can be, or can be about, 1, 2, 3, 4, 5, 6, 7, 8, 9, 10, 20, 30, 40, 50, 60, 70, 80, 90, 100, or a number or a range between any two of these values, nucleotides in length. Linker 1 can be, or can be about, 1, 2, 3, 4, 5, 6, 7, 8, 9, 10, 20, 30, 40, 50, 60, 70, 80, 90, 100, 1000, 10000, or a number or a range between any two of these values, nucleotides in length.

The second type of oligonucleotides each can include a duplex structure that contains a strand complementary to OL1 with a small 5' extension, and a shorter strand complementary to the extension on the longer strand. The shorter strand can include an optical label with an optical moiety, for example a fluorophore or a chromophore, on the 3' end. In some embodiments, the optical label is on the 5's end, or neither 5's end nor 3's end. The optical label can be, or can be about, 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, nucleotides in length. The optical moiety can be selected from a group of spectrally-distinct optical moieties. Spectrally-distinct optical moieties include optical moieties with distinguishable emission spectra even if their emission spectral may overlap.

The third type of oligonucleotides each can include a duplex structure that contains a strand complementary to OL2 with a small 5' extension, and a shorter strand complementary to the extension on the longer strand. The shorter strand can include an optical label with an optical moiety, for example a fluorophore or a chromophore, on the 3' end. In some embodiments, the optical label is on the 5's end, or neither 5's end nor 3's end. The optical moiety can be selected from a group of spectrally-distinct optical moieties.

The fourth type of oligonucleotides each can include a duplex structure that contains a strand complementary to OL3 with a small 5' extension, and a shorter strand complementary to the extension on the longer strand. The shorter strand can include an optical label with an optical moiety, for example a fluorophore or a chromophore, on the 3' end. In some embodiments, the optical label is on the 5's end, or neither 5's end nor 3's end. The optical moiety can be selected from a group of spectrally-distinct optical moieties.

After the synthetic particles are distributed across 96 wells of the first plate and hybridize to oligonucleotides in each well, a polymerase such as a DNA polymerase and a ligase such as a DNA ligase can be introduced into each well. DNA polymerase can extend the universal sequence with cellular label part 1 and linker 1 sequences. DNA ligase can covalently attach the optical moieties onto the OL oligonucleotides.

At the second encoding step including pool and second split, synthetic particles from all the wells of the first plate can be pooled, and split into each of the 96 wells of a second plate. In some embodiments, the second plate can include 96, 394, 1000, 2000, 3000, 4000, 5000, 6000, 7000, 8000, 9000, 10000, or a number between any two of these values, wells. Each well can contain 4 types of oligonucleotides, possibly including the universal sequence (US) and three additional types of oligonucleotides. Each additional type of oligonucleotides can include an optical label with an optical moiety, for example a fluorophore or a chromophore, on the 3' end. The three additional types of oligonucleotides encode a cellular label part. In some embodiments, each well can contain, or contain about, 1, 2, 3, 4, 5, 6, 7, 8, 9, 10, 11, 12, 13, 14, 15, 16, 17, 18, 19, 20, 30, 40, 50, 60 70, 80, 90, 100, 1000, or a number of range between any two of these values, additional types of oligonucleotides. Each type of oligonucleotides can be, or can be about, 1, 2, 3, 4, 5, 6, 7, 8, 9, 10, 20, 30, 40, 50, 60, 70, 80, 90, 100, 1000, 10000, or a number or a range between any two of these values, nucleotides in length. Each cellular part can be, or can be about, 1, 2, 3, 4, 5, 6, 7, 8, 9, 10, 20, 30, 40, 50, 60, 70, 80, 90, 100, 1000, or a number or a range between any two of these values, nucleotides in length.

The first type of oligonucleotide each can include linker 1, followed by part 2 of the cellular label (1 of 96, for example), followed by another linker sequence (linker 2). Linker 2 can be, or can be about, 1, 2, 3, 4, 5, 6, 7, 8, 9, 10, 20, 30, 40, 50, 60, 70, 80, 90, 100, 1000, 10000, or a number or a range between any two of these values, nucleotides in length.

The second type of oligonucleotides each can include a duplex structure that contains a strand complementary to OL4 with a small 5' extension, and a shorter strand complementary to the extension on the longer strand. The shorter strand can include an optical label with an optical moiety, for example a fluorophore or a chromophore, on the 3' end. In some embodiments, the optical label is on the 5's end, or neither 5's end nor 3's end. The optical label can be, or can be about, 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, nucleotides in length. The optical moiety can be selected from a group of spectrally-distinct optical moieties. Spectrally-distinct optical moieties include optical moieties with distinguishable emission spectra even if the emission spectral may overlap.

The third type of oligonucleotides each can include a duplex structure that contains a strand complementary to OL5 with a small 5' extension, and a shorter strand complementary to the extension on the longer strand. The shorter strand can include an optical label with an optical moiety, for example a fluorophore or a chromophore, on the 3' end. In some embodiments, the optical label is on the 5's end, or neither 5's end nor 3's end. The optical moiety can be selected from a group of spectrally-distinct optical moieties.

The fourth type of oligonucleotides each can include a duplex structure that contains a strand complementary to OL6 with a small 5' extension, and a shorter strand complementary to the extension on the longer strand. The shorter strand can include an optical label with an optical moiety, for example a fluorophore or a chromophore, on the 3' end. In some embodiments, the optical label is on the 5's end, or neither 5's end nor 3's end. The optical moiety can be selected from a group of spectrally-distinct optical moieties.

After the synthetic particles are distributed across 96 wells of the second plate and hybridize to oligonucleotides in each well, a polymerase such as a DNA polymerase and a ligase such as a DNA ligase can be introduced into each well. DNA polymerase can extend the universal sequence with cellular label part 2 and linker 2 sequences. DNA ligase can covalently attach the optical moieties onto the OL oligonucleotides.

At the third encoding step including pool and third split, synthetic particles from all the wells of the second plate can be pooled, and split into each of the 96 wells of a third plate. In some embodiments, the third plate can include 96, 394, 1000, 2000, 3000, 4000, 5000, 6000, 7000, 8000, 9000, 10000, or a number between any two of these values, wells. Each well can contain 4 types of oligonucleotides, possibly including the universal sequence (US) and three additional types of oligonucleotides. Each additional type of oligonucleotides can include an optical label with an optical moiety, for example a fluorophore or a chromophore, on the 3' end. The three additional types of oligonucleotides encode a cellular label part. In some embodiments, each well can contain, or contain about, 1, 2, 3, 4, 5, 6, 7, 8, 9, 10, 11, 12, 13, 14, 15, 16, 17, 18, 19, 20, 30, 40, 50, 60 70, 80, 90, 100, 1000, or a number of range between any two of these values, additional types of oligonucleotides. Each type of oligonucleotides can be, or can be about, 1, 2, 3, 4, 5, 6, 7, 8, 9, 10, 20, 30, 40, 50, 60, 70, 80, 90, 100, 1000, 10000, or a number or a range between any two of these values, nucleotides in length. Each cellular part can be, or can be about, 1, 2, 3, 4, 5, 6, 7, 8, 9, 10, 20, 30, 40, 50, 60, 70, 80, 90, 100, 1000, or a number or a range between any two of these values, nucleotides in length.

The first type of oligonucleotide each can include linker 2, followed by part 3 of the cellular label (1 of 96), followed by molecular index (randomers) and oligo(dA). The molecular index can be, or can be about, 1, 2, 3, 4, 5, 6, 7, 8, 9, 10, 20, 30, 40, 50, 60, 70, 80, 90, 100, 1000, 10000, or a number or a range between any two of these values, nucleotides in length. The oligo(dA) can be, or can be about, 1, 2, 3, 4, 5, 6, 7, 8, 9, 10, 20, 30, 40, 50, 60, 70, 80, 90, 100, 1000, 10000, or a number or a range between any two of these values, nucleotides in length.

The second type of oligonucleotides each can include a duplex structure that contains a strand complementary to OL7 with a small 5' extension, and a shorter strand complementary to the extension on the longer strand. The shorter strand can include an optical label with an optical moiety, for example a fluorophore or a chromophore, on the 3' end. In some embodiments, the optical label is on the 5's end, or neither 5's end nor 3's end. The optical label can be, or can be about, 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, nucleotides in length. The optical moiety can be selected from a group of spectrally-distinct optical moieties. Spectrally-distinct optical moieties include optical moieties with distinguishable emission spectra even if the emission spectral may overlap.

The third type of oligonucleotides each can include a duplex structure that contains a strand complementary to OL8 with a small 7' extension, and a shorter strand complementary to the extension on the longer strand. The shorter strand can include an optical label with an optical moiety, for example a fluorophore or a chromophore, on the 3' end. In some embodiments, the optical label is on the 5's end, or neither 5's end nor 3's end. The optical moiety can be selected from a group of spectrally-distinct optical moieties.

The fourth type of oligonucleotides each can include a duplex structure that contains a strand complementary to OL9 with a small 5' extension, and a shorter strand complementary to the extension on the longer strand. The shorter strand can include an optical label with an optical moiety, for example a fluorophore or a chromophore, on the 3' end. In some embodiments, the optical label is on the 5's end, or neither 5's end nor 3's end. The optical moiety can be selected from a group of spectrally-distinct optical moieties.

After the synthetic particles are distributed across 96 wells of the third plate and hybridize to oligonucleotides in each well, a polymerase such as a DNA polymerase and a ligase such as a DNA ligase can be introduced into each well. DNA polymerase can extend the universal sequence with cellular label part 3 sequence. DNA ligase can covalently attach the optical moiety onto the OL oligonucleotides.

At the $i^{th}$ encoding step including pool and second split, synthetic particles from all the wells of the $(i-1)^{th}$ plate can be pooled, and split into each of the 96 wells of a $i^{th}$ plate. In some embodiments, the $i^{th}$ plate can include 96, 394, 1000, 2000, 3000, 4000, 5000, 6000, 7000, 8000, 9000, 10000, or a number between any two of these values, wells. Each well can contain m types of oligonucleotides, possibly including the universal sequence (US) and j additional types of oligonucleotides. Each additional type of oligonucleotides can include an optical label with an optical moiety, for example a fluorophore or a chromophore, on the 3' end. The optical moiety can be part of an oligonucleotide. The j additional types of oligonucleotides encode a cellular label part. In some embodiments, each well can contain, or contain about, 1, 2, 3, 4, 5, 6, 7, 8, 9, 10, 11, 12, 13, 14, 15, 16, 17, 18, 19, 20, 30, 40, 50, 60 70, 80, 90, 100, 1000, or a number of range between any two of these values, additional types of oligonucleotides. Each type of oligonucleotides can be, or can be about, 1, 2, 3, 4, 5, 6, 7, 8, 9, 10, 20, 30, 40, 50, 60, 70, 80, 90, 100, 1000, 10000, or a number or a range between any two of these values, nucleotides in length. Each cellular part can be, or can be about, 1, 2, 3, 4, 5, 6, 7, 8, 9, 10, 20, 30, 40, 50, 60, 70, 80, 90, 100, 1000, or a number or a range between any two of these values, nucleotides in length.

The first type of oligonucleotide each can include linker (i−1), followed by part i of the cellular label (1 of 96, for example), followed by another linker sequence (linker i). Linker i and linker (i−1) can be, or can be about, 1, 2, 3, 4, 5, 6, 7, 8, 9, 10, 20, 30, 40, 50, 60, 70, 80, 90, 100, 1000, 10000, or a number or a range between any two of these values, nucleotides in length.

Each of the j additional types of oligonucleotides can include a duplex structure that contains a strand complementary to OLm with a small 5' extension, and a shorter strand complementary to the extension on the longer strand. The shorter strand can include an optical label with an optical moiety, for example a fluorophore or a chromophore, on the 3' end. In some embodiments, the optical label is on the 5's end, or neither 5's end nor 3's end. The optical label can be, or can be about, 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, nucleotides in length. The optical moiety can be selected from a group of k spectrally-distinct optical moieties. Spectrally-distinct optical moieties include optical moieties with distinguishable emission spectra even if the emission spectral may overlap.

After the synthetic particles are distributed across 96 wells of the $i^{th}$ plate and hybridize to oligonucleotides in each well, a polymerase such as a DNA polymerase and a ligase such as a DNA ligase can be introduced into each well. DNA polymerase can extend the universal sequence with cellular label part i and linker i sequences. DNA ligase can covalently attach the optical moieties onto the OL oligonucleotides. In some embodiments, optical moieties can be added to each of the OL oligonucleotides by polymerase extension with optical moieties labeled nucleotides. For an optical barcode comprising n optical labels, possibly encoded by i encoding steps each with j additional types of oligonucleotides, each selected from a group of k spectrally-distinct optical moieties, the optical barcode can represent $k^n = k^{i*j}$ unique cellular labels.

In some embodiments, the first encoding reaction with coupling of OS1-3 and 1 of the 96 cell label part 1 can be achieved by an enzymatic process. In some embodiments, the first encoding reaction can be incorporated in the lithography process. Instead of generating 1 type of core synthetic particle with lithography, 96 types of synthetic particles can be generated by lithography. The universal sequence can be replaced by one of the 96 'cell label part 1' oligonucleotides. The corresponding combination of OS1, OS2, and OS3 optical moieties can be attached to the synthetic particles during the lithography process.

Synthetic Particle Synthesis

In some embodiments, the synthetic particles are generated using photolithography. In some embodiments, the synthetic particles are generated using stop flow lithography. To generate synthetic particles with n OL oligonucleotides, for example 9 OL oligonucleotides, fabricate a microfluidic device (e.g. PDMS or NOA) with n input ports converging to a single channel, leading to 1 output port. In each of the input port, feed in a mixture of, for example, Poly(ethylene glycol) diacrylate PEGDA, photoinitiator, 5' acrydite modified universal sequence (US) oligonucleotide, and 5' acrydite modified OL oligonucleotide (OL1 oligonucleotide for input port 1, OL2 oligonucleotide for input port 2, . . . , OLn oligonucleotide for input port n). Subsequently, apply pressure at each of the input ports. The n inputs will form n parallel streams under laminar flow regime. Expose a region of the converged channel with, for example, UV through a photomask with the outline of the shape of the synthetic particle. Upon UV exposure, PEGDA and acrydite oligonucleotides can crosslink to form a solid hydrogel synthetic particle, with n regions each with a different OL oligonucleotide arranged side by side. The synthetic particles can be collected at the output port and used for the encoding solid supports such for synthetic particles.

Methods for Decoding Substrates

In some embodiments, the methods can include decoding the solid support. In some embodiments, the method can include decoding the plurality of synthetic particles. Decoding the plurality of synthetic particles can include detecting the optical barcode of the plurality of synthetic particles. The methods can include determining the locations of the plurality of synthetic particles. Detecting the optical barcode of each of the plurality of synthetic particles to determine the location of each of the plurality of synthetic particles can include generating an optical image showing the optical barcodes and the locations of the plurality of synthetic particles.

The disclosure provides for methods for decoding substrates (e.g., arrays) comprising stochastic barcodes. In some embodiments, the methods comprise decoding the solid support. In some embodiments, decoding does not rely solely on the use of optical signatures, for example optical barcodes (although as described herein, the use of beads with optical signatures can allow the "reuse" of the decoding probes), but rather on the use of combinatorial decoding nucleic acids that are added during a decoding step. Decoding can be performed with sequential hybridizations. The decoding nucleic acids can hybridize either to a distinct identifier coding nucleic acid (identifier probe) that is placed on the beads, or to the bioactive agent itself, for example when the bioactive agent is a nucleic acid, at least some portion of which is single stranded to allow hybridization to a decoding probe. The decoding nucleic acids can be either directly or indirectly labeled. Decoding occurs by detecting the presence of the label.

The coding nucleic acids (also termed identifier probes (IP) or identifier nucleic acids) can comprise a primer sequence and an adjacent decoding sequence. Each decoder (or decoding) probe can comprise a priming sequence (sometimes referred to herein as an "invariant sequence"), that can hybridize to the primer sequence, and at least one decoding nucleotide, generally contained within a variable sequence. The decoder probes can be made as sets, with each set comprising at least four subsets that each have a different decoding nucleotide at the same position i.e. the detection position, (i.e. adenine, thymidine (or uracil, as desired), cytosine and guanine), with each nucleotide at the detection position (detection nucleotide) comprising a unique label, preferably a fluorophore. The decoder probes can be added under conditions that allow discrimination of perfect complementarity and imperfect complementarity. Thus, the decoding probe that comprises the correct base for basepairing with the coding nucleotide being interrogated can hybridize the best. The other decoding probes can be washed away. The detection of the unique fluorophore associated with the detection nucleotide can allow for the identification of the coding nucleotide at that position. By repeating these steps with a new set of decoding probes that extends the position of the detection nucleotide by one base, the identity of next coding nucleotide can be elucidated. Decoding can use a large number of probes. Split and mix combinatorial synthesis can be used to prepare the decoding probes.

Parity analysis can be used during decoding to increase the robustness and accuracy of the system. Parity analysis can refer to a decoding step wherein the signal of a particular element can be analyzed across a plurality of decoding stages. That is, following at least one decoding step, the signal of an array element across the decoding stages can be analyzed. The signal from a particular bead can be evaluated across multiple stages. Although the analysis can include any parameter that can be obtained from the signals, such as evaluating the total signal obtained across the stages, the parity of the signals across the stages can be analyzed.

Parity can refer to the digital or modular readout of signals, i.e. odd or even, when binary signals are used. The digit sum of the signals across a plurality of stages can be translated into a parity determination. The parity determination can be useful in evaluating the decoding process. For example, codes can be designed to have an odd number of a particular signal, for example a red signal, when viewed across all stages or decoding steps, or a pre-determined plurality of stages or decoding steps. The detection of an even number of red stages can provide an indication that an error has occurred at some point in decoding. When this result is obtained, the faulty code can either be discarded, or the analysis repeated.

The disclosure provides for introducing a "redundant stage" into the decoding system. A redundant stage can refer to a stage that serves as a parity check. That is, following the decoding stages, an additional stage can be included to analyze the parity. This analysis can provide an indication of the competence or validity of the decoding. When codes are designed with a pre-determined parity, the redundant stage can be used to detect the parity of the signals obtained from the decoding step. The redundant stage can detect errors in parity because if there has been an error in decoding, the parity detected following the redundant stage will be different from the parity designed into the codes.

In some embodiments, decoding can occur through the use of 8-mer oligonucleotides strung together to create a decoding oligonucleotide with a few 8-mers on it. The decoding oligonucleotide can comprise at least 1, 2, 3, 4, 5, 6, 7, 8, 9, or 10 or more 8-mers on it. The decoding oligonucleotide can comprise at most 1, 2, 3, 4, 5, 6, 7, 8, 9, or 10 or more 8-mers on it. The decoding oligonucleotide can hybridize to a few different stochastic barcodes (e.g., by hybridizing its different 8-mer regions to different 8-mer regions on stochastic barcodes). The decoding oligonucleotide can be fluorescently labeled, melted off, and sequenced. The decoding oligonucleotides can be fluorescently labeled in different colors. The decoding oligonucleotides can be fluorescently labeled with the same color but with various levels of fluorescent intensity, thereby generating a "gray-scale" map of a probe. Repeating this can provide a solvable map of where each 8-mer of a stochastic barcode is in relation to each other. The method can be repeated at least 1, 2, 3, 4, 5, 6, 7, 8, 9, or 10 or more times. The method can be repeated at most 1, 2, 3, 4, 5, 6, 7, 8, 9, or 10 or more times.

In some embodiments, decoding can be performed by sequencing by synthesis (e.g., using 454 and/or ion torrent sequencing). Decoding can be performed by imaging of optically encoded beads. For example, beads can be encoded with quantum dots or fluorophores which can be embedded in the beads. The quantum dots or fluorophores can be used in the decoding process. In some embodiments, the optically encoded beads can comprise a dye. The dye can be used to distinguish beads with different stochastic barcodes. Decoding can occur with the use of physically encoded solid supports (e.g., beads). For example, a bead can be patterned or engraved with an identifier. The identifier can be etched into the bead with a laser or with lithography methods. In some embodiments, the beads can be physically encoded based on size and/or shape. Decoding can occur with electronically encoded beads. Decoding can use an electronic readout to read the electronic identifier in the beads. An electronic identifier can include, for example, an RFID tag, an electrical resistance, and/or an electrical capacitance.

Diffusion Across a Substrate

When a sample (e.g., cell) is stochastically barcoded according to the methods of the disclosure, the cell can be lysed. In some embodiments, lysis of a cell can result in the diffusion of the contents of the lysis (e.g., cell contents) away from the initial location of lysis. In other words, the lysis contents can move into a larger surface area than the surface area taken up by the cell.

Diffusion of sample lysis mixture (e.g., comprising targets) can be modulated by various parameters including, but not limited to, viscosity of the lysis mixture, temperature of the lysis mixture, the size of the targets, the size of physical barriers in a substrate, the concentration of the lysis mixture, and the like. For example, the temperature of the lysis reaction can be performed at a temperature of at least 1, 2, 3, 4, 5, 10, 15, 20, 25, 30, 35, or 40 C or more. The temperature of the lysis reaction can be performed at a temperature of at most 1, 2, 3, 4, 5, 10, 15, 20, 25, 30, 35, or 40 C or more. The viscosity of the lysis mixture can be altered by, for example, adding thickening reagents (e.g., glycerol, beads) to slow the rate of diffusion. The viscosity of the lysis mixture can be altered by, for example, adding thinning reagents (e.g., water) to increase the rate of diffusion. A substrate can comprise physical barriers (e.g., wells, microwells, microhills) that can alter the rate of diffusion of targets from a sample. The concentration of the lysis mixture can be altered to increase or decrease the rate of diffusion of targets from a sample. The concentration of a lysis mixture can be increased or decreased by at least 1, 2, 3, 4, 5, 6, 7, 8, or 9 or more fold. The concentration of a lysis mixture can be increased or decreased by at most 1, 2, 3, 4, 5, 6, 7, 8, or 9 or more fold.

The rate of diffusion can be increased. The rate of diffusion can be decreased. The rate of diffusion of a lysis mixture can be increased or decreased by at least 1, 2, 3, 4, 5, 6, 7, 8, 9, or 10 or more fold compared to an un-altered lysis mixture. The rate of diffusion of a lysis mixture can be increased or decreased by at most 1, 2, 3, 4, 5, 6, 7, 8, 9, or 10 or more fold compared to an un-altered lysis mixture. The rate of diffusion of a lysis mixture can be increased or decreased by at least 10, 20, 30, 40, 50, 60, 70, 80, 90 or 100% compared to an un-altered lysis mixture. The rate of diffusion of a lysis mixture can be increased or decreased by at least 10, 20, 30, 40, 50, 60, 70, 80, 90 or 100% compared to an un-altered lysis mixture.

Sample Imaging

Figure 12:
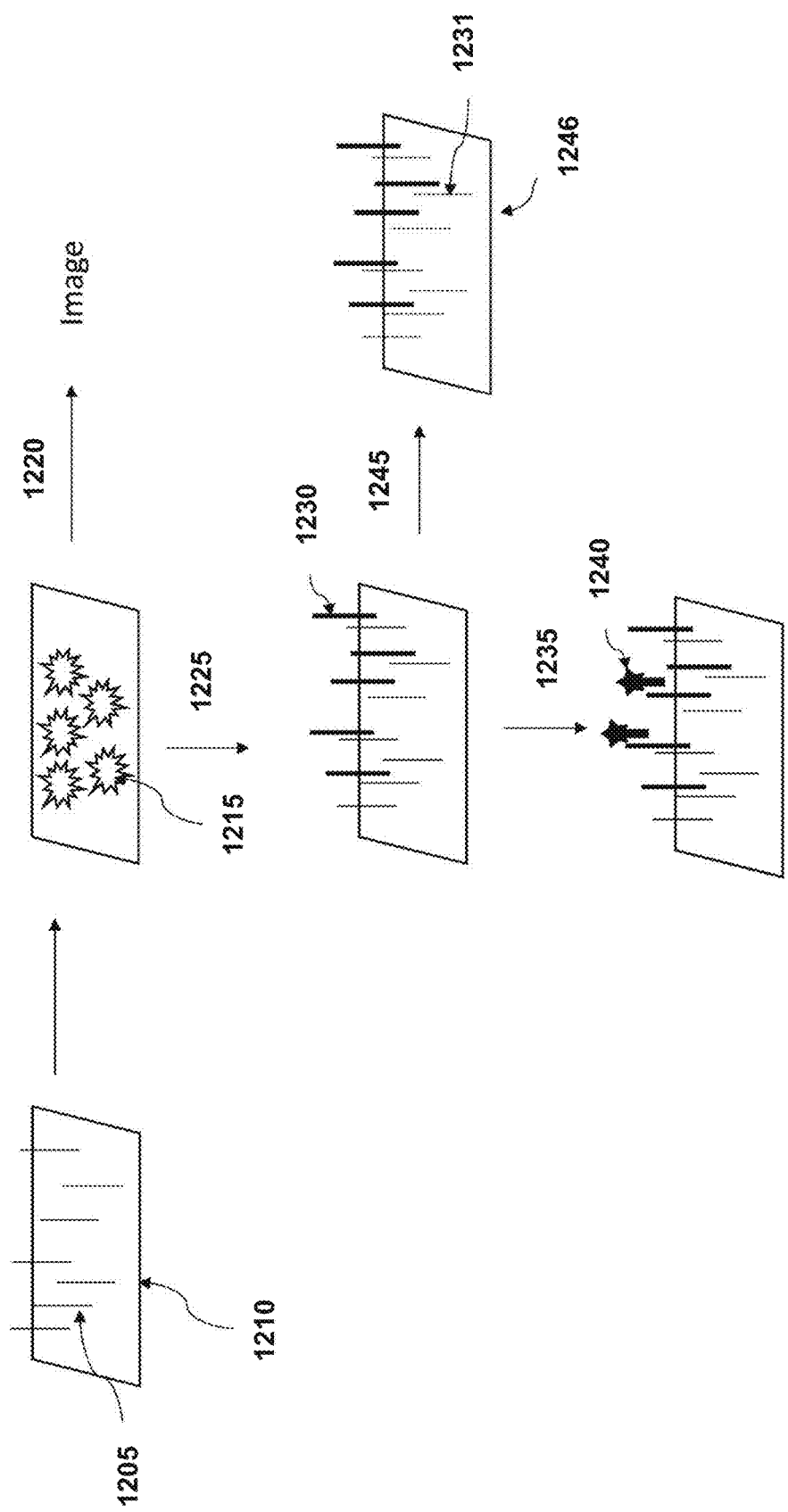
FIG. 12 illustrates a non-limiting exemplary embodiment for homopolymer tailing.

The disclosure provides for compositions, methods, kits, and systems for identifying the spatial location of nucleic acids in a target from a sample. FIG. 12 illustrates an exemplary embodiment of the homopolymer tailing method of the disclosure The disclosure provides for a substrate 1210 comprising a plurality of probes 1205 attached to the surface of the substrate. The substrate 1210 can be a microarray. The plurality of probes 1205 can comprise an oligo(dT). The plurality of probes 1205 can comprise a gene-specific sequence. The plurality of probes 105 can comprise a stochastic barcode. A sample (e.g., cells) 1215 can be placed and/or grown on the substrate 1210. The substrate comprising the sample can be analyzed 1220, for example by imaging and/or immunohistochemistry. The sample 1215 can be lysed 1225 on the substrate 1210. The nucleic acids 1230 from the sample 1215 can associate (e.g., hybridize) with the plurality of probes 1205 on the substrate 1210. In some embodiments, the nucleic acids 1230 can be reverse transcribed, homopolymer tailed, and/or amplified (e.g., with bridge amplification). The amplified nucleic acids can be interrogated 1235 with detection probes 1240 (e.g., fluorescent probes). The detection probes 1240 can be gene-specific probes. The location of binding of the detection probes 1240 on the substrate 1210 can be correlated with the image of the substrate, thereby producing a map that indicates the spatial location of nucleic acids in the sample.

In some embodiments, the methods of the disclosure can comprise making 1245 a replicate 1246 of the original substrate 1210. The replicate substrate 1246 can comprise a plurality of probes 1231. The plurality of probes 1231 can be the same as the plurality of probes 1205 on the original substrate 1210. The plurality of probes 1231 can be different than the plurality of probes 1205 on the original substrate 1210. For example, the plurality of probes 1205 can be oligo(dT) probes and the plurality of probes 1231 on the replicate substrate 1246 can be gene-specific probes. The replicate substrate can be processed like the original substrate, such as with interrogation by detection (e.g., fluorescent) probes.

Data Analysis and Display Software

Data Analysis and Visualization of Spatial Resolution of Targets

The disclosure provides for methods for estimating the number and position of targets with stochastic barcoding and digital counting using spatial labels. The data obtained from the methods of the disclosure can be visualized on a map. A map of the number and location of targets from a sample can be constructed using information generated using the methods described herein. The map can be used to locate a physical location of a target. The map can be used to identify the location of multiple targets. The multiple targets can be the same species of target, or the multiple targets can be multiple different targets. For example a map of a brain can be constructed to show the digital count and location of multiple targets.

The map can be generated from data from a single sample. The map can be constructed using data from multiple samples, thereby generating a combined map. The map can be constructed with data from tens, hundreds, and/or thousands of samples. A map constructed from multiple samples can show a distribution of digital counts of targets associated with regions common to the multiple samples. For example, replicated assays can be displayed on the same map. At least 1, 2, 3, 4, 5, 6, 7, 8, 9, or 10 or more replicates can be displayed (e.g., overlaid) on the same map. At most 1, 2, 3, 4, 5, 6, 7, 8, 9, or 10 or more replicates can be displayed (e.g., overlaid) on the same map. The spatial distribution and number of targets can be represented by a variety of statistics.

Combining data from multiple samples can increase the locational resolution of the combined map. The orientation of multiple samples can be registered by common landmarks, wherein the individual locational measurements across samples are at least in part non-contiguous. A particular example is sectioning a sample using a microtome on one axis and then sectioning a second sample along a different access. The combined dataset will give three dimensional spatial locations associated with digital counts of targets. Multiplexing the above approach will allow for high resolution three dimensional maps of digital counting statistics.

In some embodiments of the instrument system, the system will comprise computer-readable media that includes code for providing data analysis for the sequence datasets generated by performing single cell, stochastic barcoding assays. Examples of data analysis functionality that can be provided by the data analysis software include, but are not limited to, (i) algorithms for decoding/demultiplexing of the sample label, cellular label, spatial label, and molecular label, and target sequence data provided by sequencing the stochastic barcode library created in running the assay, (ii) algorithms for determining the number of reads per gene per cell, and the number of unique transcript molecules per gene per cell, based on the data, and creating summary tables, (iii) statistical analysis of the sequence data, e.g. for clustering of cells by gene expression data, or for predicting confidence intervals for determinations of the number of transcript molecules per gene per cell, etc., (iv) algorithms for identifying sub-populations of rare cells, for example, using principal component analysis, hierarchical clustering, k-mean clustering, self-organizing maps, neural networks etc., (v) sequence alignment capabilities for alignment of gene sequence data with known reference sequences and detection of mutation, polymorphic markers and splice variants, and (vi) automated clustering of molecular labels to compensate for amplification or sequencing errors. In some embodiments, commercially-available software can be used to perform all or a portion of the data analysis, for example, the Seven Bridges (https://www.sbgenomics.com/) software can be used to compile tables of the number of copies of one or more genes occurring in each cell for the entire collection of cells. In some embodiments, the data analysis software can include options for outputting the sequencing results in useful graphical formats, e.g. heatmaps that indicate the number of copies of one or more genes occurring in each cell of a collection of cells. In some embodiments, the data analysis software can further comprise algorithms for extracting biological meaning from the sequencing results, for example, by correlating the number of copies of one or more genes occurring in each cell of a collection of cells with a type of cell, a type of rare cell, or a cell derived from a subject having a specific disease or condition. In some embodiment, the data analysis software can further comprise algorithms for comparing populations of cells across different biological samples.

In some embodiments all of the data analysis functionality can be packaged within a single software package. In some embodiments, the complete set of data analysis capabilities can comprise a suite of software packages. In some embodiments, the data analysis software can be a standalone package that is made available to users independently of the assay instrument system. In some embodiments, the software can be web-based, and can allow users to share data.

In some embodiments all of the data analysis functionality can be packaged within a single software package. In some embodiments, the complete set of data analysis capabilities can comprise a suite of software packages. In some embodiments, the data analysis software can be a standalone package that is made available to users independently of the assay instrument system. In some embodiments, the software can be web-based, and can allow users to share data.

System Processors and Networks

Figure 13:
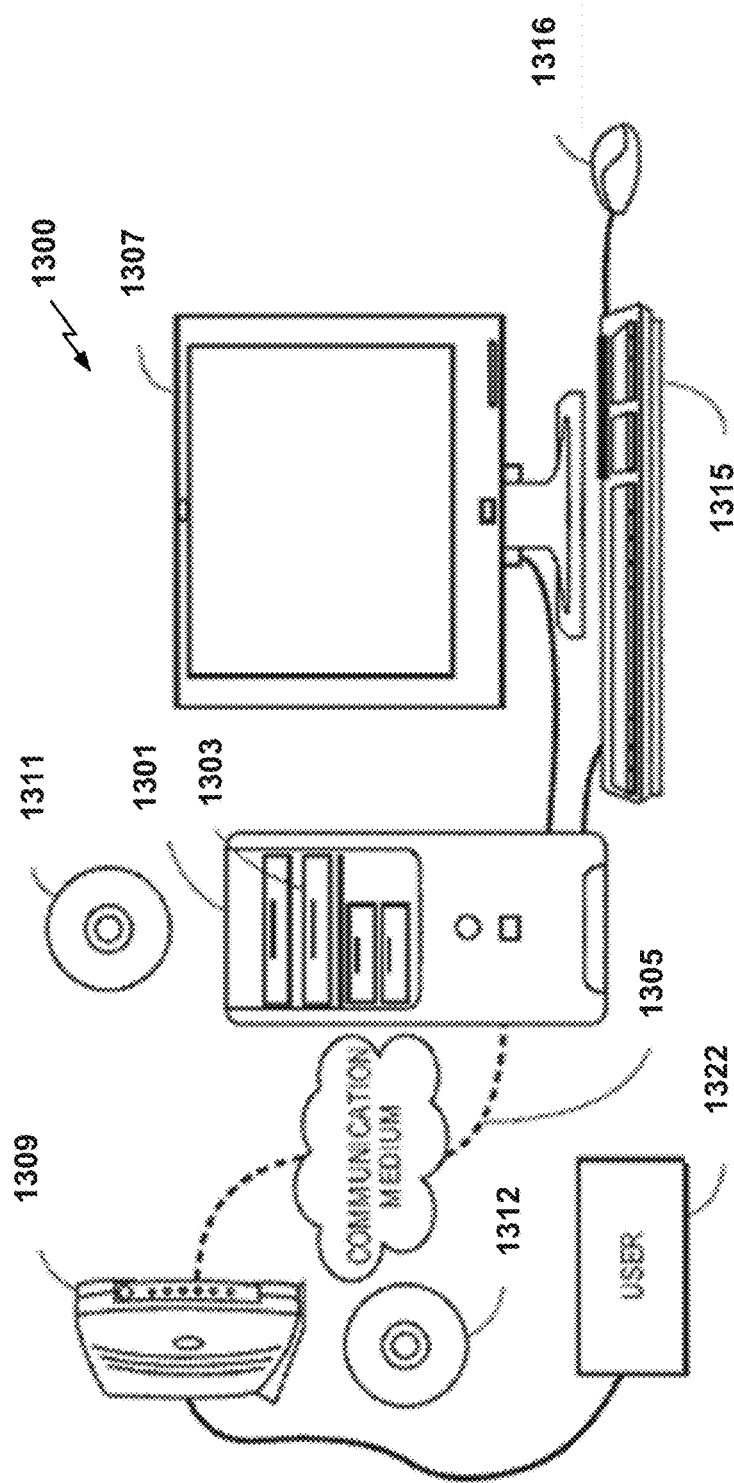
FIG. 13 shows a non-limiting exemplary instrument used in the methods of the disclosure.

In general, the computer or processor included in the presently disclosed instrument systems, as illustrated in FIG. 13, can be further understood as a logical apparatus that can read instructions from media 1311 or a network port 1305, which can optionally be connected to server 1309 having fixed media 1312. The system 1300, such as shown in FIG. 13 can include a CPU 1301, disk drives 1303, optional input devices such as keyboard 1315 or mouse 1316 and optional monitor 1307. Data communication can be achieved through the indicated communication medium to a server at a local or a remote location. The communication medium can include any means of transmitting or receiving data. For example, the communication medium can be a network connection, a wireless connection or an internet connection. Such a connection can provide for communication over the World Wide Web. It is envisioned that data relating to the present disclosure can be transmitted over such networks or connections for reception or review by a party 1322 as illustrated in FIG. 13.

Figure 14:
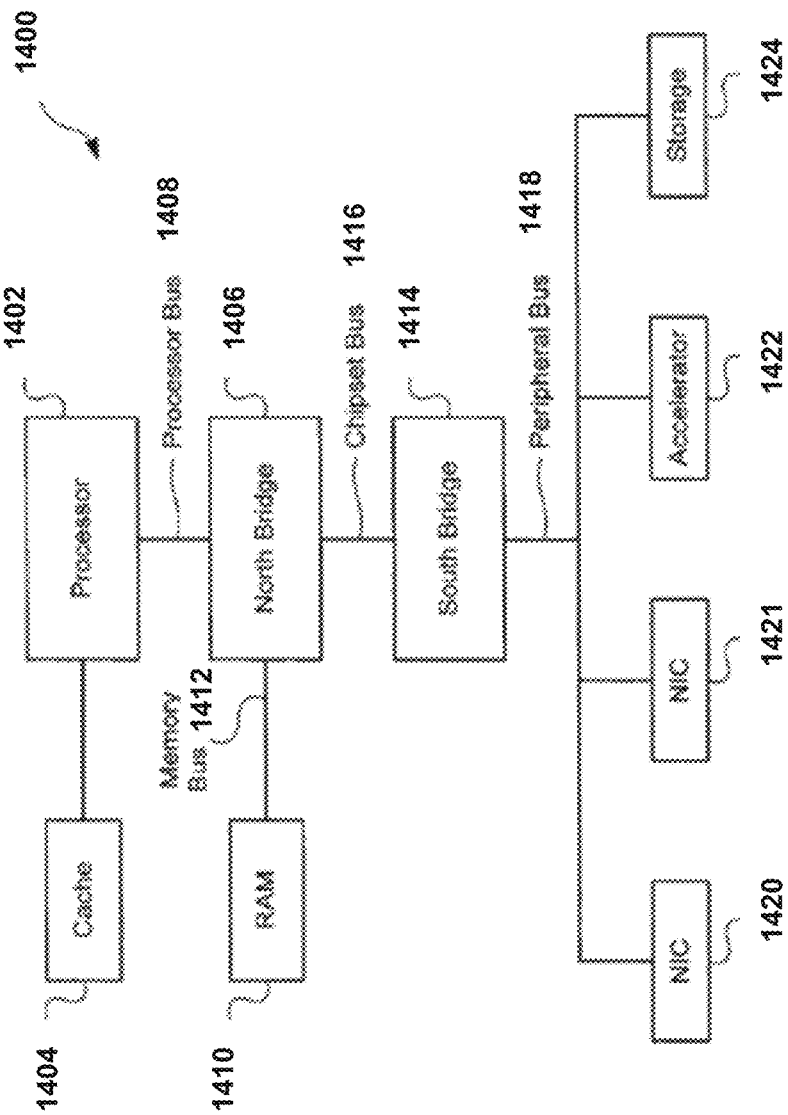
FIG. 14 illustrates a non-limiting exemplary architecture of a computer system that can be used in connection with embodiments of the present disclosure.

FIG. 14 illustrates an exemplary embodiment of a first example architecture of a computer system 1400 that can be used in connection with example embodiments of the present disclosure. As depicted in FIG. 14, the example computer system can include a processor 1402 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, or personal data assistant devices.

As illustrated in FIG. 14, a high speed cache 1404 can be connected to, or incorporated in, the processor 1402 to provide a high speed memory for instructions or data that have been recently, or are frequently, used by processor 1402. The processor 1402 is connected to a north bridge 1406 by a processor bus 1408. The north bridge 1406 is connected to random access memory (RAM) 1410 by a memory bus 1412 and manages access to the RAM 1410 by the processor 1402. The north bridge 1406 is also connected to a south bridge 1414 by a chipset bus 1416. The south bridge 1414 is, in turn, connected to a peripheral bus 1418. The peripheral bus can be, for example, PCI, PCI-X, PCI Express, or other peripheral bus. The north bridge and south bridge are often referred to as a processor chip set and manage data transfer between the processor, RAM, and peripheral components on the peripheral bus 118. In some alternative architectures, the functionality of the north bridge can be incorporated into the processor instead of using a separate north bridge chip.

In some embodiments, system 1400 can include an accelerator card 1422 attached to the peripheral bus 1418. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 1424 and can be loaded into RAM 1410 or cache 1404 for use by the processor. The system 1400 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention.

In this example, system 1400 also includes network interface cards (NICs) 1420 and 1421 connected to the peripheral bus for providing network interfaces to external storage, such as Network Attached Storage (NAS) and other computer systems that can be used for distributed parallel processing.

Figure 15:
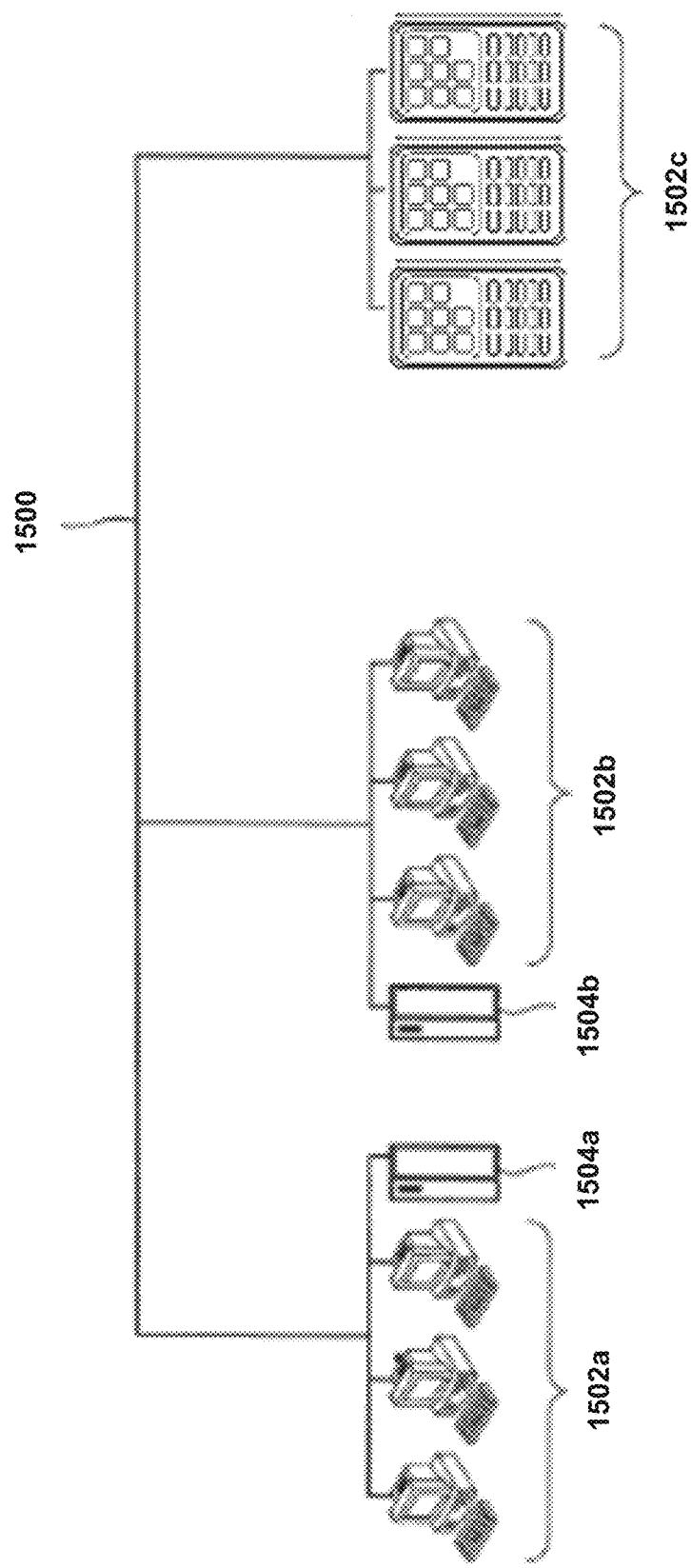
FIG. 15 illustrates a non-limiting exemplary architecture showing a network with a plurality of computer systems for use in the methods of the disclosure.

FIG. 15 illustrates an exemplary diagram showing a network 1500 with a plurality of computer systems 1502a, and 1502b, a plurality of cell phones and personal data assistants 1502c, and Network Attached Storage (NAS) 1504a, and 1504b. In example embodiments, systems

1512a, 1512b, and 1512c can manage data storage and optimize data access for data stored in Network Attached Storage (NAS) 1514a and 1514b. A mathematical model can be used for the data and be evaluated using distributed parallel processing across computer systems 1512a, and 1512b, and cell phone and personal data assistant systems 1512c. Computer systems 1512a, and 1512b, and cell phone and personal data assistant systems 1512c can also provide parallel processing for adaptive data restructuring of the data stored in Network Attached Storage (NAS) 1514a and 1514b. FIG. 15 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 16:
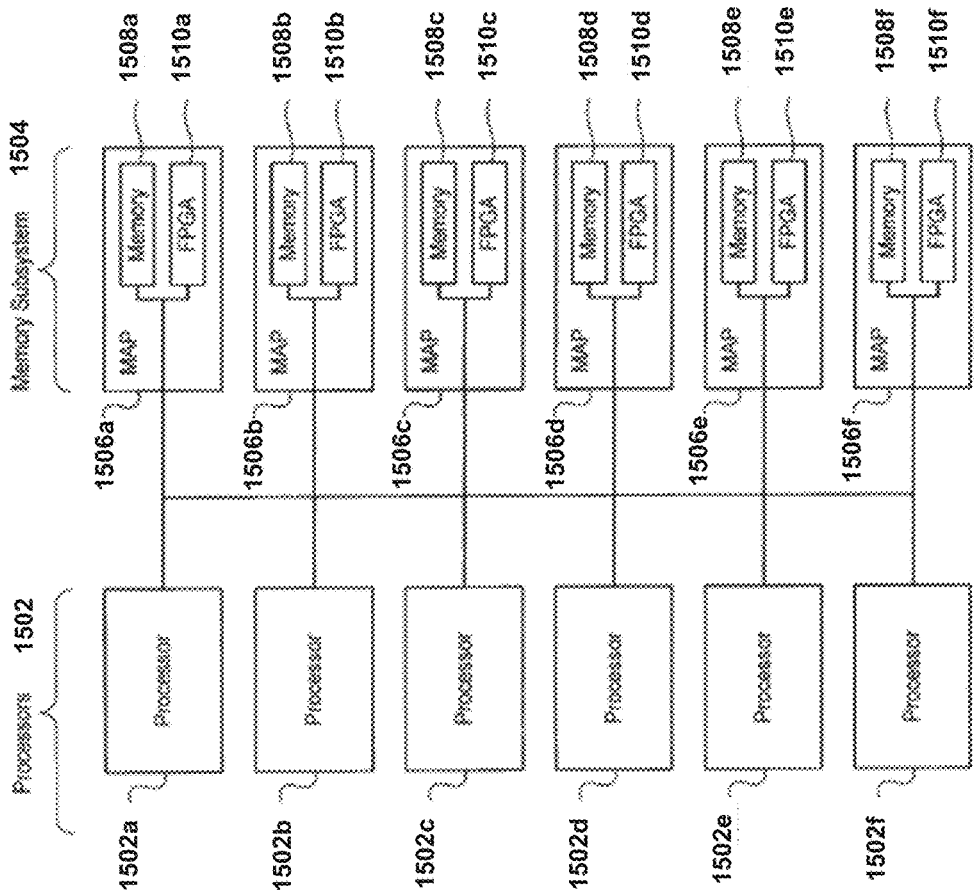
FIG. 16 illustrates a non-limiting exemplary architecture of a multiprocessor computer system using a shared virtual address memory space in accordance with the methods of the disclosure.

FIG. 16 illustrates an exemplary a block diagram of a multiprocessor computer system 1600 using a shared virtual address memory space in accordance with an example embodiment. The system includes a plurality of processors 1602a-f that can access a shared memory subsystem 1604. The system incorporates a plurality of programmable hardware memory algorithm processors (MAPs) 1606a-f in the memory subsystem 1604. Each MAP 1606a-f can comprise a memory 1608a-f and one or more field programmable gate arrays (FPGAs) 1610a-f. The MAP provides a configurable functional unit and particular algorithms or portions of algorithms can be provided to the FPGAs 1610a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOLs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer subsystem of the present disclosure can be implemented using software modules executing on any of the above or other computer architectures and systems. In other embodiments, the functions of the system can be implemented partially or completely in firmware, programmable logic devices such as field programmable gate arrays (FPGAs), system on chips (SOLs), application specific integrated circuits (ASICs), or other processing and logic elements. For example, the Set Processor and Optimizer can be implemented with hardware acceleration through the use of a hardware accelerator card, such as accelerator card.

Kits

Disclosed herein are kits for performing single cell, stochastic barcoding assays. The kit can comprise one or more substrates (e.g., microwell array), either as a free-standing substrate (or chip) comprising one or more microwell arrays, or packaged within one or more flow-cells or cartridges, and one or more solid support suspensions, wherein the individual solid supports within a suspension comprise a plurality of attached stochastic barcodes of the disclosure. In some embodiments, the kit can further comprise a mechanical fixture for mounting a free-standing substrate in order to create reaction wells that facilitate the pipetting of samples and reagents into the substrate. The kit can further comprise reagents, e.g. lysis buffers, rinse buffers, or hybridization buffers, for performing the stochastic barcoding assay. The kit can further comprise reagents (e.g. enzymes, primers, or buffers) for performing nucleic acid extension reactions, for example, reverse transcription reactions. The kit can further comprise reagents (e.g. enzymes, universal primers, sequencing primers, target-specific primers, or buffers) for performing amplification reactions to prepare sequencing libraries. The kit can comprise reagents for performing the label lithography method of the disclosure (e.g., pre-spatial labels and reagents for activating the activatable consensus sequence).

The kit can comprise one or more molds, for example, molds comprising an array of micropillars, for casting substrates (e.g., microwell arrays), and one or more solid supports (e.g., bead), wherein the individual beads within a suspension comprise a plurality of attached stochastic barcodes of the disclosure. The kit can further comprise a material for use in casting substrates (e.g. agarose, a hydrogel, PDMS, and the like).

The kit can comprise one or more substrates that are pre-loaded with solid supports comprising a plurality of attached stochastic barcodes of the disclosure. In some embodiments, there can be on solid support per microwell of the substrate. In some embodiments, the plurality of stochastic barcodes can be attached directly to a surface of the substrate, rather than to a solid support. In any of these embodiments, the one or more microwell arrays can be provided in the form of free-standing substrates (or chips), or they can be packed in flow-cells or cartridges.

In some embodiments of the disclosed kits, the kit can comprise one or more cartridges that incorporate one or more substrates. In some embodiments, the one or more cartridges can further comprise one or more pre-loaded solid supports, wherein the individual solid supports within a suspension comprise a plurality of attached stochastic barcodes of the disclosure. In some embodiments, the beads can be pre-distributed into the one or more microwell arrays of the cartridge. In some embodiments, the beads, in the form of suspensions, can be pre-loaded and stored within reagent wells of the cartridge. In some embodiments, the one or more cartridges can further comprise other assay reagents that are pre-loaded and stored within reagent reservoirs of the cartridges.

Disclosed herein are kits for performing spatial analysis of nucleic acids in a sample. The kit can comprise one or more substrates (e.g., array) of the disclosure, either as a free-standing substrate (or chip) comprising one or more arrays. The array can comprise probes of the disclosure. The kit can comprise one or more replicate arrays of the disclosure. The replicate arrays can comprise either gene-specific or oligo(dT)/poly(A) probes.

The kit can further comprise reagents, e.g. lysis buffers, rinse buffers, or hybridization buffers, for performing the assay. The kit can further comprise reagents (e.g. enzymes, primers, dNTPs, NTPs, RNase inhibitors, or buffers) for performing nucleic acid extension reactions, for example, reverse transcription reactions and primer extension reactions. The kit can further comprise reagents (e.g. enzymes, universal primers, sequencing primers, target-specific primers, or buffers) for performing amplification reactions to prepare sequencing libraries. The kit can comprise reagents for homopolymer tailing of molecules (e.g., a terminal transferase enzyme, and dNTPs). The kit can comprise reagents for, for example, any enzymatic cleavage of the disclosure (e.g., ExoI nuclease, restriction enzyme).

Kits can generally include instructions for carrying out one or more of the methods described herein. Instructions included in kits can be affixed to packaging material or can be included as a package insert. While the instructions are typically written or printed materials they are not limited to such. Any medium capable of storing such instructions and communicating them to an end user is contemplated by the disclosure. Such media can include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

Devices

Flow Cells

The microwell array substrate can be packaged within a flow cell that provides for convenient interfacing with the rest of the fluid handling system and facilitates the exchange of fluids, e.g. cell and solid support suspensions, lysis buffers, rinse buffers, etc., that are delivered to the microwell array and/or emulsion droplet. Design features can include: (i) one or more inlet ports for introducing cell samples, solid support suspensions, or other assay reagents, (ii) one or more microwell array chambers designed to provide for uniform filling and efficient fluid-exchange while minimizing back eddies or dead zones, and (iii) one or more outlet ports for delivery of fluids to a sample collection point or a waste reservoir. The design of the flow cell can include a plurality of microarray chambers that interface with a plurality of microwell arrays such that one or more different cell samples can be processed in parallel. The design of the flow cell can further include features for creating uniform flow velocity profiles, i.e. "plug flow", across the width of the array chamber to provide for more uniform delivery of cells and beads to the microwells, for example, by using a porous barrier located near the chamber inlet and upstream of the microwell array as a "flow diffuser", or by dividing each array chamber into several subsections that collectively cover the same total array area, but through which the divided inlet fluid stream flows in parallel. In some embodiments, the flow cell can enclose or incorporate more than one microwell array substrate. In some embodiments, the integrated microwell array/flow cell assembly can constitute a fixed component of the system. In some embodiments, the microwell array/flow cell assembly can be removable from the instrument.

In general, the dimensions of fluid channels and the array chamber(s) in flow cell designs will be optimized to (i) provide uniform delivery of cells and beads to the microwell array, and (ii) to minimize sample and reagent consumption. In some embodiments, the width of fluid channels will be between 50 um and 20 mm. In other embodiments, the width of fluid channels can be at least 50 um, at least 100 um, at least 200 um, at least 300 um, at least 400 um, at least 500 um, at least 750 um, at least 1 mm, at least 2.5 mm, at least 5 mm, at least 10 mm, at least 20 mm, at least 50 mm, at least 100 mm, or at least 150 mm. In yet other embodiments, the width of fluid channels can be at most 150 mm, at most 100 mm, at most 50 mm, at most 20 mm, at most 10 mm, at most 5 mm, at most 2.5 mm, at most 1 mm, at most 750 um, at most 500 um, at most 400 um, at most 300 um, at most 200 um, at most 100 um, or at most 50 um. In one embodiment, the width of fluid channels is about 2 mm. The width of the fluid channels can fall within any range bounded by any of these values (e.g. from about 250 um to about 3 mm).

In some embodiments, the depth of the fluid channels will be between 50 um and 2 mm. In other embodiments, the depth of fluid channels can be at least 50 um, at least 100 um, at least 200 um, at least 300 um, at least 400 um, at least 500 um, at least 750 um, at least 1 mm, at least 1.25 mm, at least 1.5 mm, at least 1.75 mm, or at least 2 mm. In yet other embodiments, the depth of fluid channels can at most 2 mm, at most 1.75 mm, at most 1.5 mm, at most 1.25 mm, at most 1 mm, at most 750 um, at most 500 um, at most 400 um, at most 300 um, at most 200 um, at most 100 um, or at most 50 um. In one embodiment, the depth of the fluid channels is about 1 mm. The depth of the fluid channels can fall within any range bounded by any of these values (e.g. from about 800 um to about 1 mm).

Flow cells can be fabricated using a variety of techniques and materials known to those of skill in the art. In general, the flow cell will be fabricated as a separate part and subsequently either mechanically clamped or permanently bonded to the microwell array substrate. Examples of suitable fabrication techniques include conventional machining, CNC machining, injection molding, 3D printing, alignment and lamination of one or more layers of laser or die-cut polymer films, or any of a number of microfabrication techniques such as photolithography and wet chemical etching, dry etching, deep reactive ion etching, or laser micromachining. Once the flow cell part has been fabricated it can be attached to the microwell array substrate mechanically, e.g. by clamping it against the microwell array substrate (with or without the use of a gasket), or it can be bonded directly to the microwell array substrate using any of a variety of techniques (depending on the choice of materials used) known to those of skill in the art, for example, through the use of anodic bonding, thermal bonding, or any of a variety of adhesives or adhesive films, including epoxy-based, acrylic-based, silicone-based, UV curable, polyurethane-based, or cyanoacrylate-based adhesives.

Flow cells can be fabricated using a variety of materials known to those of skill in the art. In general, the choice of material used will depend on the choice of fabrication technique used, and vice versa. Examples of suitable materials include, but are not limited to, silicon, fused-silica, glass, any of a variety of polymers, e.g. polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COL), polyethylene terephthalate (PET), epoxy resins, metals (e.g. aluminum, stainless steel, copper, nickel, chromium, and titanium), a non-stick material such as teflon (PTFE), or a combination of these materials.

Cartridges

In some embodiments of the system, the microwell array, with or without an attached flow cell, can be packaged within a consumable cartridge that interfaces with the instrument system. Design features of cartridges can include (i) one or more inlet ports for creating fluid connections with the instrument or manually introducing cell samples, bead suspensions, or other assay reagents into the cartridge, (ii) one or more bypass channels, i.e. for self-metering of cell samples and bead suspensions, to avoid overfilling or back flow, (iii) one or more integrated microwell array/flow cell assemblies, or one or more chambers within which the microarray substrate(s) are positioned, (iv) integrated miniature pumps or other fluid actuation mechanisms for controlling fluid flow through the device, (v) integrated miniature valves (or other containment mechanisms) for compartmentalizing pre-loaded reagents (for example, bead suspensions) or controlling fluid flow through the device, (vi) one or more vents for providing an escape path for trapped air, (vii) one or more sample and reagent waste reservoirs, (viii) one or more outlet ports for creating fluid connections with the instrument or providing a processed sample collection point, (ix) mechanical interface features for reproducibly positioning the removable, consumable cartridge with respect to the instrument system, and for providing access so that external magnets can be brought into close proximity with the microwell array, (x) integrated temperature control components or a thermal interface for providing good thermal contact with the instrument system, and (xi) optical interface features, e.g. a transparent window, for use in optical interrogation of the microwell array.

The cartridge can be designed to process more than one sample in parallel. The cartridge can further comprise one or more removable sample collection chamber(s) that are suitable for interfacing with stand-alone PCR thermal cyclers or sequencing instruments. The cartridge itself can be suitable for interfacing with stand-alone PCR thermal cyclers or sequencing instruments. The term "cartridge" as used in this disclosure can be meant to include any assembly of parts which contains the sample and beads during performance of the assay.

The cartridge can further comprise components that are designed to create physical or chemical barriers that prevent diffusion of (or increase path lengths and diffusion times for) large molecules in order to minimize cross-contamination between microwells. Examples of such barriers can include, but are not limited to, a pattern of serpentine channels used for delivery of cells and solid supports (e.g., beads) to the microwell array, a retractable platen or deformable membrane that is pressed into contact with the surface of the microwell array substrate during lysis or incubation steps, the use of larger beads, e.g. Sephadex beads as described previously, to block the openings of the microwells, or the release of an immiscible, hydrophobic fluid from a reservoir within the cartridge during lysis or incubation steps, to effectively separate and compartmentalize each microwell in the array.

The dimensions of fluid channels and the array chamber(s) in cartridge designs can be optimized to (i) provide uniform delivery of cells and beads to the microwell array, and (ii) to minimize sample and reagent consumption. The width of fluid channels can be between 50 micrometers and 20 mm. In other embodiments, the width of fluid channels can be at least 50 micrometers, at least 100 micrometers, at least 200 micrometers, at least 300 micrometers, at least 400 micrometers, at least 500 micrometers, at least 750 micrometers, at least 1 mm, at least 2.5 mm, at least 5 mm, at least 10 mm, or at least 20 mm. In yet other embodiments, the width of fluid channels can at most 20 mm, at most 10 mm, at most 5 mm, at most 2.5 mm, at most 1 mm, at most 750 micrometers, at most 500 micrometers, at most 400 micrometers, at most 300 micrometers, at most 200 micrometers, at most 100 micrometers, or at most 50 micrometers. The width of fluid channels can be about 2 mm. The width of the fluid channels can fall within any range bounded by any of these values (e.g. from about 250 um to about 3 mm).

The fluid channels in the cartridge can have a depth. The depth of the fluid channels in cartridge designs can be between 50 micrometers and 2 mm. The depth of fluid channels can be at least 50 micrometers, at least 100 micrometers, at least 200 micrometers, at least 300 micrometers, at least 400 micrometers, at least 500 micrometers, at least 750 micrometers, at least 1 mm, at least 1.25 mm, at least 1.5 mm, at least 1.75 mm, or at least 2 mm. The depth of fluid channels can at most 2 mm, at most 1.75 mm, at most 1.5 mm, at most 1.25 mm, at most 1 mm, at most 750 micrometers, at most 500 micrometers, at most 400 micrometers, at most 300 micrometers, at most 200 micrometers, at most 100 micrometers, or at most 50 micrometers. The depth of the fluid channels can be about 1 mm. The depth of the fluid channels can fall within any range bounded by any of these values (e.g. from about 800 micrometers to about 1 mm).

Figure 17C:
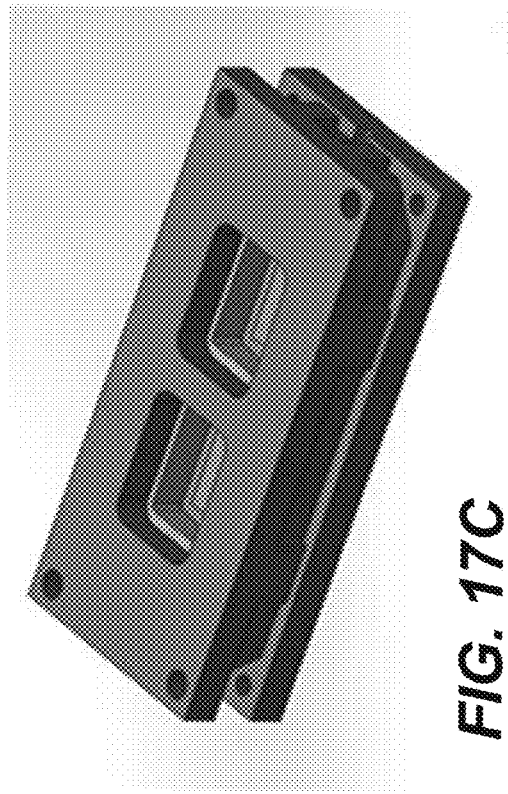
FIGS. 17A-C depicts a non-limiting exemplary cartridge for use in the methods of the disclosure.
Figure 17A:
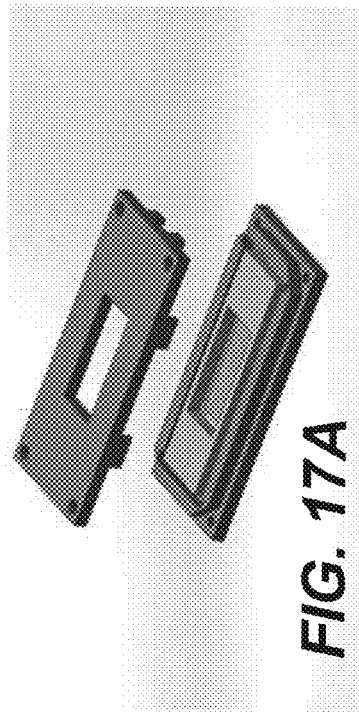

Cartridges can be fabricated using a variety of techniques and materials known to those of skill in the art. In general, the cartridges will be fabricated as a series of separate component parts (FIGS. 17A-C) and subsequently assembled using any of a number of mechanical assemblies or bonding techniques. Examples of suitable fabrication techniques include, but are not limited to, conventional machining, CNC machining, injection molding, thermoforming, and 3D printing. Once the cartridge components have been fabricated they can be mechanically assembled using screws, clips, and the like, or permanently bonded using any of a variety of techniques (depending on the choice of materials used), for example, through the use of thermal bonding/welding or any of a variety of adhesives or adhesive films, including epoxy-based, acrylic-based, silicone-based, UV curable, polyurethane-based, or cyanoacrylate-based adhesives.

Cartridge components can be fabricated using any of a number of suitable materials, including but not limited to silicon, fused-silica, glass, any of a variety of polymers, e.g. polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COL), polyethylene terephthalate (PET), epoxy resins, non-stick materials such as teflon (PTFE), metals (e.g. aluminum, stainless steel, copper, nickel, chromium, and titanium), or any combination thereof.

The inlet and outlet features of the cartridge can be designed to provide convenient and leak-proof fluid connections with the instrument, or can serve as open reservoirs for manual pipetting of samples and reagents into or out of the cartridge. Examples of convenient mechanical designs for the inlet and outlet port connectors can include, but are not limited to, threaded connectors, Luer lock connectors, Luer slip or "slip tip" connectors, press fit connectors, and the like. The inlet and outlet ports of the cartridge can further comprise caps, spring-loaded covers or closures, or polymer membranes that can be opened or punctured when the cartridge is positioned in the instrument, and which serve to prevent contamination of internal cartridge surfaces during storage or which prevent fluids from spilling when the cartridge is removed from the instrument. The one or more outlet ports of the cartridge can further comprise a removable sample collection chamber that is suitable for interfacing with stand-alone PCR thermal cyclers or sequencing instruments.

The cartridge can include integrated miniature pumps or other fluid actuation mechanisms for control of fluid flow through the device. Examples of suitable miniature pumps or fluid actuation mechanisms can include, but are not limited to, electromechanically- or pneumatically-actuated miniature syringe or plunger mechanisms, membrane diaphragm pumps actuated pneumatically or by an external piston, pneumatically-actuated reagent pouches or bladders, or electro-osmotic pumps.

The cartridge can include miniature valves for compartmentalizing pre-loaded reagents or controlling fluid flow through the device. Examples of suitable miniature valves can include, but are not limited to, one-shot "valves" fabricated using wax or polymer plugs that can be melted or dissolved, or polymer membranes that can be punctured; pinch valves constructed using a deformable membrane and pneumatic, magnetic, electromagnetic, or electromechanical (solenoid) actuation, one-way valves constructed using deformable membrane flaps, and miniature gate valves.

The cartridge can include vents for providing an escape path for trapped air. Vents can be constructed according to a variety of techniques, for example, using a porous plug of polydimethylsiloxane (PDMS) or other hydrophobic material that allows for capillary wicking of air but blocks penetration by water.

Figure 17B:
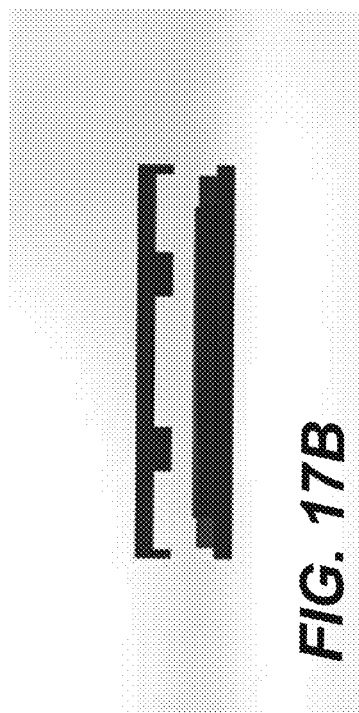

The mechanical interface features of the cartridge can provide for easily removable but highly precise and repeatable positioning of the cartridge relative to the instrument system. Suitable mechanical interface features can include, but are not limited to, alignment pins, alignment guides, mechanical stops, and the like. The mechanical design features can include relief features for bringing external apparatus, e.g. magnets or optical components, into close proximity with the microwell array chamber (FIG. 17B).

The cartridge can also include temperature control components or thermal interface features for mating to external temperature control modules. Examples of suitable temperature control elements can include, but are not limited to, resistive heating elements, miniature infrared-emitting light sources, Peltier heating or cooling devices, heat sinks, thermistors, thermocouples, and the like. Thermal interface features can be fabricated from materials that are good thermal conductors (e.g. copper, gold, silver, etc.) and can comprise one or more flat surfaces capable of making good thermal contact with external heating blocks or cooling blocks.

The cartridge can include optical interface features for use in optical imaging or spectroscopic interrogation of the microwell array. The cartridge can include an optically transparent window, e.g. the microwell substrate itself or the side of the flow cell or microarray chamber that is opposite the microwell array, fabricated from a material that meets the spectral requirements for the imaging or spectroscopic technique used to probe the microwell array. Examples of suitable optical window materials can include, but are not limited to, glass, fused-silica, polymethylmethacrylate (PMMA), polycarbonate (PC), cyclic olefin polymers (COP), or cyclic olefin copolymers (COL).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

EXAMPLES

Some aspects of the embodiments discussed above are disclosed in further detail in the following examples, which are not in any way intended to limit the scope of the present disclosure.

Example 1

Methods for Determining the Number of Distinct Targets at Spatial Locations in a Sample Using a Spatial Label The disclosure provides for methods for determining the number of distinct targets and their distinct spatial locations in a sample using a spatial label on a stochastic barcode of the disclosure. A tissue thin-slice is separated into sections. The sections are placed on a substrate in a known way. The sections are placed on a substrate such that they preserve the physical order of the tissue section. The sections are placed on a substrate such that they do not preserve the physical order of the tissue section. The tissue section is contacted with a plurality of solid supports. The tissue section is contacted with a plurality of solid supports in a known way such that a user knows which solid support with which spatial label contacted which section. A single solid support can contact each section of the tissue thin slice. The solid supports comprise a plurality of stochastic barcodes. The stochastic barcodes comprise a universal label, a spatial label, a cellular label, a molecular label, and a target-association region. The tissue thin section is imaged with the solid supports. The image captures the physical structure of the tissue thin slice and identifies the orientation of the solid supports associated with the tissue thin slice. For example, solid supports can be etched with an identifier that can be visible in the image. The sequence of the spatial label on each of the etched solid supports is pre-known.

The targets in the section of the tissue thin slice associate with the target-association region (e.g., through their poly (A) tail). The targets are cross-linked to the target-association region. The solid supports are removed from the tissue thin section. The targets associated with the target-association region are reverse transcribed using a reverse transcriptase, thereby generating a target-barcode molecule which is a transcript incorporating the labels of the stochastic barcode into its polynucleotide sequence. The target-barcode molecule is amplified using polymerase chain reaction. The sequence of the target-barcode molecule is determined, for example, through sequencing. The sequence reaction determines the spatial label, the cellular label, the molecular label, and some or all of the sequence of the target. The number of distinct targets are counted, wherein the unique occurrences of a specific molecular label indicate a distinct target. The sequence of the spatial label is used to correlate the number of the distinct targets with a position in physical space of the tissue thin slice. A map is generated that displays the location and amount of a distinct target in the tissue thin section. The amount of the distinct target is displayed as a colorimetric intensity.

Example 2

Methods for Determining the Number of Distinct Target at a Spatial Location in a Sample Using a Timing Correlation The disclosure provides for methods for determining the number of distinct targets and their distinct spatial locations in a sample using a spatial label on a stochastic barcode of the disclosure and a timing correlation. A tissue thin-slice is separated into sections using a device. The device places the sections on a substrate in a known way. The sections are placed on a substrate such that they preserve the physical order of the tissue section. The sections are placed on a substrate such that they do not preserve the physical order of the tissue section.

In some embodiments, a device takes biopsies of a solid tissue at a given rate. The device places the biopsy samples on a substrate at a given location. The location of the biopsy sample is related to the rate at which the device took the biopsy samples. This is related to the time the device was in a specific location to take the biopsy sample.

In either case, the sample/section is contacted with a plurality of solid supports. The sample/section is contacted with a plurality of solid supports in a known way such that a user knows which solid support with which spatial label contacted which section. A single solid support can contact each section of the sample/section. The solid supports comprise a plurality of stochastic barcodes. The stochastic barcodes comprise a universal label, a spatial label, a cellular label, a molecular label, and a target-association region. The sample/section is imaged with the solid supports. The image captures the physical structure of the tissue thin slice and identifies the orientation of the solid supports associated with the tissue thin slice. For example, solid supports can be etched with an identifier that can be visible in the image. The sequence of the spatial label on each of the etched solid supports is pre-known.

The targets in the section of the sample/section associate with the target-association region (e.g., through their poly (A) tail). The targets are cross-linked to the target-association region. The solid supports are removed from the sample/section. The targets associated with the target-association region are reverse transcribed using a reverse transcriptase, thereby generating a target-barcode molecule which is a transcript incorporating the labels of the stochastic barcode into its polynucleotide sequence. The target-barcode molecule is amplified using polymerase chain reaction. The sequence of the target-barcode molecule is determined, for example, through sequencing. The sequence reaction determines the spatial label, the cellular label, the molecular label, and some or all of the sequence of the target. The number of distinct targets are counted, wherein the unique occurrences of a specific molecular label indicate a distinct target. The sequence of the spatial label is used to correlate the number of the distinct targets with a specific solid support, which is correlated with a specific time at which the solid support was contacted to the sample/section. In this way, the position of the distinct targets in physical space of the sample/section and be analyzed. A map is generated that displays the location and amount of a distinct target in the sample/section. The amount of the distinct target is displayed as a colorimetric intensity.

Example 3

Method for Determining the Number of Distinct Targets at a Spatial Location in a Sample Using Label Lithography The disclosure provides for methods for determining the number of distinct targets and their distinct spatial locations in a sample using lengths of spatial labels on a stochastic barcode of the disclosure. A tissue thin-slice is separated into sections. The sections are placed on a substrate in a known way. The sections are placed on a substrate such that they preserve the physical order of the tissue section. The sections are placed on a substrate such that they do not preserve the physical order of the tissue section. In some embodiments, the tissue thin slice is not separated into section. In some embodiments, the tissue thin-slice is left intact.

In either instance, the tissue is contacted with a plurality of solid supports. A single solid support can contact each section of the tissue thin slice. The solid supports can comprise a pre-spatial label. The pre-spatial label is attached to the solid support. The pre-spatial label comprises a cellular label, a molecular label, and a target-association region. The pre-spatial label comprises an activatable consensus sequence. The activatable consensus sequence is activated to link to a spatial label block which comprises a corresponding activatable sequence. For example, the pre-spatial label comprises biotin and the spatial label block comprises avidin on one end and biotin on the other end. The spatial label block is a sequence of nucleotides that when concatenated together forms a spatial label.

Concatenation of the spatial label occurs in a geometric manner such that discrete spatial label blocks are added to specific pre-spatial labels at specific physical locations. Spatial label blocks are added in an increasing manner while moving from top to bottom across the tissue thin-slice. Spatial label blocks are then added in an increasing manner while moving from left to right across the tissue thin-slice. In this way, the length of the spatial label (i.e., comprising concatenated spatial label blocks) is indicative of a physical location in the tissue sample.

The tissue thin section is imaged with the solid supports before they have been linked to spatial label blocks. The image captures the physical structure of the tissue thin slice and identifies the orientation of the solid supports associated with the tissue thin slice. For example, solid supports can be etched with an identifier that can be visible in the image. The sequence of the spatial label on each of the etched solid supports is pre-known.

The targets in the section of the tissue thin slice associate with the target-association region (e.g., through their poly (A) tail). The targets are cross-linked to the target-association region. The solid supports are removed from the tissue thin section. The targets associated with the target-association region are reverse transcribed using a reverse transcriptase, thereby generating a target-barcode molecule which is a transcript incorporating the labels of the stochastic barcode into its polynucleotide sequence. The target-barcode molecule is amplified using polymerase chain reaction. The sequence of the target-barcode molecule is determined, for example, through sequencing. The sequence reaction determines the spatial label, the cellular label, the molecular label, and some or all of the sequence of the target. The number of distinct targets are counted, wherein the unique occurrences of a specific molecular label indicate a distinct target. The length of the spatial label is used to correlate the number of the distinct targets with a position in physical space of the tissue thin slice. A map is generated that displays the location and amount of a distinct target in the tissue thin section. The amount of the distinct target is displayed as a colorimetric intensity.

Example 4

Combinatorial Methods for Generating Large Libraries of Unique Synthetic Particles with Both DNA Barcodes and Spectrally Resolvable Barcodes This example demonstrates a combinatorial method to generate large libraries of at least $96^3$ unique synthetic particles with both DNA barcodes such as stochastic barcodes and spectrally resolvable barcodes such as optical barcodes.

Figure 18A:
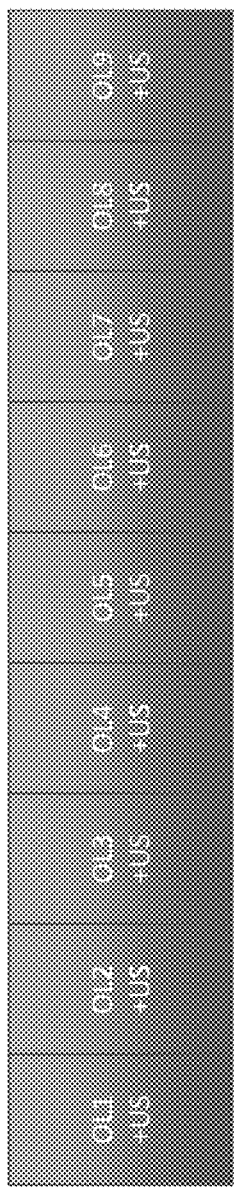
FIGS. 18A-B shows different arrangements of optical labels on the surface of a synthetic particle.
Figure 18B:
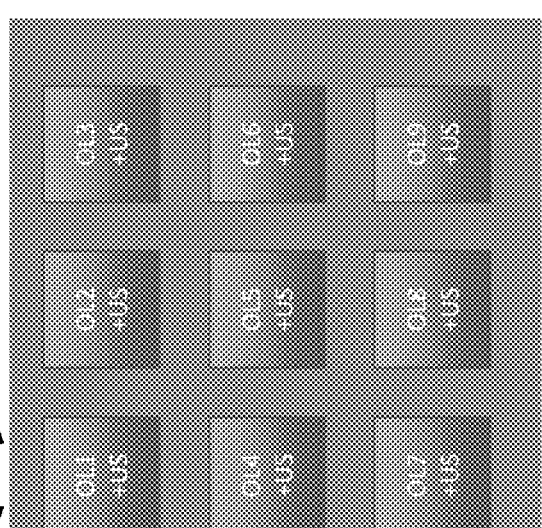

The method is used to encode synthetic particles. As shown in FIG. 18A, each synthetic particle can contain 9 "anchor regions." Each anchor region can have a size 1802 of about a few microns to tens of microns wide. The anchor regions can be arranged in a longitudinal format as shown in FIG. 18A, or a grid format as shown in FIG. 18B. The anchor regions can occupy the entire synthetic particle surface as shown in FIG. 18A, or part of the synthetic particle surface as shown in FIG. 18B. Each anchor region can have a unique optical label (OL) attached to the surface of the synthetic particle. FIGS. 18A-B show 9 optical labels, OL1-9, attached to the surface of the synthetic particle. The unique optical label can include an oligonucleotide sequence. The unique optical label can include a unique optical moiety. The unique optical moiety can be a fluorophore. OL1-3 can be used to encode cellular label part 1 corresponding to a first 96 unique cellular labels in the first encoding step. OL4-6 can be used to encode cellular label part 2 corresponding to a second 96 unique cellular labels in the second split step. OL7-9 can be used to encode cellular label part 3 corresponding to a third 96 unique cellular labels in the third split step. In addition to the 'optical label,' the entire synthetic particle surface or part of the synthetic particle surface can be attached with universal sequence (US) with 3' up, i.e. 3' end of the oligonucleotide is not attached to the synthetic particle.

Figure 19:
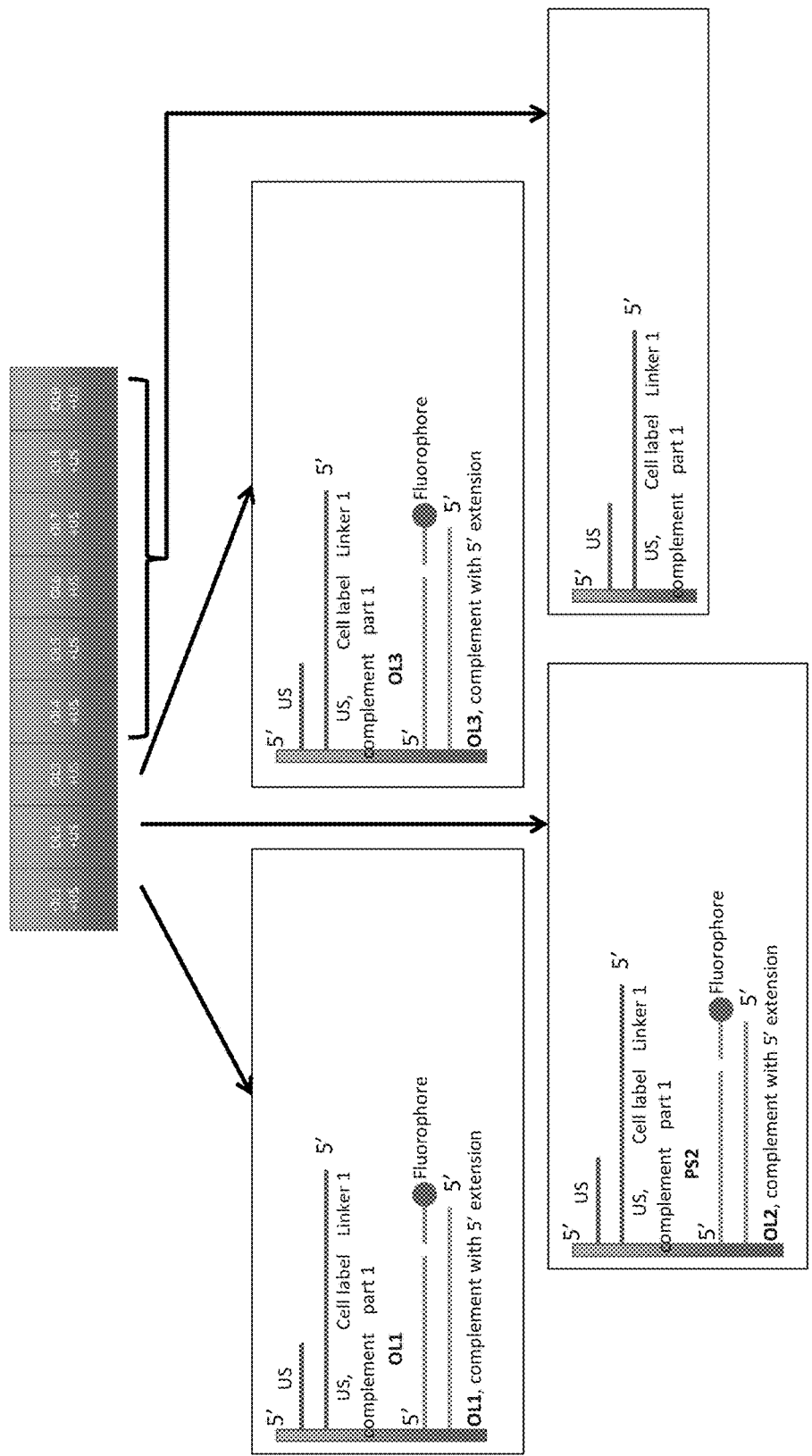
FIG. 19 shows the hybridization of oligonucleotides in the first encoding step of Example 4.

At the first encoding step/the first split step, synthetic particles are distributed across 96 wells of a first plate and hybridize to oligonucleotides in each well. FIG. 19 shows the hybridization of oligonucleotides in the first encoding step. Each well can contain, for example, 4 types of oligonucleotides. The first type of oligonucleotides each can contain a region complementary to the universal sequence (US), followed by part 1 of the cellular label (1 of 96), followed by a linker sequence (linker 1). The second type of oligonucleotides each can include a duplex structure that contains a strand complementary to OL1 with a small 5' extension, and a shorter strand complementary to the extension on the longer strand. The shorter strand can include an optical label with an optical moiety, for example a fluorophore, on the 3' end. The fluorophore can be one of five possibilities such as 5 different fluorophores, or 4 different fluorophores and the possibility of having no fluorophore. The third type of oligonucleotides each can include a duplex structure that contains a strand complementary to OL2 with a small 5' extension, and a shorter strand complementary to the extension on the longer strand. The shorter strand can include an optical label with an optical moiety, for example a fluorophore, on the 3' end. The fluorophore can be one of five possibilities such as 5 different fluorophores, or 4 different fluorophores and the possibility of having no fluorophore. The fourth type of oligonucleotides each can include a duplex structure that contains a strand complementary to OL3 with a small 5' extension, and a shorter strand complementary to the extension on the longer strand. The shorter strand can include an optical label with an optical moiety, for example a fluorophore, on the 3' end. The fluorophore can be one of five possibilities such as 5 different fluorophores, or 4 different fluorophores and the possibility of having fluorophore).

FIG. 20 is a lookup table showing the oligonucleotide content in each of the 96 wells in the first plate. The oligonucleotide content in each of the 96 wells in the first plate shows the correspondence of cellular label part 1 and encoding by OL1-3. The number of optical moieties in a group of spectrally-distinct optical moieties, i.e. the number of possibilities of fluorophores, has to be sufficient to allow encoding of at least the number of the unique synthetic particles. To encode 96 unique synthetic particles, $k^n$ has to be greater or equal to 96, where k is the number of optical moieties in the group of spectrally-distinct optical moieties, n is the number of regions. In this example, n of OL1-3 is 3, n of OL4-6 is 3, and n of OL7-9 is 3. Thus k has to be at least 5, with $k^n=5^3=125>96$.

Figure 21:
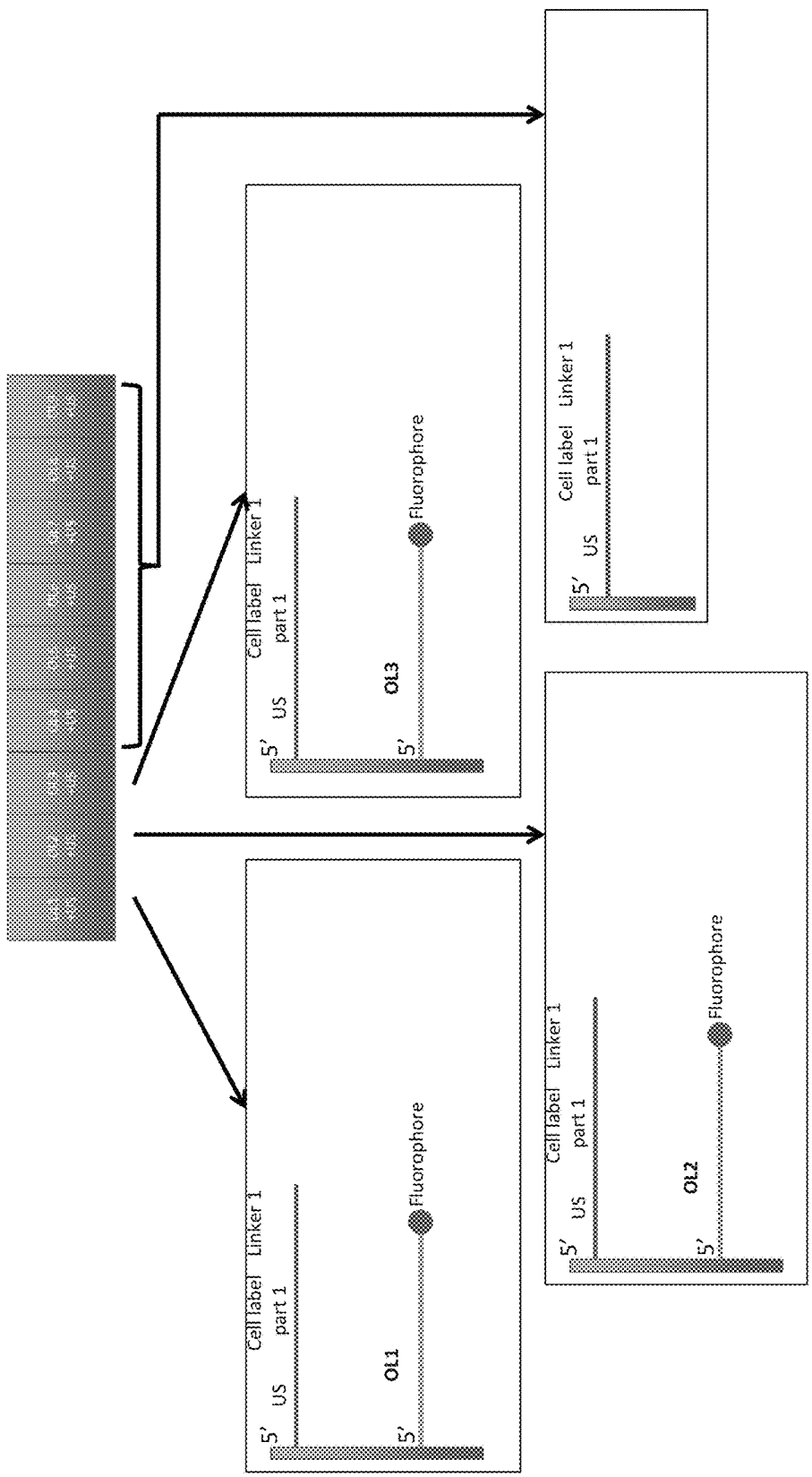
FIG. 21 shows the single stranded oligonucleotides in the various regions on the synthetic particles after polymerization, ligation, and denaturation of duplex DNA in the first encoding step.

After the synthetic particles are distributed across 96 wells of the first plate and hybridize to oligonucleotides in each well, DNA polymerase and DNA ligase can be introduced into each well. DNA polymerase can extend the US sequence with cellular label part 2 and linker 2 sequences. DNA ligase can covalently attach the fluorescent probe onto the OL oligonucleotides. FIG. 21 shows the single stranded oligonucleotides in the various regions on the synthetic particles after polymerization, ligation, and denaturation of duplex DNA in the first encoding step.

Figure 22:
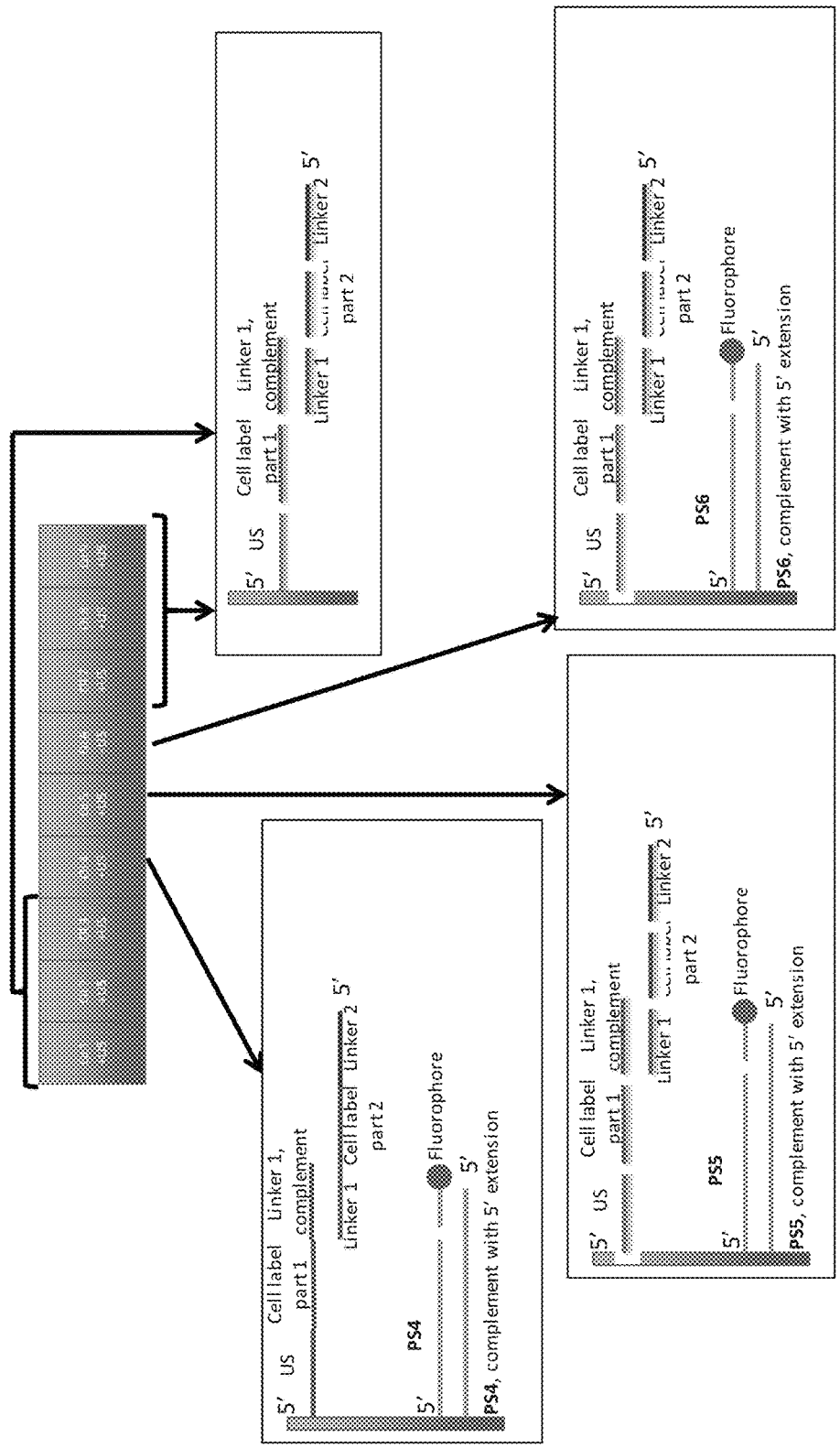
FIG. 22 shows the hybridization of oligonucleotides in the second encoding step of Example 4.

At the second encoding step including pool and second split, synthetic particles from all the wells of the first plate can be pooled, and split into each of the 96 wells of a second plate. FIG. 22 shows the hybridization of oligonucleotides in the second encoding step. Each well of the second plate can contain 4 types of oligonucleotides. Each well contains 4 types of oligonucleotides. The first type of oligonucleotide each can include linker 1, followed by part 2 of the cellular label (1 of 96), followed by another linker sequence (linker 2). The second type of oligonucleotide each can include a duplex structure that contains a strand complementary to OL4 with a small 5' extension, and a shorter strand complementary to the extension on the longer strand. The shorter strand can include an optical label with an optical moiety, for example a fluorophore, on the 3' end. The fluorophore can be one of five possibilities such as 5 different fluorophores, or 4 different fluorophores and the possibility of no fluorophore. The third type of oligonucleotide each can include a duplex structure that contains a strand complementary to OL5 with a small 5' extension, and a shorter strand complementary to the extension on the longer strand. The shorter strand can include an optical label with an optical moiety, for example a fluorophore, on the 3' end. The fluorophore can be one of five possibilities such as 5 different fluorophores, or 4 different fluorophores and the possibility of no fluorophore. The fourth type of oligonucleotide each can include a duplex structure that contains a strand complementary to OL6 with a small 5' extension, and a shorter strand complementary to the extension on the longer strand. The shorter strand can include an optical label with an optical moiety, for example a fluorophore, on the 3' end. The fluorophore can be one of five possibilities such as 5 different fluorophores, or 4 different fluorophores and the possibility of no fluorophore.

FIG. 23 is a lookup table showing the oligonucleotide content in each of the 96 wells in the second plate. The oligonucleotide content in each of the 96 wells in the second plate shows the correspondence of cellular label part 2 and encoding by OL4-6.

Figure 24:
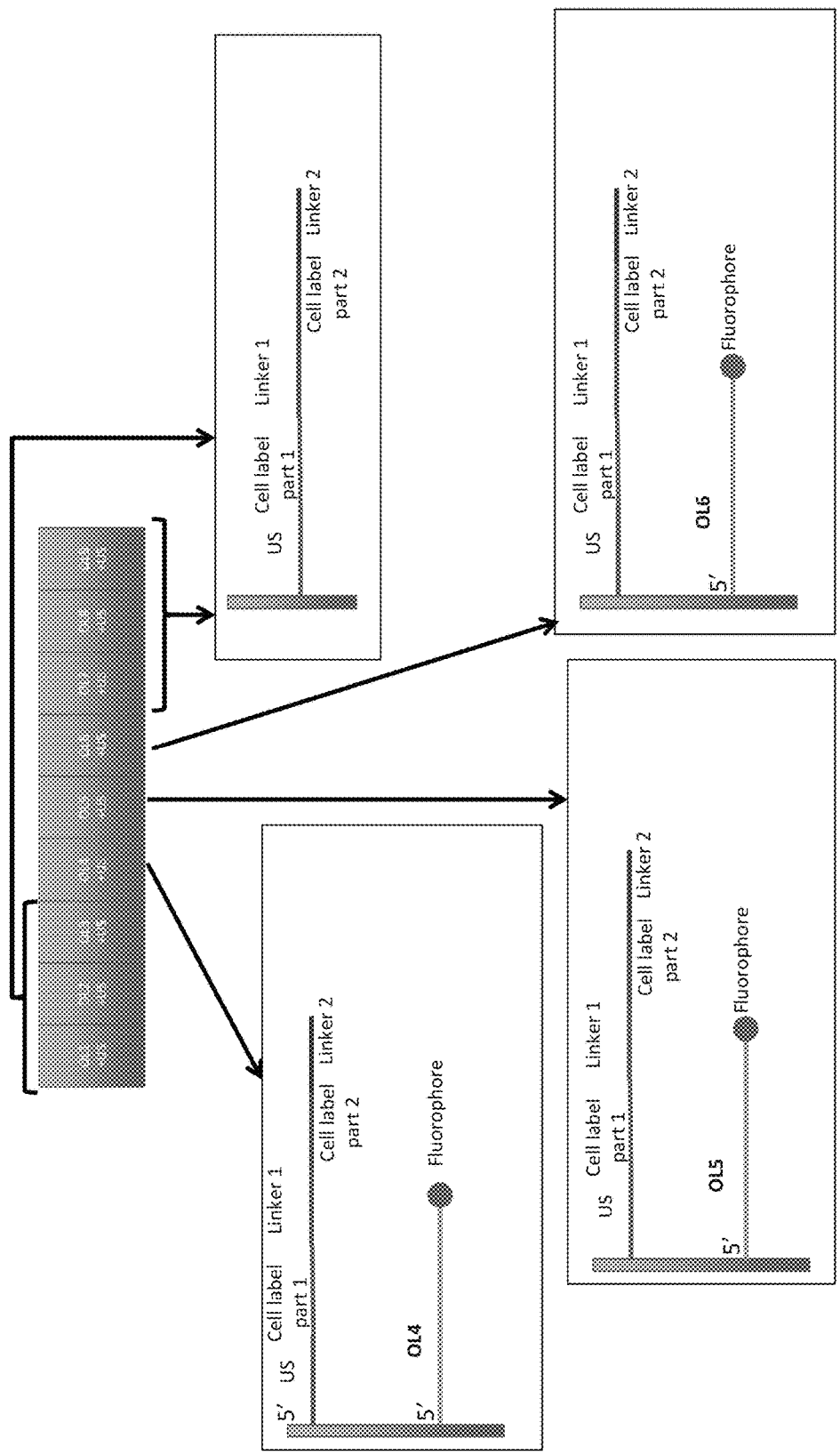
FIG. 24 shows the single stranded oligonucleotides in the various regions on the synthetic particles after polymerization, ligation, and denaturation of duplex DNA in the second encoding step.

After the synthetic particles are distributed across 96 wells of the second plate and hybridize to oligonucleotides in each well, DNA polymerase and DNA ligase can be introduced into each well. DNA polymerase can extend the US sequence with cellular label part 1 and linker 1 sequences. DNA ligase can covalently attach the fluorescent probe onto the OL oligonucleotides. FIG. 24 shows the single stranded oligonucleotides in the various regions on the synthetic particles after polymerization, ligation, and denaturation of duplex DNA in the second encoding step.

Figure 25:
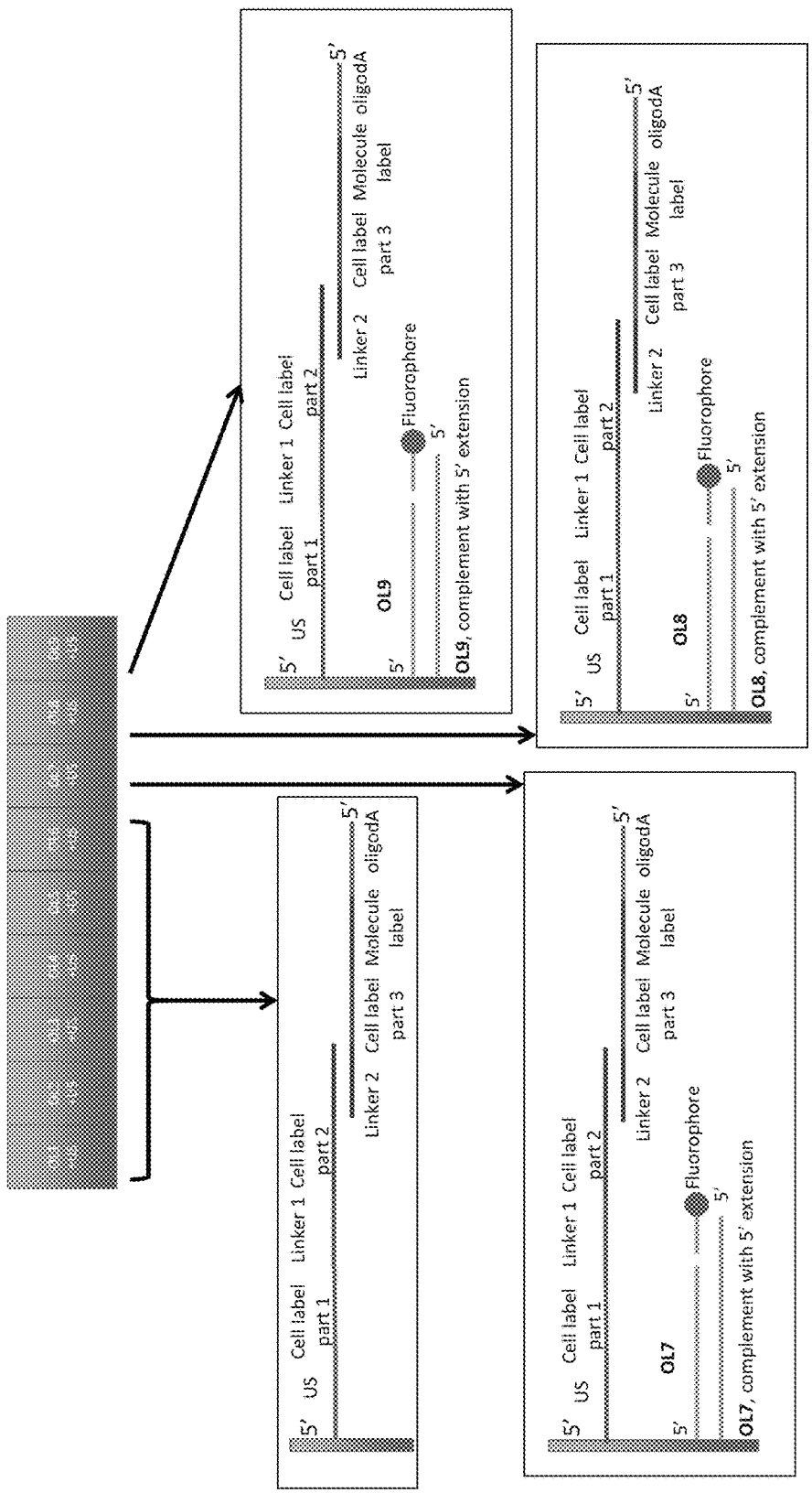
FIG. 25 shows the hybridization of oligonucleotides in the third encoding step of example 4.

At the third encoding step including pool and third split, synthetic particles from all the wells of the second plate can be pooled, and split into each of the 96 wells of a third plate. FIG. 25 shows the hybridization of oligonucleotides in the third encoding step. Each well of the third plate can contain 4 types of oligonucleotides. Each well contains 4 types of oligonucleotides. The first type of oligonucleotide each can include linker 2, followed by part 3 of the cellular label (1 of 96), followed by molecular index (randomers) and oligo (dA). The second type of oligonucleotides each can include a duplex structure that contains a strand complementary to OL7 with a small 5' extension, and a shorter strand complementary to the extension on the longer strand. The shorter strand can include an optical label with an optical moiety, for example a fluorophore, on the 3' end. The fluorophore can be one of five possibilities such as 5 different fluorophores, or 4 fluorophores and the possibility of no fluorophore. The third type of oligonucleotide each can include a duplex structure that contains a strand complementary to OL8 with a small 5' extension, and a shorter strand complementary to the extension on the longer strand. The shorter strand can include an optical label with an optical moiety, for example a fluorophore, on the 3' end. The fluorophore can be one of five possibilities such as 5 different fluorophores, or 4 fluorophores and the possibility of no fluorophore. The fourth type of oligonucleotides each can include a duplex structure that contains a strand complementary to OL9 with a small 5' extension, and a shorter strand complementary to the extension on the longer strand. The shorter strand can include an optical label with an optical moiety, for example a fluorophore, on the 3' end. The fluorophore can be one of five possibilities such as 5 different fluorophores, or 4 fluorophores and the possibility of no fluorophore.

FIG. 26 is a lookup table showing the oligonucleotide content in each of the 96 wells in the third plate. The oligonucleotide content in each of the 96 wells in the third plate shows the correspondence of cellular label part 2 and encoding by OL4-6.

Figure 27:
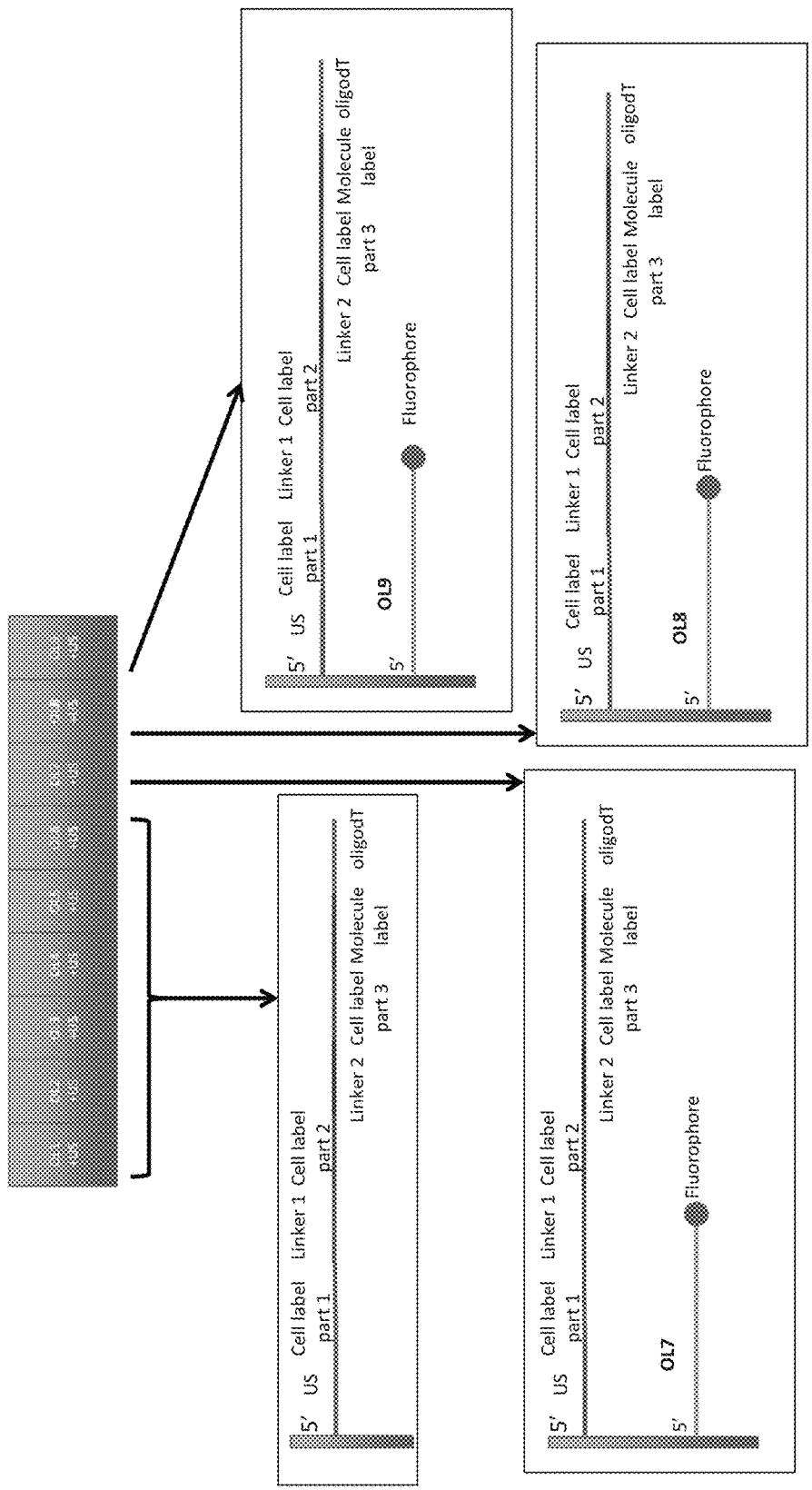
FIG. 27 shows the single stranded oligonucleotides in the various regions on the synthetic particles after polymerization, ligation, and denaturation of duplex DNA in the third encoding step.

After the synthetic particles are distributed across 96 wells of the third plate and hybridize to oligonucleotides in each well, DNA polymerase and DNA ligase can be introduced into each well. DNA polymerase can extend the US sequence with cellular label part 1 and linker 1 sequences. DNA ligase can covalently attach the fluorescent probe onto the OL oligonucleotides. FIG. 27 shows the single stranded oligonucleotides in the various regions on the synthetic particles after polymerization, ligation, and denaturation of duplex DNA in the third encoding step.

Figure 28:
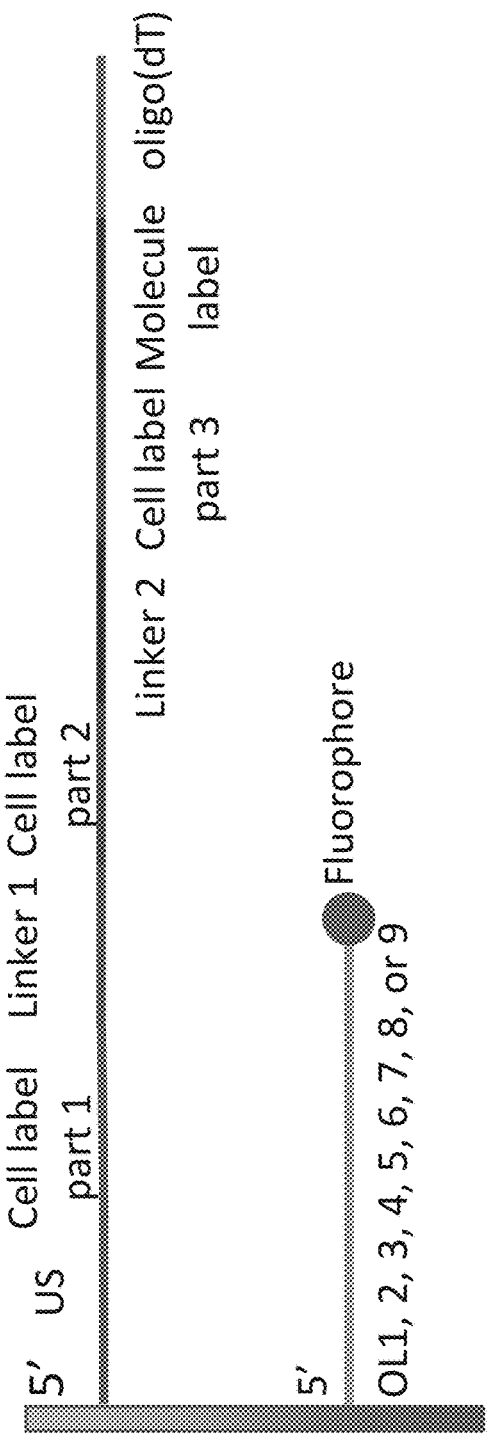
FIG. 28 is a schematic illustration of a non-limiting exemplary synthetic particle being coated with DNA barcodes and the spectrally resolvable barcode.

FIG. 28 shows an entire synthetic particle coated with both DNA barcodes and the spectrally resolvable barcode. Each DNA barcode, such as a stochastic barcode, can include a universal sequence, a cellular label, a molecular label, and an oligo(dT) region. The cellular label can include cellular label part 1, cellular label part 2, and cellular label part 3 separated by linker 1 and linker 2. Each resolvable barcode, such as an optical barcode, can include OL1-9 and the accompanying optical moieties.

Figure 29:
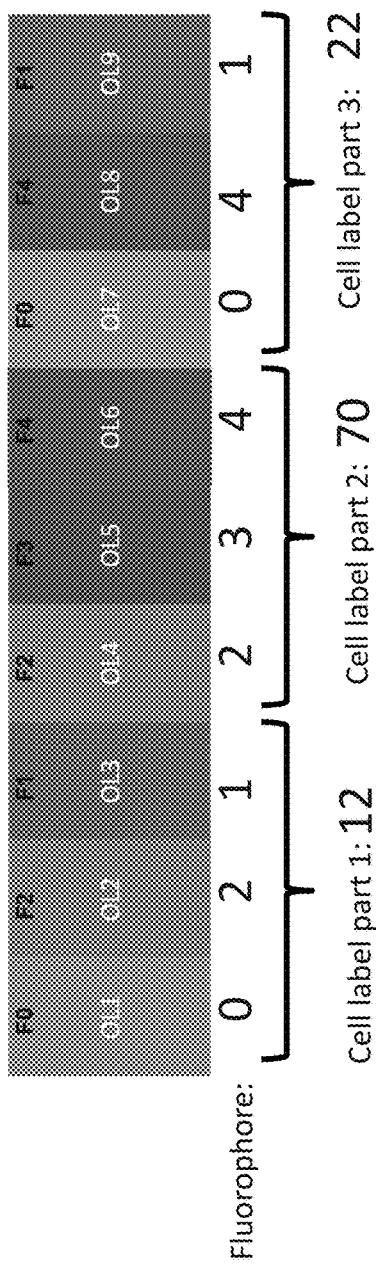
FIG. 29 shows an exemplary combination of the spectrally resolvable barcode, PS1-9, of a synthetic particle.

FIG. 29 shows an exemplary combination of the spectrally resolvable barcode, OL1-9, of a synthetic particle. The synthetic particle can be attached with a unique combination of 9 optical moieties, such as 9 fluorescence regions. The unique combination of optical moieties corresponds to a unique cellular label sequence. The fluorescence in each fluorescence region within the synthetic particle can be detected using fluorescent imaging and image analysis. The cellular label attached with the synthetic particle can then be determined based on the three tables in FIGS. 20, 23, and 26. The combination of the 9 fluorescence regions correspond to cellular label 12, 70, 22.

Altogether, these data demonstrate the use split-pool method to encode synthetic particles with both DNA labels and spectral barcodes to generate large libraries of synthetic particles.

Example 5

Generation of Spatial Gene Expression Map of Tissue Slices

This example demonstrates the use of encoded synthetic particles from Example 4 to generate spatial gene expression map of tissue slices.

First, the encoded synthetic particles are randomly sprinkled on a slide. Second, suspend the encoded synthetic particles. Upon drying, synthetic particles will be immobilized and form a non-overlapping monolayer. Third, scan the slide under different fluorescent channels. Fourth, analyze the image to deduce the spectral signature of each encoded synthetic particle, and deduce the cellular label identity using the lookup tables. Fifth, place a thin tissue section on top of the slide with the encoded synthetic particles. Sixth, place a piece of filter paper soaked with lysis buffer on top of the tissue section and apply pressure, and hold to allow cell lysis and mRNA hybridization. Seventh, layer cDNA synthesis reagents on top of the slide to carry out cDNA synthesis reaction. Eighth, layer PCR reagents on top of slide to generate copies of the cDNA. Alternatively, encoded synthetic particles can be retrieved at any step after mRNA hybridization, and the subsequent reactions can be carried out with encoded synthetic particles in tubes. Ninth, sequence PCR products to determine cellular label, molecule label, and gene identity. Tenth, map the molecules associated with each cell to the location on the slide. For each gene, obtain a 2D picture of the number of target molecules found at a specific location.

Altogether, these data demonstrate the use of encoded synthetic particles to generate spatial gene expression map of tissue slices.

Example 6

Synthetic Particle Synthesis

This example demonstrates synthetic particle synthesis by stop flow lithography.

First, fabricate a microfluidic device (e.g. PDMS or NOA) with 9 input ports converging to a single channel, leading to 1 output port. Second, in each of the input port, feed in a mixture of: Poly(ethylene glycol) diacrylate PEGDA, photoinitiator, 5' acrydite modified universal sequence (US) oligonucleotide, and 5' acrydite modified OL oligonucleotide (OL1 oligonucleotide for input port 1, OL2 oligonucleotide for input port 2, . . . , OL9 oligonucleotide for input port 9). Third, apply pressure at each of the input ports. The 9 inputs will form 9 parallel streams under laminar flow regime. Fourth, expose a region of the converged channel with UV through a photomask with the outline of the shape of the synthetic particle. Upon UV exposure, PEGDA and acrydite oligonucleotides can crosslink to form a solid hydrogel synthetic particle, with 9 regions each with a different OL oligonucleotide arranged side by side. The synthetic particles can be collected at the output port and used for the split-pool encoding process outlined in Example 4.

Altogether, these data demonstrate the use of synthetic particle synthesis by stop flow lithography.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for determining spatial locations of a plurality of single cells, comprising:
   stochastically barcoding the plurality of singe cells using a plurality of synthetic particles,
      wherein each of the plurality of synthetic particles comprises a plurality of stochastic barcodes, a first group of optical labels, and a second group of optical labels,
      wherein each of the plurality of stochastic barcodes comprises a cellular label and a molecular label,
      wherein each optical label in the first group of optical labels comprises a first optical moiety and each optical label in the second group of optical labels comprises a second optical moiety, and wherein each of the plurality of synthetic particles is associated with an optical barcode comprising the first optical moiety and the second optical moiety;

detecting the optical barcode of each of the plurality of synthetic particles to determine the location of each of the plurality of synthetic particles; and determining the spatial locations of the plurality of single cells based on the locations of the plurality of synthetic particles.

2. The method of claim 1, wherein the first optical moiety and the second optical moiety are selected from a group comprising two or more spectrally-distinct optical moieties.

3. The method of claim 1, wherein stochastically barcoding the plurality of single cells using the plurality of synthetic particles comprises contacting the plurality of single cells with the plurality of synthetic particles.

4. The method of claim 3, wherein a synthetic particle of the plurality of synthetic particles is in close proximity to a single cell or a small number of cells.

5. The method of claim 3,
wherein each of the plurality of single cells comprises a plurality of targets,
wherein stochastically barcoding the plurality of single cells further comprises hybridizing the plurality of stochastic barcodes with the plurality of targets to generate stochastically barcoded targets, and
wherein at least one of the plurality of targets is hybridized to one of the plurality of stochastic barcodes.

6. The method of claim 1, wherein cellular labels of at least two stochastic barcodes of the plurality of stochastic barcodes on one synthetic particle have the same sequence, and wherein cellular labels of at least two stochastic barcodes of the plurality of stochastic barcodes on different synthetic particles have different sequences.

7. The method of claim 1, wherein molecular labels of at least two stochastic barcodes of the plurality of stochastic barcodes on one synthetic particle have different sequences.

8. The method of claim 1, wherein the molecular labels are selected from a group comprising at least 100 molecular labels with unique sequences.

9. The method of claim 1, wherein the molecular labels are selected from a group comprising at least 1000 molecular labels with unique sequences.

10. The method of claim 1, wherein detecting the optical barcode of each of the plurality of synthetic particles to determine the location of each of the plurality of synthetic particles comprises generating an optical image showing the optical barcodes and the locations of the plurality of synthetic particles.

11. The method of claim 1, wherein the plurality of single cells comprises cells distributed across a microwell array comprising microwells.

12. The method of claim 11, comprising:
lysing the plurality of single cells; and
generating an indexed library of stochastically barcoded targets,
wherein each of the stochastically barcoded targets comprises a cellular label sequence, a molecular label sequence, and at least a portion of the complementary sequence of one of the plurality of targets.

13. The method of claim 12, comprising:
amplifying the stochastically barcoded targets of the indexed library to generate amplified stochastically barcoded targets; and sequencing the amplified stochastically barcoded targets to determine the number of amplified stochastically barcoded targets with unique molecular label sequences and identical complementary sequence,
wherein the number of amplified stochastically barcoded targets with unique molecular label sequences and identical complementary sequence is substantially the same as the occurrences of targets with sequences complementary of the identical complementary sequence in the single cell or the small number of cells.

14. The method of claim 13, wherein the labeled target molecules are amplified using bridge amplification, amplification with a gene specific primer, amplification with a universal primer, amplification with an oligo(dT) primer, or any combination thereof.

15. The method of claim 1, wherein the plurality of single cells comprises a tissue, a cell monolayer, fixed cells, a tissue section, or any combination thereof.

16. The method of claim 1, wherein a synthetic particle of the plurality of synthetic particle is a bead.

17. The method of claim 16, wherein the bead is selected from the group comprising streptavidin beads, agarose beads, magnetic beads, conjugated beads, protein A conjugated beads, protein G conjugated beads, protein A/G conjugated beads, protein L conjugated beads, oligo(dT) conjugated beads, silica beads, silica-like beads, anti-biotin microbead, anti-fluorochrome microbead, and any combination thereof.

18. The method of claim 1, wherein a synthetic particle of the plurality of synthetic particles comprises a material selected from the group comprising polydimethylsiloxane (PDMS), polystyrene, glass, polypropylene, agarose, hydrogel, paramagnetic, ceramic, plastic, glass, methylstyrene, acrylic polymer, titanium, latex, sepharose, cellulose, nylon, silicone, and any combination thereof.

19. A synthetic particle, comprising:
a plurality of stochastic barcodes, wherein each of the plurality of stochastic barcodes comprises a cellular label and a molecular label;
a first group of optical labels; and
a second group of optical labels,
wherein each optical label in the first group of optical labels comprises a first optical moiety and each optical label in the second group of optical labels comprises a second optical moiety, and
wherein each of the plurality of synthetic particles is associated with an optical barcode comprising the first optical moiety and the second optical moiety.

20. The synthetic particle of claim 19, wherein the molecular labels of the plurality of stochastic barcodes are different from one another, and the molecular labels are selected from a group comprising at least 100 molecular labels with unique sequences.

21. The synthetic particle of claim 19, wherein cellular labels of at least two stochastic barcodes of the plurality of stochastic barcodes have the same sequence.

22. The synthetic particle of claim 19, wherein molecular labels of at least two stochastic barcodes of the plurality of stochastic barcodes have different sequences.

23. The synthetic particle of claim 19, wherein molecular labels of the plurality of stochastic barcodes are selected from a group comprising at least 100 molecular labels with unique sequences.

24. The synthetic particle of claim 19, wherein molecular labels of the plurality of stochastic barcodes are selected from a group comprising at least 1000 molecular labels with unique sequences.

25. The synthetic particle of claim 19, wherein the first optical moiety and the second optical moiety are selected from a group comprising two or more spectrally-distinct optical moieties.

26. The synthetic particle of claim 19,
wherein each of the plurality of stochastic barcodes comprises a spatial label, and
wherein spatial labels of at least two stochastic barcodes of the plurality of stochastic barcodes differ from each other by at least one nucleotide.

27. The synthetic particle of claim 19,
wherein each of the plurality of stochastic barcodes further comprises a universal label, and
wherein universal labels of at least two stochastic barcodes of the plurality of stochastic barcodes have the same sequence.

28. The synthetic particle of claim 19, wherein the synthetic particle is a bead.

29. The synthetic particle of claim 28, wherein the bead is selected from the group comprising streptavidin beads, agarose beads, magnetic beads, conjugated beads, protein A conjugated beads, protein G conjugated beads, protein A/G conjugated beads, protein L conjugated beads, oligo(dT) conjugated beads, silica beads, silica-like beads, anti-biotin microbead, anti-fluorochrome microbead, and any combination thereof.

30. The synthetic particle of claim 19, wherein the synthetic particle comprises a material selected from the group comprising polydimethylsiloxane (PDMS), polystyrene, glass, polypropylene, agarose, hydrogel, paramagnetic, ceramic, plastic, glass, methylstyrene, acrylic polymer, titanium, latex, sepharose, cellulose, nylon, silicone, and any combination thereof.

* * * * *

UNITED STATES PATENT AND TRADEMARK OFFICE
CERTIFICATE OF CORRECTION

PATENT NO. : 9,727,810 B2  
APPLICATION NO. : 15/055445  
DATED : August 8, 2017  
INVENTOR(S) : Stephen P. A. Fodor Page 1 of 1

It is certified that error appears in the above-identified patent and that said Letters Patent is hereby corrected as shown below:

In Column 104 at Line 58, In Claim 1, change "singe" to --single--.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*